US010912793B2

(12) United States Patent
Zager et al.

(10) Patent No.: US 10,912,793 B2
(45) Date of Patent: Feb. 9, 2021

(54) COMPOSITIONS, KITS, AND METHODS TO INDUCE ACQUIRED CYTORESISTANCE USING STRESS PROTEIN INDUCERS

(71) Applicant: FRED HUTCHINSON CANCER RESEARCH CENTER, Seattle, WA (US)

(72) Inventors: Richard Zager, Mercer Island, WA (US); Ali C M Johnson, Mill Creek, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 16/116,411

(22) Filed: Aug. 29, 2018

(65) Prior Publication Data
US 2019/0091255 A1 Mar. 28, 2019

Related U.S. Application Data

(62) Division of application No. 15/030,008, filed as application No. PCT/US2015/052676 on Sep. 28, 2015.

(60) Provisional application No. 62/212,232, filed on Aug. 31, 2015, provisional application No. 62/057,047, filed on Sep. 29, 2014.

(51) Int. Cl.
| | |
|---|---|
| C07H 23/00 | (2006.01) |
| A61P 31/04 | (2006.01) |
| A61P 1/16 | (2006.01) |
| A61P 9/00 | (2006.01) |
| A61P 13/12 | (2006.01) |
| A61P 37/06 | (2006.01) |
| A61P 11/00 | (2006.01) |
| A61P 43/00 | (2006.01) |
| A61K 38/42 | (2006.01) |
| A61K 31/194 | (2006.01) |
| A61K 31/555 | (2006.01) |
| A61K 31/714 | (2006.01) |
| A61K 33/26 | (2006.01) |
| A01N 1/02 | (2006.01) |

(52) U.S. Cl.
CPC .......... *A61K 31/714* (2013.01); *A01N 1/0226* (2013.01); *A61K 31/194* (2013.01); *A61K 31/555* (2013.01); *A61K 33/26* (2013.01); *A61K 38/42* (2013.01); *C07H 23/00* (2013.01)

(58) Field of Classification Search
CPC .... A61P 31/04; A61P 1/16; A61P 9/00; A61P 13/12; A61P 37/06; A61P 11/00; A61P 43/00; A61K 38/42; A61K 31/194; A61K 31/555; A61K 31/714; A61K 33/26; C07H 23/00; A01N 1/02
See application file for complete search history.

(56) References Cited

U.S. PATENT DOCUMENTS

| | | | |
|---|---|---|---|
| 5,108,767 | A | 4/1992 | Mulchandani et al. |
| 5,804,551 | A | 9/1998 | Burhop |
| 8,080,520 | B2 | 12/2011 | Venkataraman et al. |
| 2004/0258745 | A1 | 12/2004 | Kai et al. |
| 2006/0166360 | A1 | 7/2006 | Berthiaume et al. |
| 2008/0317725 | A1 | 12/2008 | Baum |
| 2010/0247681 | A1 | 9/2010 | Gladwin et al. |
| 2014/0273273 | A1 | 9/2014 | Ballantyne et al. |
| 2017/0112869 | A1 | 4/2017 | Zager |

FOREIGN PATENT DOCUMENTS

CN  103 355 655 A  10/2013

OTHER PUBLICATIONS

Office Action issued in Australian Patent Application No. 2015324103 dated May 9, 2019, pp. 1-5.
Office Action issued in Israeli Patent Application No. 251455 dated Jun. 4, 2019, pp. 1-5 (with English Translation).
Barakat et al., "Upregulation of heme oxygenase 1 (HO-1) attenuates kidney damage, oxidative stress and inflammatory reaction during renal ischemia/ reperfusion injury," General Physiology and Biophysics, Mar. 2018, pp. 193-204, vol. 37, No. 2.
Drummond et al., "Prevention of neonatal hyperbilirubinemia by tin protoporphyrin IX, a potent competitive inhibitor of heme oxidation," Proc. Natl. Acad. Sci. USA, Oct. 1981, pp. 6466-6470, vol. 78, No. 10, Medical Sciences.
Extended European Search Report issued in European Patent Application No. 15846121.0 dated Mar. 6, 2018.
Jankowska et al., "Iron deficiency and heart failure: diagnositc dilemmas and therapeutic perspectives," European Heart Journal, Oct. 25, 2012, pp. 816-826c, vol. 34, No. 11.
Kruger et al., "Up-Regulation of Heme oxygenase induction with attenuation of experimentally induced corneal inflammation," Biochemical Pharmacology, Apr. 25, 1997, pp. 1069-1075, vol. 53, No. 8.
Laniado-Schwartzman et al., "Heme oxygenase induction with attenuation of experimentally induced corneal inflammation," Biochemical Pharmacology, Apr. 25, 1997, pp. 1069-1075, vol. 53, No. 8.
Agarwal et al., "Renal Response to Tissue Injury: Lessons from Heme Oxygenase-1 Gene Ablation and Expression," J. Am. Soc. Nephrol., vol. 11, 2000, pp. 965-973.
Chen et al., "Efficient Synthesis and Photodynamic Activity of Porphyrin-Saccharide Conjugates: Targeting and Incapacitating Cancer Cells," Biochemistry, vol. 43, No. 34, Jul. 28, 2004, pp. 10918-10929.

(Continued)

Primary Examiner — Sun Jae Yoo
(74) Attorney, Agent, or Firm — Jeff B. Vockrodt; Culhane Meadows PLLC

(57) ABSTRACT

The present disclosure provides compositions, kits, and methods to protect organs by inducing acquired cytoresistance without causing injury to the organ. The compositions, kits, and methods utilize heme proteins, iron and/or vitamin B12 and, optionally, agents that impact heme protein metabolism.

21 Claims, 28 Drawing Sheets
Specification includes a Sequence Listing.

(56) References Cited

OTHER PUBLICATIONS

Huang et al, "Porphyrins and Metalloporphyrins: Versatile Circular Dichroic Reporter Groups for Structural Studies," Chirality, vol. 12, Apr. 28, 2000, pp. 237-255.
International Preliminary Report on Patentability dated Apr. 13, 2017 in International Patent Application No. PCT/US2015/052676.
Invitation to Pay Additional Fees Dated Dec. 1, 2015 in International Application No. PCT/US15/52676.
Johnson et al., "Parenteral iron formulations differentially affect MCP-1, HO-1, and NGAL gene expression and renal responses to injury," Am. J. Physiol. Renal Physiol., vol. 299, American Physiological Society, 2010, pp. F426-F435.
Kaizu et al., "Preconditioning with tin-protoporphyrin IX attenuates ischemia/reperfusion injury in the rat kidney," Kidney International, vol. 63, No. 4, 2003, pp. 1393-1403
Nath et al., "Induction of Heme Oxygenase is a Rapid, Protective Response in Rhabdomyolysis in the Rat," The American Society for Clinical Investigation, Inc., vol. 90, 1992, pp. 267-270.
Office Action dated Feb. 16, 2017 for U.S. Appl. No. 15/400,690.
Office Action for U.S. Appl. No. 15/400,690, dated May 1, 2017, "Compositions, Kits, and Methods to Induce Acquired Cytoresistance Using Stress Protein Inducers," 13 Pages.
PCT Search Report and Written Opinion dated Jun. 9, 2017 for International Application No. PCT/US2017/023883, 6 pages.
Proinsias et al, "Vitamin B12: chemical modifications," Chem Soc Rev, vol. 42, No. 13, Royal Society of Chemistry, 2013, pp. 6605-6619.
Search Report and Written Opinion dated Mar. 7, 2016 in International Application No. PCT/US15/52676.
Zager et al, "Combined iron sucrose and protoporphyrin treatment protects against ischemic and toxin-mediated acute renal failure," Kidney International, vol. 90, Mar. 24, 2016, pp. 67-76.
Zager et al, "Proximal tubule haptoglobin gene activation is an integral component of the acute kidney injury stress response," Am J Physiol Renal Physiol, vol. 303, American Physiological Society, 2012, pp. F139-F148.
Zager, "Heme protein-induced tubular cytoresistance: Expression at the plasma membrane level," Kidney International, vol. 47, 1995, pp. 1336-1345.
Kato et al., 2001, caplus an 2001:607215, 2 pages.
Brasile et al., 2003, caplus an 2003:842016, 2 pages.
Moreira et al., "Vitamin B12 Protects Against Superoxide-Induced Cell Injury in Human Aortic Endothelial Cells" Free Radical Biology & Medicine, vol. 51, 2011, pp. 876-883.
Hendgen-Cotta et al., "Nitrite Reductase Activity of Myoglobin Regulates Respiration and Cellular Viability in Myocardial Ischemia-Reperfusion Injury," PNAS, vol. 105, No. 29, 2008, pp. 10256-10261.
Abraham et al., "The Physiological Significance of Heme Oxygenase," Int. J. Biochem., vol. 20, No. 6, 1988, pp. 543-558.
Office Action issued in Japanese Patent Application No. 2017-516840, dated Jul. 16, 2019, pp. 1-16 (with English Translation).

FIG. 1A
FIG. 1B
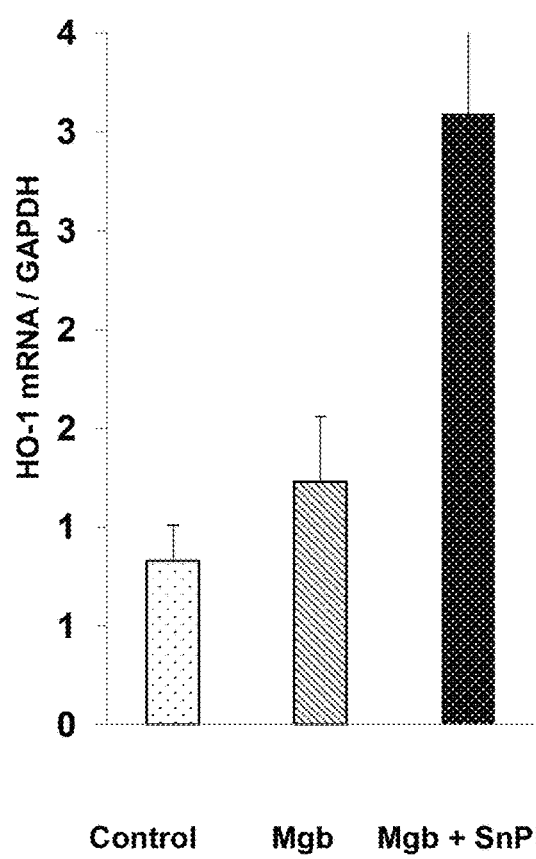
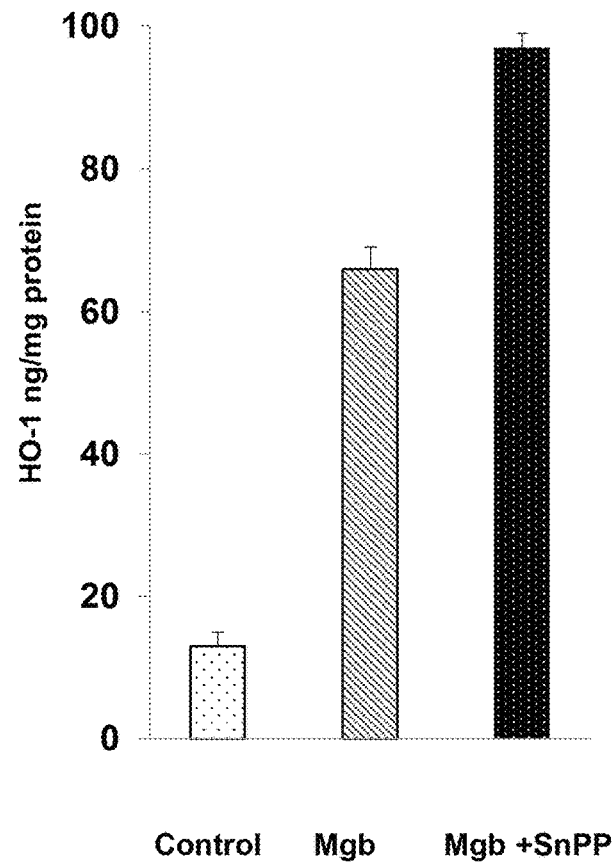

No Pre Rx

NO2-Pre Rx

Renal cortex - HO-1 protein, 18 hrs

COMPOSITIONS, KITS, AND METHODS TO INDUCE ACQUIRED CYTORESISTANCE USING STRESS PROTEIN INDUCERS

CROSS REFERENCE TO RELATED APPLICATIONS

This Application is a divisional of U.S. patent application Ser. No. 15/030,008 filed Apr. 15, 2016, which is a national stage application based on International Patent Application No. PCT/US15/52676, filed on Sep. 28, 2015, which claims priority to U.S. Provisional Patent Application No. 62/057,047 filed Sep. 29, 2014 and to U.S. Provisional Patent Application No. 62/212,232 filed Aug. 31, 2015, the entire contents all of which are incorporated by reference herein.

STATEMENT REGARDING FEDERALLY SPONSORED RESEARCH OR DEVELOPMENT

This invention was made with government support under grant DK38432 awarded by the National Institutes of Health. The government has certain rights in the invention.

FIELD OF THE DISCLOSURE

The present disclosure provides compositions, kits, and methods to protect organs by inducing acquired cytoresistance without causing injury to the organ. The compositions, kits, and methods can utilize heme proteins and, optionally, agents that impact heme protein metabolism. Other compounds that up-regulate stress proteins (e.g., iron and vitamin B12) may also be used.

BACKGROUND OF THE DISCLOSURE

Injury to a bodily organ can elicit protective responses by the organ such that it is able to better protect itself should injurious events (i.e., insults) continue or re-occur. For example, a bout of kidney injury can evoke protective responses that, after an 18 hour lag time, protect the kidney against subsequent, more severe forms of kidney damage. This protection can last for an extended period of time (days to weeks). This protective phenomenon is known in the art as "ischemic preconditioning" or "acquired cytoresistance."

One thought has been to use the phenomenon of acquired cytoresistance to preemptively protect organs, especially when a known insult is imminent. For example, the phenomenon could be induced to protect organs before an insult, such as exposure to surgery, cardiopulmonary bypass, or radiocontrast toxicity administrations. This approach has not been deployed into clinical use, however, because there has not been a mechanism to induce acquired cytoresistance in a controlled manner without causing an unacceptable injury to the organ that is to be protected.

SUMMARY OF THE DISCLOSURE

The current disclosure provides compositions, kits, and methods that allow the induction of acquired cytoresistance without causing injury to the organ. Because acquired cytoresistance can be induced without causing injury to the organ, the phenomenon can be used in a clinical setting to preemptively protect organs, especially when a known insult is approaching.

Without being bound by theory, the compositions, kits, and methods induce acquired cytoresistance by up-regulating expression of protective stress proteins. Particular embodiments induce acquired cytoresistance through administration of heme proteins at a level, or with an approach, such that the heme proteins do not cause injury to the organ that is to be protected. Induction of acquired cytoresistance can also be achieved by administering other compounds, such as iron and/or vitamin B12.

Approaches that induce acquired cytoresistance without causing injury include administering a therapeutically effective amount of a heme protein, iron and/or vitamin B12 (B12); increasing the biological half-life of the heme protein, iron and/or B12; potentiating the action of the heme protein, iron and/or B12; and reducing toxicity associated with heme protein, iron and/or B12 administration. Each of these approaches can be practiced alone or in combination.

The described approaches can be accomplished by one or more of: administering a therapeutically effective amount of a heme protein, iron and/or B12; administering the heme protein, iron and/or B12 in combination with a heme protein degradation inhibitor; administering a modified heme protein, iron and/or B12; and/or choosing an appropriate composition and delivery route.

Exemplary heme proteins include low molecular weight heme proteins, rapidly-cleared heme proteins, and myoglobin. An exemplary form of iron includes iron sucrose. Exemplary heme protein degradation inhibitors include protoporphyrins, metal protoporphyrins, and hematin. Exemplary modified heme proteins and heme protein degradation inhibitors include PEGylated heme proteins and heme protein degradation inhibitors and nitrited heme proteins and heme protein degradation inhibitors. Exemplary compositions include slow-release depots. Exemplary delivery routes include intravenous, subcutaneous, or intramuscular injection. Exemplary methods to reduce toxicity include administration with mannitol, glycine, and saline. Additional examples, embodiments, and combinations are provided in the Detailed Description.

BRIEF DESCRIPTION OF THE FIGURES

FIGS. 1A and 1B show heme oxygenase mRNA expression (FIG. 1A) and protein expression (FIG. 1B) following vehicle (control), myoglobin (Mgb) or myoglobin in combination with Sn-protoporphyrin (SnPP; Mgb+SnPP) administration 18 hours before glycerol insult. This FIG. demonstrates that the administration of myoglobin alone induces the representative cytoprotective molecule heme oxygenase 1 (HO-1), and that the combination of HO-1 plus a transient heme oxygenase inhibitor (SnPP) dramatically increases the myoglobin induced HO-1 mRNA and protein increases.

DETAILED DESCRIPTION

Figure 2:
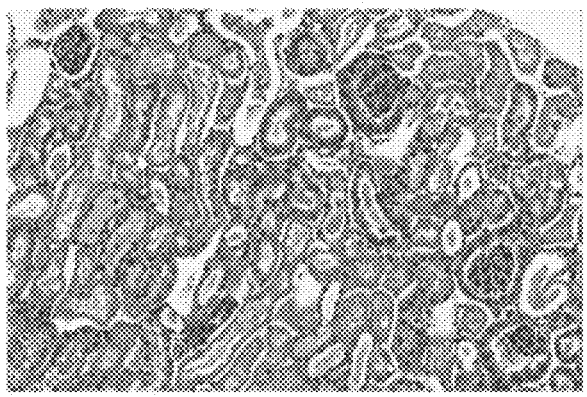
FIG. 2 left panels show cellular kidney damage following glycerol induced acute renal failure. Whereas severe injury is seen in the absence of preconditioning (extensive necrosis, top left; severe cast formation, bottom left), pre-treatment with myoglobin+SnPP 18 hrs before glycerol injection resulted in essentially normal renal histology (right panels top and bottom).
Figure 2:
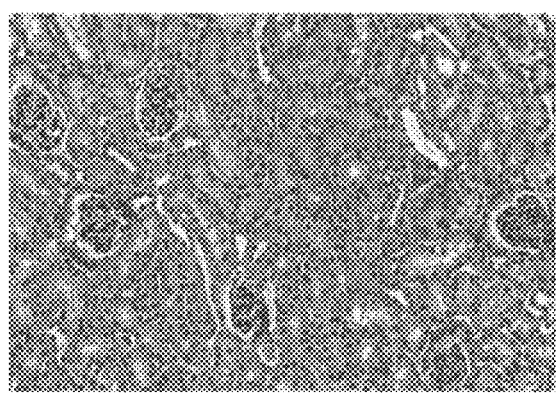
Figure 2:
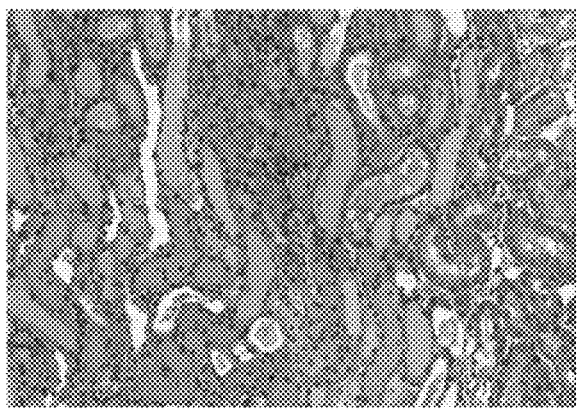
Figure 2:
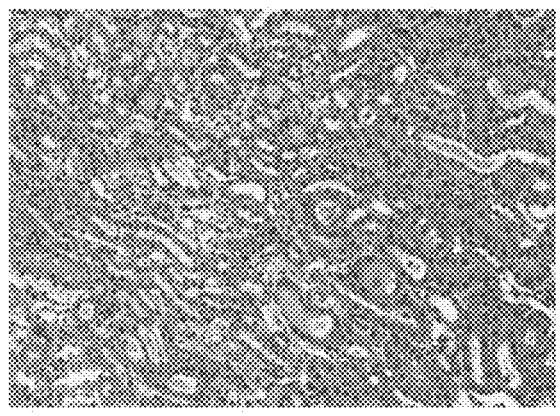

Injury to a bodily organ can elicit protective responses by the organ such that it is able to better protect itself should injurious events (i.e., insults) continue or re-occur. This protective phenomenon is known in the art as "ischemic preconditioning" or "acquired cytoresistance."

One thought has been to use the phenomenon of acquired cytoresistance to preemptively protect organs, especially when a known insult is imminent. For example, the phenomenon could be induced to protect organs before an insult, such as exposure to surgery, ballon angioplasty, induced cardiac or cerebral ischemic-reperfusion injury, or radiocontrast toxicity. Alternatively or additionally, the phenomenon could be induced in organ donors (e.g., kidney, liver) to prevent or reduce cold storage injury and/or reimplantation ischemic-reperfusion injury. These approaches have not been deployed into clinical use, however, because, until the current disclosure, there had not been a mechanism to successfully induce acquired cytoresistance in a controlled manner without causing an injury to the organ that is to be protected itself.

The current disclosure provides compositions, kits, and methods that allow the induction of acquired cytoresistance without injury to the organ that is to be protected. Because acquired cytoresistance can be induced without causing injury to the organ, the phenomenon can be used in a clinical setting to preemptively protect organs, especially when a known insult is approaching.

Without being bound by theory, the compositions, kits, and methods induce acquired cytoresistance by up-regulating expression of protective stress proteins. Acquired cytoresistance can be induced through administration of heme proteins at a level, or with an approach, such that the heme proteins do not cause an injury to the organ that is to be protected. In particular embodiments, induction of acquired cytoresistance can also be achieved by administering compounds that up-regulate stress proteins through the same or similar biological pathways utilized by heme proteins. Such compounds include, for example, iron and vitamin B12 and associated metabolites.

An "insult" is an occurrence that is likely to cause injury to an organ. Exemplary insults include shock (low blood pressure), kidney hypoperfusion, surgery, induced cardiac or cerebral ischemic-reperfusion, cardiopulmonary bypass, balloon angioplasty, radiocontrast toxicity administrations, chemotherapy, drug administration, nephrotoxic drug administration, blunt force trauma, puncture, poison, smoking, etc.

An "injury" is a detrimental effect on an organ evidenced by cell death within the organ, cell damage within the organ, damaged structure within the organ and/or decreased function of the organ as compared to one or more relevant control groups, conditions or reference levels.

"Absence of injury" to an organ, "without causing an injury" to an organ, "does not injure the organ" and similar phrases mean that any effect on an organ is, within the scope of sound medical judgment, commensurate with a reasonable benefit/risk ratio of administration. In particular embodiments, absence of an injury can be demonstrated by showing that the function of an organ is not statistically significantly different from a relevant control group, condition, or reference level according to a known test of organ function at the time using appropriate statistical comparisons. Exemplary assays of organ function include measuring markers associated with organ function; measuring the output of an organ; and measuring a performance metric of the organ as compared to one or more relevant control groups, conditions or reference levels.

By inducing acquired cytoresistance, the compositions, kits, and methods disclosed herein protect organs from injury, such as insult-induced injury. "Protecting an organ from injury" and similar phrases include one or more of: up-regulating the expression of protective stress proteins; preserving organ function in whole or in part (e.g., measuring the output of an organ; measuring a performance metric of the organ); reducing organ cell injury (in particular embodiments, as manifested by decreased leakage of intracellular proteins into the circulation), and reducing cell death within the organ as compared to one or more relevant control groups, conditions, or reference levels.

Numerous assays that can be used to assess presence or absence of an injury and associated protection are disclosed herein and can be used in animal and human models of organ function. Lack of injury and/or protection of an organ can be confirmed by comparing a relevant measure from a subject with a reference level. Reference levels can include "normal" or "control" levels or values, defined according to, e.g., discrimination limits or risk defining thresholds, in order to define cut-off points and/or abnormal values for organ function. The reference level can be a level of an indicia typically found in a subject who is not suffering from organ injury. Other terms for "reference levels" include "index," "baseline," "standard," "healthy," "pre-injury," etc. Such normal levels can vary, based on whether an indicia is used alone or in a formula combined with other indicia to output a score. Alternatively, the reference level can be derived from a database of scores from previously tested subjects who did not develop organ injury over a clinically relevant time period. Reference levels can also be derived from, e.g., a control subject or population whose organ injury status is known. In some embodiments, the reference level can be derived from one or more subjects who have been exposed to treatment for an organ injury, or from subjects who have shown improvements in organ function following injury as a result of exposure to treatment. In some embodiments the reference level can be derived from one or more subjects with organ injury who have not been exposed to treatment. A reference level can also be derived from injury severity algorithms or computed indices from population studies.

In particular embodiments, a "reference level" can refer to a standardized value for organ function which represents a level not associated with any injury; a level associated with a particular type of injury; a level associated with a severity of injury; or a level associated with a particular subject at the time of a diagnosis, at the beginning of a treatment, or at a time point during a treatment. The reference level can be a universal reference level which is useful across a variety of testing locations or can be a reference level specific for a testing location and specific assay used to measure the organ function. In certain embodiments, the reference level, is derived from (i) an individual who does not have organ injury or organ injury of a particular type; or (ii) a group of individuals who do not have organ injury or organ injury of a particular type. Reference levels for a subject can also be related to time points of the subject undergoing treatments to monitor the natural progression or regression of organ injury in the subject.

In particular embodiments, reference levels can be derived from a "dataset". A dataset represents a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

Up-Regulation of Protective Stress Proteins. Without being bound by theory, the up-regulation of a number of stress proteins leads to the induction of acquired cytoresistance. "Up-regulation" includes an increase in expression of a gene or nucleic acid molecule of interest or the activity of a protein, e.g., an increase in gene expression or protein activity as compared to the expression or activity in an otherwise identical or comparable gene or protein that has not been up-regulated.

Up-regulation of the following exemplary stress proteins can lead to the induction of acquired cytoresistance: heme oxygenase (HO), haptoglobin, hemopexin, hepcidin, alpha-1 antitrypsin (AAT), interleukin-10 (IL-10), heat-shock proteins, neutrophil gelatinase-associated lipocalin (NGAL), and HMG CoA reductase.

Heme oxygenase (HO) is the rate-limiting enzyme in heme catabolism. There are three distinct HO isozymes: HO-1 (e.g., SEQ ID NO:1), HO-2 (isoform A; e.g., SEQ ID NO:2; isoform B; e.g., SEQ ID NO. 3; isoform C; e.g., SEQ ID NO: 4), and HO-3 (e.g., SEQ ID NO:5). HO-1 is an isozyme whose expression is up-regulated following diverse forms of tissue stress, such as induced by heme proteins, heavy metals, hypoxia, and various redox sensitive pathways. In contrast, HO-2 is an isozyme expressed constitutively. HO-3 is a recently identified isozyme whose functions are currently unknown.

Haptoglobin (e.g., SEQ ID NO:6) is a blood plasma protein having a molecular weight of 86,000 to 400,000 and plays an important role in the metabolism of hemoglobin liberated into the blood stream. When liberated excessively in the blood the hemoglobin is excreted into the urine through the renal tubules, resulting in not only an iron loss but also disorders of the renal tubules. Because haptoglobin binds selectively and firmly to hemoglobin in vivo and thereby forms a hemoglobin-haptoglobin complex, it has important functions in the recovery of iron and in the prevention of renal disorders.

Hemopexin (Hpx; e.g., SEQ ID NO:7) is a 60 kDa protein which is present in the plasma in high amounts being second to only albumin, immuglobulins, and the plasma proteases. Hemopexin is often also referred to as beta-1B-glycoprotein. Hemopexin has a high affinity to heme ($K_D < 10^{-12}$M), and it is believed that the biological role of Hpx is related to the transportation of heme thus preventing heme induced oxidative damages and heme bound iron loss. Hemopexin sequesters free heme from the plasma which induces a structural change whereby the heme-Hpx complex gains increased affinity to receptors in the liver, where it is engulfed by receptor-mediated endocytosis and heme is released at the low pH in the endosomes. After that, Hpx is returned to the circulation and can undergo further rounds of transportation.

Hemopexin is folded in two homologous domains, each of 200 amino acids, joined by a 20 amino acid residue linker. There is 25% sequence identity between the two domains. Two histidines coordinate the heme iron, namely His213 from the linker peptide and His270 from a loop of the C-terminal domain, giving a stable bis-histidyl Fe(III) complex. The numbering is with respect to the mature protein. Clin. Chim. Acta, 312, 2001, 13-23 and DNA Cell Biol., 21, 2002, 297-304 provide reviews of Hpx chemistry.

Hepcidin (prepropeptide; e.g., SEQ ID NO:8) is the key signal regulating iron homeostasis (Philpott, Hepatology 35:993 (2002); Nicolas et al., Proc. Natl. Acad. Sci. USA 99:4396 (2002)). High levels of human hepcidin result in reduced iron levels, and vice versa. Mutations in the hepcidin gene which result in lack of hepcidin activity are associated with juvenile hemochromatosis, a severe iron overload disease (Roetto et al., Nat. Genet., 33:21-22, 2003). Studies in mice have demonstrated a role of hepcidin in control of normal iron homeostasis (Nicolas et al., Nat. Genet., 34:97-101, 2003; Nicolas et al., Proc. Natl. Acad. Sci. USA, 99:4596-4601, 2002; Nicolas et al., Proc. Natl. Acad. Sci. USA, 98:8780-8785, 2001).

In addition, data is accumulating implicating hepcidin in iron sequestration during inflammation (See, e.g., Weinstein et al., Blood, 100:3776-36781, 2002; Kemna et al., Blood, 106:1864-1866, 2005; Nicolas et al., J. Clin. Invest., 110: 1037-1044, 2002; Nemeth et al., J. Clin. Invest., 113:1271-

1276, 2004; Nemeth et al., Blood, 101:2461-2463, 2003 and Rivera et al., Blood, 105:1797-1802, 2005). Hepcidin gene expression has been observed to be robustly up-regulated after inflammatory stimuli, such as infections, which induce the acute phase response of the innate immune systems of vertebrates. In mice, hepcidin gene expression was shown to be up-regulated by lipopolysaccharide (LPS), turpentine, Freund's complete adjuvant, and adenoviral infections. Hepcidin expression is induced by the inflammatory cytokine IL-6. A strong correlation between hepcidin expression and anemia of inflammation was also found in patients with chronic inflammatory diseases, including bacterial, fungal, and viral infections.

Human hepcidin, a 25 amino acid peptide (e.g., SEQ ID NO:9) with anti-microbial and iron-regulating activity, was discovered independently by two groups investigating novel anti-microbial peptides. (Krause et al., FEBS Lett. 480:147 (2000); Park et al., J. Biol. Chem. 276:7806 (2001)). It has also been referred to as LEAP-1 (liver-expressed antimicrobial peptide). A hepcidin cDNA encoding an 83 amino acid pre-propeptide in mice and an 84 amino acid pre-propeptide in rat and human were subsequently identified in a search for liver specific genes that were regulated by iron (Pigeon et al., J. Biol. Chem. 276:7811 (2001)). The 24 residue N-terminal signal peptide is first cleaved to produce pro-hepcidin, which is then further processed to produce mature hepcidin, found in both blood and urine. In human urine, the predominant form contains 25 amino acids, although shorter 22 and 20 amino acid peptides are also present.

The mature peptide is notable for containing eight cysteine residues linked as four disulfide bridges. The structure of hepcidin was studied by Hunter et al., J. Biol. Chem., 277:37597-37603 (2002), by NMR using chemically synthesized hepcidin with an identical HPLC retention time to that of native hepcidin purified from urine. Hunter et al. reported their determination that hepcidin folded into a hairpin loop structure containing a vicinal disulfide bond (C1-C8, C2-C7, C3-C6, C4-05).

Alpha-1 antitrypsin (AAT; e.g., SEQ ID NO:10) is a glycoprotein secreted by hepatocytes and normally present in the serum and in the majority of tissues in high concentrations, where it acts as an inhibitor of serine proteases. Protease inhibition by AAT is an essential component of the regulation of tissue proteolysis, and AAT deficiency is implicated in the pathology of several diseases. Apart from its activity as an antiprotease, AAT could have an important anti-inflammatory biological function because it has an outstanding inhibitory capacity in respect of many inflammation mediators and in respect of oxidant radicals (Brantly M. Am J Respir Cell Mol. Biol., 2002; 27: 652-654).

Interleukin-10 (IL-10; e.g., SEQ ID NO. 11) is a pleiotropic cytokine produced by several cell types such as macrophages, monocytes, Th2 type and regulatory T-cells and B-cells. IL-10 is a cytokine with immunosuppressive and anti-inflammatory properties; it regulates a number of cellular myeloid and lymphoid activities and directly inhibits the production of several inflammatory cytokines by T-cells and Natural Killer (NK) cells. IL-10 is known as a B-cell proliferation factor and is active in autoimmunity, antibody production, tumorigenesis and transplant tolerance. Eur. J. Immunogenet. 1997 24(1): 1-8. IL-10 also alters macrophage response to infection yet stimulates Fc receptors on the same cells. Annals Allergy Asthma Immunol. 1997 79:469-483; J. Immunol. 1993 151: 1224-1234; and J. Immunol. 1992 149:4048-4052.

Heat shock proteins were originally observed to be expressed in increased amounts in mammalian cells which were exposed to sudden elevations of temperature, while the expression of most cellular proteins is significantly reduced. It has since been determined that such proteins are produced in response to various types of stress, including glucose deprivation.

Heat shock proteins have the ability to bind other proteins in their non-native states, and in particular to bind nascent peptides emerging from ribosomes or extruded into the endoplasmic reticulum. Hendrick and Hartl., Ann. Rev. Biochem. 62:349-384 (1993); Hartl., Nature 381:571-580 (1996). Further, heat shock proteins have been shown to play an important role in the proper folding and assembly of proteins in the cytosol, endoplasmic reticulum, and mitochondria; in view of this function, they are referred to as "molecular chaperones". Frydman et al., Nature 370: 111-117 (1994); Hendrick and Hartl., Ann. Rev. Biochem. 62:349-384 (1993); Hartl, Nature 381:571-580 (1996).

Examples of heat shock proteins include BiP (also referred to as grp78 (e.g., SEQ ID NO:12)), hsp/hsc70 (e.g., SEQ ID NO:13), gp96 (grp94) (e.g., SEQ ID NO:14), hsp60 (e.g., SEQ ID NO:15), hsp40 (e.g., SEQ ID NO:16), hsp70/72 (e.g., SEQ ID NO:17), and hsp90 (isoform 1; e.g., SEQ ID NO:18; isoform 2; e.g., SEQ ID NO. 19).

Lipocalins are a family of extracellular ligand-binding proteins that are found in a variety of organisms from bacteria to humans. Lipocalins possess many different functions, such as the binding and transport of small hydrophobic molecules, nutrient transport, cell growth regulation, modulation of the immune response, inflammation, and prostaglandin synthesis.

Neutrophil gelatinase-associated lipocalin (NGAL; e.g., SEQ ID NO: 20), which is also known as human neutrophil lipocalin (HNL), N-formyl peptide binding protein, and 25 kDa α2-microglobulin-related protein, is a 24 kDa protein, which can exist as a monomer, a homodimer, or a heterodimer with proteins, such as gelatinase B or matrix metalloproteinase-9 (MMP-9). A trimeric form of NGAL also has been identified. NGAL is secreted from specific granules of activated human neutrophils. Homologous proteins have been identified in mouse (24p3/uterocalin) and rat (α2-microglobulin-relatedprotein/neu-related lipocalin). Structural data have confirmed NGAL has an eight-stranded β-barrel structure, which is characteristic of lipocalins; however, NGAL has an unusually large cavity lined with more polar and positively charged amino acid residues than normally seen in lipocalins. NGAL is believed to bind small lipophilic substances, such as bacteria-derived lipopolysaccharides and formyl peptides, and may function as a modulator of inflammation.

NGAL is an early marker for acute renal injury or disease. In addition to being secreted by specific granules of activated human neutrophils, NGAL is also produced by nephrons in response to tubular epithelial damage and is a marker of tubulointerstitial (TI) injury. NGAL levels rise in acute tubular necrosis (ATN) from ischemia or nephrotoxicity, even after mild "subclinical" renal ischemia. Moreover, NGAL is known to be expressed by the kidney in cases of chronic kidney disease (CKD) and acute kidney injury ((AKI); see, e.g., Devarajan et al., Amer. J. Kidney Diseases 52(3); 395-399 (September 2008); and Bolignano et al., Amer. J. Kidney Diseases 52(3): 595-605 (September 2008)). Elevated urinary NGAL levels have been suggested as predictive of progressive kidney failure. It has been previously demonstrated that NGAL is markedly expressed by kidney tubules very early after ischemic or nephrotoxic injury in both animal and human models. NGAL is rapidly secreted into the urine, where it can be easily detected and measured. NGAL is resistant to proteases, suggesting that it can be recovered in the urine as a faithful marker of NGAL expression in kidney tubules.

The HMG-CoA reductase enzyme plays a central role in the production of cholesterol and other isoprenoids in the liver and other tissues via the mevalonate pathway. The conversion of 3-hydroxy-3-methylglutaryl-coenzyme A (HMG-CoA) to mevalonate is catalyzed by HMG-CoA reductase, and is an early and rate-limiting step in the cholesterol biosynthetic pathway in the liver and other tissues. Stress-induced increases in HMG CoA reductase mediate cholesterol synthesis leading to increased plasma membrane cholesterol.

Expression of protective stress proteins is up-regulated by administration of heme proteins. Heme proteins are metalloproteins that contain a heme prosthetic group (a protoporphyrin ring with a central Fe; a protoporphyrin ring includes four pyrole rings linked by methine bridges. Four methyl, two vinyl, and two propionate side chains can also be attached). In particular embodiments, the heme proteins are low molecular weight heme proteins. "Low molecular weight heme proteins" include those with a molecular weight of 25 kDa or less; 24 KDa or less; 23 kDa or less; 22 kDa or less; 21 kDa or less; 20 kDa or less; 19 kDa or less; 18 kDa or less; 17 kDa or less; 16 kDa or less; 15 kDa or less; 14 kDa or less; 13 kDa or less; 12 kDa or less; 11 kDa or less; or 10 kDa or less. In another embodiment, heme proteins are rapidly cleared when administered intravenously. "Rapidly cleared" means a urinary excretion rate that has a urinary clearance rate of >50% of serum creatinine or urea. In another embodiment the heme proteins are low molecular weight heme proteins that are rapidly cleared when administered intravenously. Myoglobin (e.g., SEQ ID NO:21) is one heme protein that can be used with the compositions, kits, and methods disclosed herein. References to heme proteins include modified heme proteins, variant heme proteins and D-substituted analog heme proteins. References to myoglobin include modified myoglobin, variant myoglobin and D-substituted analog myoglobin as described elsewhere herein.

Myoglobin is present in striated muscle tissue and functions to store and deliver oxygen by reversibly binding 02 at myoglobin's open binding site. Through this reversible binding, myoglobin creates an intracellular source of oxygen for cellular mitochondria. Unlike hemoglobin, another heme protein, myoglobin naturally exists only as a monomer.

When muscle tissue is damaged, myoglobin is released into the bloodstream. Large amounts of myoglobin in the blood can cause renal injury by provoking constriction of renal vessels, forming obstructing casts in the lumina of renal tubules, and initiating interstitial inflammation, as described in Zager, R. A., Ren. Fail., 14, 341-344 (1992). Moreover, Nath et al. state that heme proteins, such as hemoglobin, when released into the extracellular space, can instigate tissue toxicity and that myoglobin is directly implicated in the pathogenesis of renal failure in rhabdomyolysis. J. Clin. Invest., 1992 Jul. (90)1: 267-70. Accordingly, heme proteins and myoglobin in particular can damage the renal system.

Based on these known detrimental effects of heme proteins, including myoglobin, it was not expected that heme proteins such as myoglobin could play a role in inducing acquired cytoresistance without causing an organ injury. Thus, one aspect of the current disclosure includes identifying compositions, kits, and methods to administer myoglobin in a manner that induces acquired cytoresistance without causing an injury to the organ that it is administered to protect.

Approaches that allow heme protein administration to induce acquired cytoresistance without causing an organ injury include selecting a therapeutically effective amount of the heme protein; increasing the biological half-life of the heme protein; potentiating the action of the heme protein; and reducing toxicity associated with heme protein administration.

One embodiment disclosed herein includes selecting a therapeutically effective amount of a heme protein, such as myoglobin. Therapeutically effective amounts, methods to identify therapeutically effective amounts and exemplary therapeutically effective amounts are described more fully below.

The biological half-life of a heme protein can be extended by administering the heme protein in combination with a heme protein degradation inhibitor. In particular embodiments, heme protein degradation inhibitors can reduce or eliminate the cleavage of the heme protein's porphoryin ring by HO, reducing or eliminating release of the heme protein's toxic Fe content. In particular embodiments, administration of a heme protein degradation inhibitor in combination with a heme protein can allow for administration of lower doses of the heme protein.

In particular embodiments, any compound that blocks binding of heme to HO can function as a heme protein degradation inhibitor. For example, a number of synthetic analogs of iron protoporphyrin IX are known. These compounds are commercially available and/or can be readily synthesized by known methods. They include, for example, platinum, zinc, nickel, cobalt, copper, silver, manganese, chromium, and tin protoporphyrin IX. For convenience, these compounds can be referred to generically as Me-protoporphyrin or MePP, were Me stands for metal, and specifically by utilizing the chemical symbol for the metal such as Cr-protoporphyrin (CrPP), Sn-protoporphyrin (SnPP), Zn-protoporphyrin (ZnPP) for the chromium, tin, and zinc protoporphyrin compounds respectively.

Hemin and/or hematin can also be used as competitive HO-1 inhibitors. In some instances, hemin and hematin are used interchangeably and refer to protoporphyrin IX containing a ferric iron ion attached to a chloride ligand. Others distinguish hemin and hematin, referring to the Cl ligand form as hemin and referring to hematin as the same compound with hydroxide attached to the iron ion rather than chloride. Both can be used as competitive HO-1 inhibitors within the teachings of the current disclosure. Indeed, and as stated, any compound that blocks binding of heme to HO can function as a heme protein degradation inhibitor.

That blocking the action of HO could beneficially assist in the induction of acquired cytoresistance without causing an injury was unexpected. For example, Nath et al., showed that knocking out the HO-1 gene in mice worsened renal injury in the glycerol model of heme protein toxicity. The authors stated that HO-1 is a critical protectant against acute heme protein-induced toxicity in vivo. Am. J. of Path., 2000 May 156(5): 1527-1535.

Moreover, that Me-protoporphyrins could be used in combination with a heme protein to induce acquired cytoresistance without causing an injury was unexpected. This is because Me-protoporphyrins are generally thought to adversely affect organs in various models of organ injury. For example, Agarwal et al. found that pretreatment with Sn-protoporphyrin exacerbated renal injury in a HO-based in vivo model of heme protein mediated renal injury. Particularly, pretreatment with Sn-protoporphyrin led to higher serum creatinine values on days 3 through 5 and lower inulin clearances on day 5. Renal hemodynamics studied at day 2 after cisplatin demonstrated reduced renal blood flow rates, increased renal vascular resistance and increased fractional excretion of sodium in rats treated with Sn-protoporphyrin. Kidney Int. 1995 Oct. 48(4): 1298-307. In the glycerol model rhabdomyolysis, Nath et al., found that the kidney responds to high amounts of heme proteins by inducing HO and that blocking the action of HO with a competitive inhibitor (here, Sn-protoporphyrin) exacerbated kidney dysfunction. J. Clin. Invest. 1992 July: 90(1): 267-70. Ferenbach et al., and Goodman et al., have similarly shown that inhibition of HO using Me-protoporphyrins worsens renal damage. See Nephron. Exp. Nephrol. 2010 April 115(3): e33-7 and Kidney Int. 2007 October 72(8): 945-53 respectively. Based on these teachings of the art, one of ordinary skill in the art would not have expected the beneficial effects of HO-1 inhibition currently disclosed.

Without being bound by theory, heme proteins activate redox sensitive transcription factors, leading to the up-regulation of redox sensitive cytoprotective proteins. This pathway is initiated by Mgb's iron content. Thus, as demonstrated herein alternative approaches for inducing iron-mediated renal tubular cytoprotective gene signaling are also effective. These alternative approaches include administration of iron and/or vitamin B12. The rationale for B12 is that both cobalt and cyanide can independently induce HO-1. Thus, B12 represents a safe method to administer both cyanide and cobalt as a single agent, as both are integral parts of the B12 molecule.

Modified heme proteins and heme protein degradation inhibitors (e.g., protoporphyrins, hemin, hematin) can include those with (a) increased protein serum half-life and/or functional in vivo half-life, (b) reduced protein antigenicity, (c) increased protein storage stability, (d) increased protein solubility, (e) prolonged circulating time, and/or (f) increased bioavailability, e.g. increased area under the curve (AUC).

In particular embodiments, modified heme proteins and heme protein degradation inhibitors ("modifications") include those wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. Amino acid(s) can be modified, for example, co-translationally or post-translationally during recombinant production (e.g., N-linked glycosylation at N—X-S/T motifs during expression in mammalian cells) or modified by synthetic means. The modified amino acid can be within the sequence or at the terminal end of a sequence. Modifications also include nitrited heme proteins, such as nitrited myoglobin.

In its native state, myoglobin is 17 kDa and thus is rapidly filtered and excreted by the kidney. By increasing myoglobin's size, its excretion can be slowed, thus, allowing for a more prolonged and durable protective effect. In one embodiment, the modified protein is a PEGylated heme protein or heme protein degradation inhibitor.

PEGylation is one method that can be used to increase the size of myoglobin and other low molecular weight proteins. PEGylation is a process by which polyethylene glycol (PEG) polymer chains are covalently conjugated to other molecules such as drugs or proteins. Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

Covalent attachment of proteins or peptides to PEG has proven to be a useful method to increase the circulating half-lives of proteins and peptides in the body (Abuchowski, A. et al., Cancer Biochem. Biophys., 1984, 7:175-186; Hershfield, M. S. et al., N. Engl. J. Medicine, 1987, 316: 589-596; and Meyers, F. J. et al., Clin. Pharmacol. Ther., 1991, 49:307-313). The attachment of PEG to proteins and peptides not only protects the molecules against enzymatic degradation, but also reduces their clearance rate from the body. The size of PEG attached to a protein has significant impact on the circulating half-life of the protein. The ability of PEGylation to decrease clearance is generally not a function of how many PEG groups are attached to the protein, but the overall molecular weight of the altered protein. PEGylation decreases the rate of clearance from the bloodstream by increasing the apparent molecular weight of the molecule. Up to a certain size, the rate of glomerular filtration of proteins is inversely proportional to the size of the protein. Usually the larger the PEG is, the longer the in vivo half-life of the attached protein is. In addition, PEGylation can also decrease protein aggregation (Suzuki et al., Biochem. Bioph. Acta vol. 788, pg. 248 (1984)), alter protein immunogenicity (Abuchowski et al.; J. Biol. Chem. vol. 252 pg. 3582 (1977)), and increase protein solubility as described, for example, in PCT Publication No. WO 92/16221).

Several sizes of PEGs are commercially available (Nektar Advanced PEGylation Catalog 2005-2006; and NOF DDS Catalogue Ver 7.1), which are suitable for producing proteins with targeted circulating half-lives. A variety of active PEGs have been used including mPEG succinimidyl succinate, mPEG succinimidyl carbonate, and PEG aldehydes, such as mPEG-propionaldehyde.

In another embodiment, the modified protein is a nitrited heme protein or nitrited heme protein degradation inhibitor. Nitrite is involved in regulating production of nitric oxide (NO) from nitric oxide synthase (NOS) independent pathways. Inorganic nitrite can undergo a one electron reduction back to NO through various mechanisms with oxygen-binding heme proteins (hemoglobin and myoglobin), deoxyhemoglobin, deoxymyoglobin, xanthine oxidoreductase, endothelial NOS, acidic disproportionation, and members of the mitochondrial electron transport chain, e.g., mitochondrial heme proteins all being potential electron donors.

Nitrite binding to heme iron, such as in myoglobin, can increase the heme protein's ability to up-regulate expression of stress proteins, such as, heat shock proteins (e.g., HSP 72); HO-1; haptoglobin; hemopexin, hepcidin, IL-10, AAT, NGAL and/or HMG CoA reductase. Nitrite-Fe binding disclosed herein can also decrease toxicity associated with heme protein administration. Without being bound by theory, up-regulated expression of stress proteins serves to promote acquired cytoresistance.

Nitrited forms of active ingredients are used in particular embodiments because, without being bound by theory, the current disclosure suggests that following glomerular filtration, N-Mgb and SnPP undergo proximal tubule uptake where they activate redox sensitive transcription factors, leading to the up-regulation of redox sensitive cytoprotective proteins. Again without being bound by theory, this pathway is initiated by Mgb's iron (Fe) content. Nitrite binding to Mgb Fe facilitates Fe signaling while reducing potential Fe toxicity. Concomitant administration of SnPP also facilitates Fe signaling. These same pathways can be activated in extra-renal organs via SnPP tissue binding sites/signaling and Mgb uptake via scavenger receptors.

Reference to proteins including heme proteins, heme protein degradation inhibitors, and protective stress proteins described herein also include variants and D-substituted analogs thereof.

"Variants" of proteins disclosed herein include proteins having one or more amino acid additions, deletions, stop positions, or substitutions, as compared to a protein disclosed herein.

An amino acid substitution can be a conservative or a non-conservative substitution. Variants of proteins disclosed herein can include those having one or more conservative amino acid substitutions. A "conservative substitution" involves a substitution found in one of the following conservative substitutions groups: Group 1: alanine (Ala or A), glycine (Gly or G), Ser, Thr; Group 2: aspartic acid (Asp or D), Glu; Group 3: asparagine (Asn or N), glutamine (Gln or Q); Group 4: Arg, lysine (Lys or K), histidine (His or H); Group 5: Ile, leucine (Leu or L), methionine (Met or M), valine (Val or V); and Group 6: Phe, Tyr, Trp.

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of proteins disclosed herein also include sequences with at least 70% sequence identity, at least 80% sequence identity, at least 85% sequence, at least 90% sequence identity, at least 95% sequence identity, at least 96% sequence identity, at least 97% sequence identity, at least 98% sequence identity, or at least 99% sequence identity to a protein disclosed herein. More particularly, variants of the proteins disclosed herein include proteins that share: 70% sequence identity with any of e.g., SEQ ID NO:1-29; 80% sequence identity with any of e.g., SEQ ID NO:1-29; 81% sequence identity with any of e.g., SEQ ID NO:1-29; 82% sequence identity with any of e.g., SEQ ID NO:1-29; 83% sequence identity with any of e.g., SEQ ID NO:1-29; 84% sequence identity with any of e.g., SEQ ID NO:1-29; 85% sequence identity with any of e.g., SEQ ID NO:1-29; 86% sequence identity with any of e.g., SEQ ID NO:1-29; 87% sequence identity with any of e.g., SEQ ID NO:1-29; 88% sequence identity with any of e.g., SEQ ID NO:1-29; 89% sequence identity with any of e.g., SEQ ID NO:1-29; 90% sequence identity with any of e.g., SEQ ID NO:1-29; 91% sequence identity with any of e.g., SEQ ID NO:1-29; 92% sequence identity with any of e.g., SEQ ID NO:1-29; 93% sequence identity with any of e.g., SEQ ID NO:1-29; 94% sequence identity with any of e.g., SEQ ID NO:1-29; 95% sequence identity with any of e.g., SEQ ID NO:1-29; 96% sequence identity with any of e.g., SEQ ID NO:1-29; 97% sequence identity with any of e.g., SEQ ID NO:1-29; 98% sequence identity with any of e.g., SEQ ID NO:1-29; or 99% sequence identity with any of e.g., SEQ ID NO:1-29.

Variants of myoglobin can include myoglobin proteins that share: 70% sequence identity with e.g., SEQ ID NO:21; 80% sequence identity with e.g., SEQ ID NO:21; 81% sequence identity with e.g., SEQ ID NO:21; 82% sequence identity with e.g., SEQ ID NO:21; 83% sequence identity with e.g., SEQ ID NO:21; 84% sequence identity with e.g., SEQ ID NO:21; 85% sequence identity with e.g., SEQ ID NO:21; 86% sequence identity with e.g., SEQ ID NO:21; 87% sequence identity with e.g., SEQ ID NO:21; 88% sequence identity with e.g., SEQ ID NO:21; 89% sequence identity with e.g., SEQ ID NO:21; 90% sequence identity with e.g., SEQ ID NO:21; 91% sequence identity with e.g., SEQ ID NO:21; 92% sequence identity with e.g., SEQ ID NO:21; 93% sequence identity with e.g., SEQ ID NO:21; 94% sequence identity with e.g., SEQ ID NO:1; 95% sequence identity with e.g., SEQ ID NO:21; 96% sequence identity with e.g., SEQ ID NO:21; 97% sequence identity with e.g., SEQ ID NO:21; 98% sequence identity with e.g., SEQ ID NO:21; or 99% sequence identity with e.g., SEQ ID NO:21.

"% sequence identity" refers to a relationship between two or more sequences, as determined by comparing the sequences. In the art, "identity" also means the degree of sequence relatedness between protein sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced.

"Default values" mean any set of values or parameters which originally load with the software when first initialized.

"D-substituted analogs" include protein disclosed herein having one more L-amino acids substituted with one or more D-amino acids. The D-amino acid can be the same amino acid type as that found in the reference sequence or can be a different amino acid. Accordingly, D-analogs can also be variants.

While exemplary sequences are provided herein, sequence information provided by public databases can be used to identify additional related and relevant protein sequences and associated nucleic acid sequences encoding such proteins.

Iron. Reference to iron can include iron molecules or iron in an iron-containing complex. "Iron-containing complexes" or "iron complexes" are compounds that contain iron in the (II) or (III) oxidation state, complexed with an organic compound. Iron complexes include iron polymer complexes, iron carbohydrate complexes, and iron aminoglycosan complexes. These complexes are commercially available and/or can be synthesized by methods known in the art.

Examples of iron carbohydrate complexes include iron simple saccharide complexes, iron oligosaccharide complexes, and iron polysaccharide complexes, such as: iron carboxymaltose, iron sucrose, iron polyisomaltose (iron dextran), iron polymaltose (iron dextrin), iron gluconate, iron sorbital, iron hydrogenated dextran, which may be further complexed with other compounds, such as sorbital, citric acid and gluconic acid (for example iron dextrin-sorbitol-citric acid complex and iron sucrose-gluconic acid complex), and mixtures thereof.

Examples of iron aminoglycosan complexes include iron chondroitin sulfate, iron dermatin sulfate, iron keratan sulfate, which may be further complexed with other compounds and mixtures thereof.

Examples of iron polymer complexes include iron hyaluronic acid complex, iron protein complexes, and mixtures thereof. Iron protein complexes include ferritin, transferritin, as well as ferritin or transferritin with amino acid substitutions, and mixtures thereof.

Particular embodiments utilize low molecular weight iron complexes (e.g., low molecular weight iron sucrose complexes). The molecular weight of the complex can be less than 25,000 and non-polymeric. In additional embodiments, the molecular weight of the complex can be less than 12,000 or less than 5000 or less than 2500. It is to be understood that the lower the molecular weight of the iron complex and, correspondingly, the smaller the iron complex, the faster the iron complex may be incorporated into a patient's blood.

In particular embodiments, iron within the claims and exemplary embodiments refers to iron sucrose.

Vitamin B12 & Metabolites. Vitamin B12 is unique among vitamins in that it contains a metal ion, cobalt. Particular embodiments include the water soluble cyanocobalamin which is an organometallic compound with a trivalent cobalt ion bound inside a corrin ring. Methylcobalamin and 5-deoxyadenosyl cobalamin are forms of vitamin B12 primarily used by the human body. Additional forms include adenosyl cobalamin and hydroxyl cobalamin. Vitamin B12 may be obtained from any appropriate synthetic or natural source, and all analogues, derivatives, salts, and prodrugs, as well as mixtures thereof.

In embodiments, a derivative of vitamin B12 that can be utilized is produced by cleaving at least a portion of the $PO_4^-$ group of vitamin B12. For example, the $PO_4$ group of vitamin B12 can be cleaved using a nuclease, or removed with a nuclease in combination with a phosphatase. A derivative of vitamin B12 can have a structure

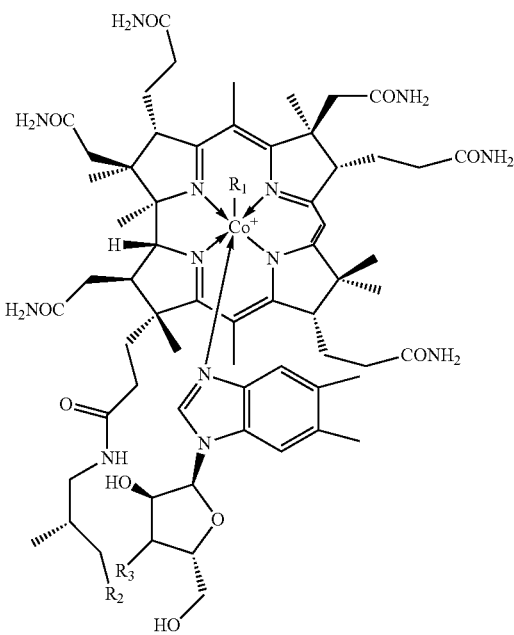

where $R_1$ can be 5'-deoxyadenosyl, $CH_3$, OH, or CN; $R_2$ can be OH or H; and $R_3$ can be OH or H.

In embodiments, vitamin B12 can be coupled with a saccharide-metal complex. Additionally, a derivative of vitamin B12 can be coupled with a saccharide-metal complex. In some embodiments, a saccharide-metal complex can be derived from a disaccharide. For example a saccharide-metal complex can be derived from sucrose. In other examples, a saccharide-metal complex can be derived from lactose. In illustrative examples, the saccharide-metal complex can be iron sucrose. By coupling vitamin B12 with iron sucrose, iron and vitamin B12 can be delivered to an organ using a single structure.

The linkage between a saccharide-metal complex and vitamin B12 or a derivative of vitamin B12 can be formed using an acid-labile hydrazine linker. Additionally, the linkage between a saccharide-metal complex and vitamin B12 or a derivative of vitamin B12 can be formed using an acid labile hydrazone linker. Examples of a hydrazone linker used in conjunction with vitamin B12 is discussed in Bagnato J D, Eilers A L, Horton R A, Grisson C B: Synthesis and characterization of a cobalamin-colchicine conjugate as a novel tumor-targeted cytotoxid. J. Org. Chem. 2004: 69, 8987-8996. In other embodiments, the linkage between a saccharide-metal complex and vitamin B12 or a derivative of vitamin B12 can be formed using a polyether. To illustrate, polyethylene glycol can be used to link a saccharide-metal complex to vitamin B12 or a derivative of vitamin B12. In additional embodiments, the linkage between a saccharide-metal complex and vitamin B12 or a derivative of vitamin B12 can be formed using a peptide linker. In illustrative examples, a poly-glycine-serine linker can be used to couple a saccharide-metal complex to vitamin B12 or a derivative of vitamin B12. In further embodiments, the linkage between a saccharide-metal complex and vitamin B12 or a derivative of vitamin B12 can be formed using one or more peptides. In other illustrative examples, a polyamide can be used to link a saccharide-metal complex with vitamin B12 or a derivative of vitamin B12. In particular illustrative examples, a protease resistant polyamide can be used to link a saccharide-metal complex with vitamin B12 or a derivative of vitamin B12.

In some cases, the linkage between a saccharide-metal complex and vitamin B12 or a derivative of vitamin B12 can be formed at multiple sites of the saccharide-metal complex. For example, the linkage between a saccharide-metal complex and vitamin B12 or a derivative of vitamin B12 can be at multiple hydroxyl sites of the saccharide-metal complex. In other embodiments, the linkage between a saccharide-metal complex and vitamin B12 or a derivative of vitamin B12 can be at a single site of the saccharide-metal complex. To illustrate, the linkage between a saccharide-metal complex and vitamin B12 or a derivative of vitamin B12 can be at a single hydroxyl site of the saccharide-metal complex. Additionally, the linkage between a saccharide-metal complex and vitamin B12 can be with the phosphate group of vitamin B12 and a hydroxyl group of the saccharide-metal complex. Further, the linkage between a saccharide-metal complex and a derivative of vitamin B12 can be between a hydroxyl group of the saccharide-metal complex and a site resulting from cleaving the phosphate group from vitamin B12.

Example structures having a linkage between a saccharide-metal complex and vitamin B12 can have the following form:

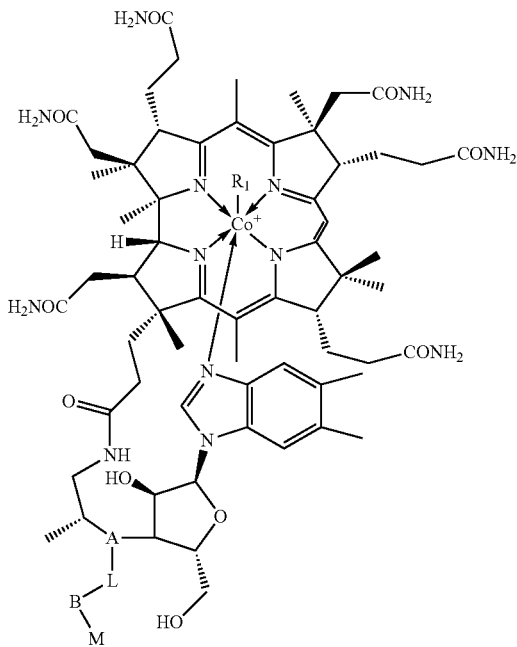

where $R_1$ can be 5'-deoxyadenosyl, $CH_3$, OH, or CN; A is a phosphate group, L is a linker, B is a saccharide-based structure, and M is a metal complexed with the saccharide-based structure. In illustrative embodiments, A can be $PO_4$, L can be a hydrazone linker, B can be a saccharide-based structure, and M can be Fe. In embodiments, B can include 10-16 carbon atoms, 9-15 oxygen atoms, and 16-28 hydrogen atoms. In particular embodiments, B can be derived from sucrose.

Example structures having a linkage between a saccharide-metal complex and a derivative of vitamin B12 can have the following form:

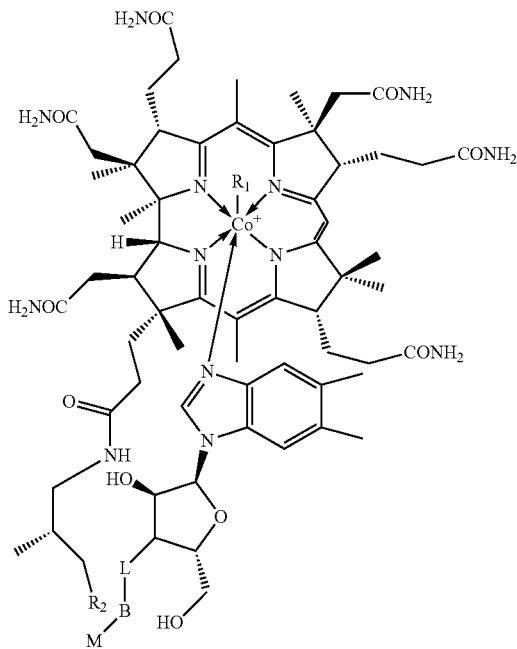

where $R_1$ can be 5'-deoxyadenosyl, $CH_3$, OH, or CN; $R_2$ can be OH or H; L is a linker, B is a saccharide-based structure, and M is a metal complexed with the saccharide-based structure. In illustrative embodiments, L can be a hydrazone linker and M can be Fe. In embodiments, B can include 10-16 carbon atoms, 9-15 oxygen atoms, and 16-28 hydrogen atoms. In particular embodiments, B can be derived from sucrose.

Additional example structures having a linkage between a saccharide-metal complex and a derivative of vitamin B12 can have the following form:

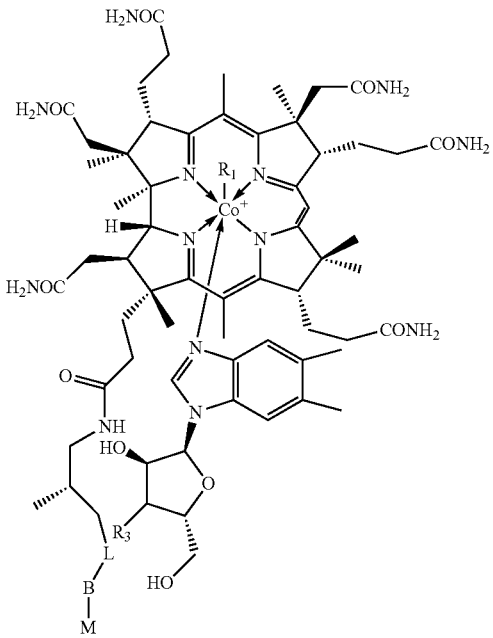

where $R_1$ can be 5'-deoxyadenosyl, $CH_3$, OH, or CN; $R_3$ can be OH or H; L is a linker, B is a saccharide-based structure, and M is a metal complexed with the saccharide-based structure. In an illustrative embodiment, L can be a hydrazone linker and M can be Fe. In embodiments, B can include 10-16 carbon atoms, 9-15 oxygen atoms, and 16-28 hydrogen atoms. In particular embodiments, B can be derived from sucrose.

Other example structures having a linkage between a saccharide-metal complex and a derivative of vitamin B12 can have the following form:

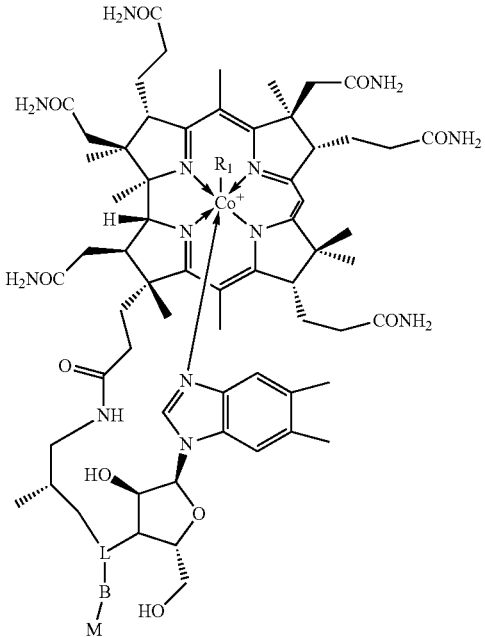

where $R_1$ can be 5'-deoxyadenosyl, $CH_3$, OH, or CN; L is a linker, B is a saccharide-based structure, and M is a metal complexed with the saccharide-based structure. In illustrative embodiments, L can be a hydrazone linker and M can be Fe. In embodiments, B can include 10-16 carbon atoms, 9-15 oxygen atoms, and 16-28 hydrogen atoms. In particular embodiments, B can be derived from sucrose.

Example structures having a linkage between multiple saccharide-metal complexes and a derivative of vitamin B12 can have the following form:

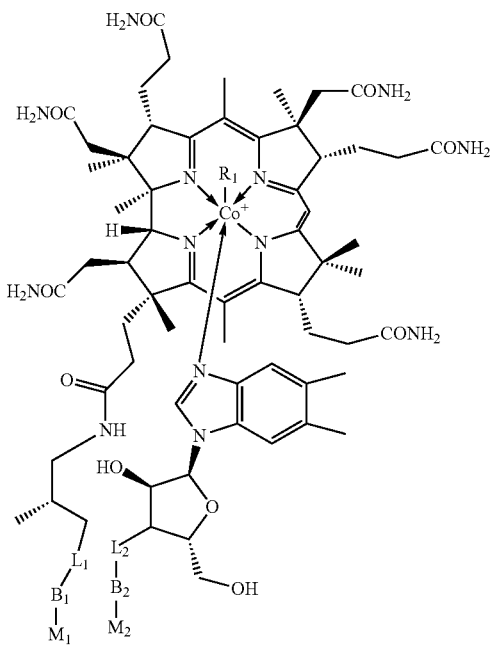

where $R_1$ can be 5'-deoxyadenosyl, $CH_3$, OH, or CN; $L_1$ is a first linker, $L_2$ is a second linker, $B_1$ is a first saccharide-based structure, $B_2$ is a second saccharide-based structure, $M_1$ is a first metal, and $M_2$ is a second metal complexed with the saccharide-based structure. In illustrative embodiments, $L_1$ and $L_2$ can be hydrazone linkers and $M_1$ and $M_2$ can be Fe. In embodiments, $B_1$ and $B_2$ can include 10-16 carbon atoms, 9-15 oxygen atoms, and 16-28 hydrogen atoms. In particular embodiments, $B_1$ and $B_2$ can be derived from sucrose.

In embodiments, a saccharide-metal complex can be derived from a disaccharide. For example a saccharide-metal complex can be derived from sucrose. In other examples, a saccharide-metal complex can be derived from lactose. Example structures of a saccharide-metal complex can have the following form:

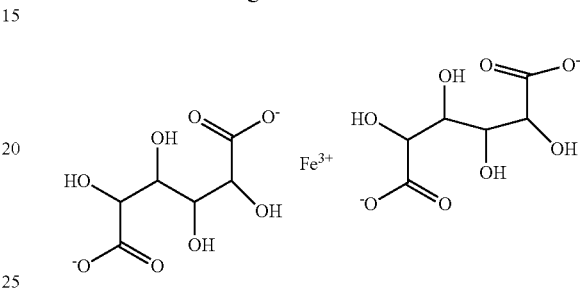

It is to be understood that although the above structure indicates a single Fe atom complexed with a sucrose derived compound, one or more Fe atoms can be complexed with one or more repeating units of the sucrose derived compound to balance the charges of the groups as needed.

Compositions. Heme proteins (including modifications, variants and D-substituted analogs thereof), heme protein degradation inhibitors (e.g., HO-1 inhibitors, protoporphyrins, hemin and/or hematin), iron and vitamin B12 (individually and collectively, "active ingredients") can be provided alone or in combination within a composition. In particular embodiments, composition includes at least one heme protein and/or at least one heme protein degradation inhibitor and at least one pharmaceutically acceptable carrier. Salts and/or pro-drugs of active ingredients can also be used.

A pharmaceutically acceptable salt includes any salt that retains the activity of the active ingredient and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes an active ingredient which is converted to a therapeutically active compound after administration, such as by cleavage of a protein or by hydrolysis of a biologically labile group.

In some embodiments, the compositions include active ingredients of at least 0.1% w/v of the composition; at least 1% w/v of composition; at least 10% w/v of composition; at least 20% w/v of composition; at least 30% w/v of composition; at least 40% w/v of composition; at least 50% w/v of composition; at least 60% w/v of composition; at least 70% w/v of composition; at least 80% w/v of composition; at least 90% w/v of composition; at least 95% w/v of composition; or at least 99% w/v of composition.

In other embodiments, active ingredients can be provided as part of a composition that can include, for example, at least 0.1% w/w of composition; at least 1% w/w of composition; at least 10% w/w of composition; at least 20% w/w of composition; at least 30% w/w of composition; at least 40% w/w of composition; at least 50% w/w of composition; at least 60% w/w of composition; at least 70% w/w of composition; at least 80% w/w of composition; at least 90% w/w of composition; at least 95% w/w of composition; or at least 99% w/w of composition.

Particular embodiments include a nitrited heme protein degradation inhibitor with a nitrited heme protein. Particular embodiments include a nitrited protoporphyrin with a nitrited heme protein. Particular embodiments include a nitrited metal protoporphyrin with a nitrited heme protein. Particular embodiments include a nitrited SnPP with a nitriated heme protein. Particular embodiments include a nitrited hemin with a nitrited heme protein. Particular embodiments include a nitrited hematin with a nitrited heme protein. In particular forms of these exemplary embodiments, the nitrited heme protein is myoglobin. Particular embodiments also include more than one nitrited heme protein degradation inhibitor (e.g. a nitrited protoporphyrin, nitrited hemin and/or nitrited hematin) with a heme protein (e.g., myoglobin or nitrited myoglobin). In further particular embodiments, a combination of heme protein degradation inhibitor is provided wherein not all constituents of the combination are nitrited.

Particular embodiments include iron, optionally in combination with a metal protoporphyrin, SnPP and/or vitamin B12. The iron can be iron sucrose. These embodiments can additionally include heme proteins (e.g., myoglobin or nitrited myoglobin) and/or heme protein degradation inhibitor (e.g., protoporphyrins, hemin and/or hematin and/or their nitrated forms). When embodiments utilize iron in combination with vitamin B12, the iron and B12 can be complexed or cross-linked into a single unit.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA.

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the active ingredient or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on active ingredient weight.

The compositions disclosed herein can be formulated for administration by, for example, injection, inhalation, infusion, perfusion, lavage, or ingestion. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, intrathecal, intratumoral, intramuscular, intravesicular, and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Alternatively, the formulation can be in lyophilized and/or powder form for constitution with a suitable vehicle, e.g., sterile pyrogen-free water, before use. Particular embodiments are formulated for intravenous administration.

For oral administration, the compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated as an aerosol. In one embodiment, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated containing a powder mix of heme protein and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days. Depot preparations can be administered by injection; parenteral injection; instillation; or implantation into soft tissues, a body cavity, or occasionally into a blood vessel with injection through fine needles.

Depot formulations can include a variety of bioerodible polymers including poly(lactide), poly(glycolide), poly(caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Del.), poly(vinyl alcohol) (PVA), Brij® (Croda Americas, Wilmington, Del.), sucrose acetate isobutyrate (SAIB), salts, and buffers.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Kits.

Also disclosed herein are kits including one or more containers including one or more of the active ingredients and/or compositions described herein. In various embodiments, the kits may include one or more containers containing one or more active ingredients and/or compositions to be used in combination with the active ingredients and/or compositions described herein. Associated with such container(s) can be a notice in the form prescribed by a governmental agency regulating the manufacture, use, or sale of pharmaceuticals or biological products, which notice reflects approval by the agency of manufacture, use, or sale for human administration.

Optionally, the kits described herein further include instructions for using the kit in the methods disclosed herein. In various embodiments, the kit may include instructions regarding preparation of the active ingredients and/or compositions for administration; administration of the active ingredients and/or compositions; appropriate reference levels to interpret results associated with using the kit; proper disposal of the related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. The instructions may be in English and/or in any national or regional language. In various embodiments, possible side effects and contraindications to further use of components of the kit based on a subject's symptoms can be included. The kits and instructions can also be tailored according to the type of organ to be protected and the type of insult the organ may encounter.

In various embodiments, the packaging, active ingredients and/or compositions, and instructions are combined into a small, compact kit with printed instructions for use of each of the active ingredients and/or compositions. In various embodiments in which more than one active ingredient and/or composition is provided, the sequencing of use of the active ingredients and/or compositions can be labeled in the kit.

In various embodiments, the kits described herein include some or all of the necessary medical supplies needed to use the kit effectively, thereby eliminating the need to locate and gather such medical supplies. Such medical supplies can include syringes, ampules, tubing, facemask, a needleless fluid transfer device, an injection cap, sponges, sterile adhesive strips, Chloraprep, gloves, and the like. Variations in contents of any of the kits described herein can be made. Particular kits provide materials to administer compositions through intravenous administration.

Methods of Use.

As stated, the compositions, kits, and methods disclosed herein can be used to protect organs from injury by inducing acquired cytoresistance in the absence of an injury. There are numerous potential uses for the compositions, kits, and methods, some of which are described herein.

Methods disclosed herein include treating organs with active ingredients disclosed herein including salts and prodrugs thereof. Treating organs includes delivering therapeutically effective amounts. Therapeutically effective amounts include those that provide effective amounts, prophylactic treatments, and/or therapeutic treatments.

An organ is a part of a subject that is typically self-contained and has a specific vital function. Examples of organs include the heart, liver, kidneys, spleen, pancreas, brain, lungs, intestines, stomach, etc. In particular embodiments, therapeutically effective amounts can be administered directly to organs.

Therapeutically effective amounts can also be administered to organs by administering the therapeutically effective amount to the subject in which the organ resides. Subjects include humans, veterinary animals (dogs, cats, reptiles, birds, etc.), livestock (horses, cattle, goats, pigs, chickens, etc.), and research animals (monkeys, rats, mice, fish, etc.). Treating subjects includes delivering therapeutically effective amounts. Thus, unless stated otherwise, administration to an organ can be by administration to a subject, resulting in physiological delivery to the organ or can be by administration directly to the organ.

An "effective amount" is the amount of an active ingredient or composition necessary to result in a desired physiological change in an organ or subject. Effective amounts are often administered for research purposes. Effective amounts disclosed herein protect organs from injury by inducing acquired cytoresistance in the absence of an injury.

A "prophylactic treatment" includes a treatment administered to an organ that does not display signs or symptoms of organ injury or displays only early signs or symptoms of organ injury such that treatment is administered for the purpose of diminishing, preventing, or decreasing the risk of developing further organ injury. Thus, a prophylactic treatment functions as a preventative treatment against organ injury.

A "therapeutic treatment" includes a treatment administered to an organ that displays symptoms or signs of organ injury and is administered to the organ for the purpose of reducing the worsening of organ injury.

The actual dose amount administered to a particular organ (or subject) can be determined by a physician, veterinarian, or researcher taking into account parameters such as physical and physiological factors including target; body weight; severity of condition; upcoming insult, when known; type of organ requiring protection; previous or concurrent therapeutic interventions; idiopathy of the subject; and route of administration.

The amount and concentration of active ingredient in a composition, as well as the quantity of the composition administered, can be selected based on clinically relevant factors, the solubility of the active ingredient in the composition, the potency and activity of the active ingredient, and the manner of administration of the composition, as well as whether the active ingredient is modified (e.g., nitrited, PEGylated) or administered in combination with a heme protein degradation inhibitor (e.g., an HO-1 inhibitor) among other considerations.

A composition including a therapeutically effective amount of an active ingredient(s) disclosed herein can be administered intravenously to a subject for protection of organs in a clinically safe and effective manner, including one or more separate administrations of the composition. For example, 0.05 mg/kg to 5.0 mg/kg can be administered to a subject per day in one or more doses (e.g., doses of 0.05 mg/kg QD, 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg BID, 1.5 mg/kg BID, or 2.0 mg/kg BID). For certain organs and indications, the total daily dose of an active ingredient can be 0.05 mg/kg to 3.0 mg/kg administered intravenously to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of composition using 60-minute QD, BID, or TID intravenous infusion dosing. In one particular example, compositions can be intravenously administered QD or BID to a subject with, e.g., total daily doses of 1.5 mg/kg, 3.0 mg/kg, 4.0 mg/kg of a composition with up to 92-98% wt/wt of a heme protein.

Additional useful doses can often range from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg, or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

Each of the described doses of active ingredients can be a heme protein alone, heme proteins in combination, a heme protein degradation inhibitor alone, heme protein degradation inhibitors in combination or a combination of one or more heme proteins and one or more heme protein degradation inhibitors, iron, and/or vitamin B12. In particular embodiments, when included in combinations to produce a dose, such as a dose stated herein, the substituents in the combination can be provided in exemplary ratios such as: 1:1; 1:1.25; 1:1.5; 1:1.75; 1:8; 1:1.2; 1:1.25; 1:1.3; 1:1.35; 1:1.4; 1:1.5; 1:1.75; 1:2; 1:3; 1:4; 1:5; 1:6; 1:7; 1:8; 1:9; 1:10; 1:15; 1:20; 1:30; 1:40; 1:50; 1:60; 1:70; 1:80; 1:90; 1:100; 1:200; 1:300; 1:400; 1:500; 1:600; 1:700; 1:800; 1:900; 1:1000; 1:1:1; 1:2:1; 1:3:1; 1:4:1; 1:5; 1; 1:10:1; 1:2:2; 1:2:3; 1:3:4; 1:4:2; 1:5; 3; 1:10:20; 1:2:1:2; 1:4:1:3; 1:100:1:1000; 1:25:30:10; 1:4:16:3; 1:1000:5:15; 1:2:3:10; 1:5:15:45; 1:50:90:135; 1:1.5:1.8:2.3; 1:10:100:1000 or additional beneficial ratios depending on the number and identity of substituents in a combination to reach the stated dosage. The substituents in a combination can be provided within the same composition or within different compositions.

Therapeutically effective amounts can be achieved by administering single or multiple doses during the course of a treatment regimen (e.g., QID, TID, BID, daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly).

In particular embodiments, compositions are administered within 48 hours of an upcoming insult, within 46 hours of an upcoming insult, within 44 hours of an upcoming insult, within 42 hours of an upcoming insult, within 40 hours of an upcoming insult, within 38 hours of an upcoming insult, within 36 hours of an upcoming insult, within 34 hours of an upcoming insult, within 32 hours of an upcoming insult, within 30 hours of an upcoming insult, within 28 hours of an upcoming insult, within 26 hours of an upcoming insult, within 24 hours of an upcoming insult, within 22 hours of an upcoming insult, within 20 hours of an upcoming insult, within 18 hours of an upcoming insult, within 16 hours of an upcoming insult, within 14 hours of an upcoming insult, within 12 hours of an upcoming insult, within 10 hours of an upcoming insult, within 8 hours of an upcoming insult, within 6 hours of an upcoming insult, within 4 hours of an upcoming insult, or within 2 hours of an upcoming insult. In one particular embodiment, compositions are administered within 18 hours of an upcoming insult.

In additional particular embodiments, compositions are administered at least 48 hours before an upcoming insult, at least 46 hours before an upcoming insult, at least 44 hours before an upcoming insult, at least 42 hours before an upcoming insult, at least 40 hours before an upcoming insult, at least 38 hours before an upcoming insult, at least 36 hours before an upcoming insult, at least 34 hours before an upcoming insult, at least 32 hours before an upcoming insult, at least 30 hours before an upcoming insult, at least 28 hours before an upcoming insult, at least 26 hours before an upcoming insult, at least 24 hours before an upcoming insult, at least 22 hours before an upcoming insult, at least 20 hours before an upcoming insult, at least 18 hours before an upcoming insult, at least 16 hours before an upcoming insult, at least 14 hours before an upcoming insult, at least 12 hours before an upcoming insult, at least 10 hours before an upcoming insult, at least 8 hours before an upcoming insult, at least 6 hours before an upcoming insult, at least 4 hours before an upcoming insult, or at least 2 hours before an upcoming insult. In one particular embodiment, compositions are administered at least 18 hours before an upcoming insult.

Transplant Protection. In particular embodiments, organs are protected from injury during transplant. The compositions can be administered (i) to an organ donor before organ isolation from the donor; (ii) to the isolated organ before transplantation, and/or (iii) to the organ transplant recipient. This method of use can apply to any organ capable of transplant from one individual subject to a second individual subject. In particular embodiments, therapeutically effective amounts can be delivered directly to an organ following removal from a subject or prior to implantation in a second subject.

Renal System Protection. Until the current disclosure, there were no agents able to prevent or mitigate the occurrence of AKI in patients at high risk, such as individuals undergoing surgery, cardiopulmonary bypass, or radiocontrast toxicity. It is noteworthy that acute kidney failure is a major risk factor for both morbidity and mortality as well as the need for long term kidney dialysis. The latter costs the Federal Government billions of dollars in its end stage kidney disease/Medicare program. Thus, prevention of AKI/acute kidney failure presented a critical and completely unmet clinical need.

"Acute kidney injury", (AKI) also known as "acute renal failure" (ARF) or "acute kidney failure", refers to a disease or condition where a rapid loss of renal function occurs due to damage to the kidneys, resulting in retention of nitrogenous (urea and creatinine) and non-nitrogenous waste products that are normally excreted by the kidney. Depending on the severity and duration of the renal dysfunction, this accumulation is accompanied by metabolic disturbances, such as metabolic acidosis (acidification of the blood) and hyperkalaemia (elevated potassium levels), changes in body fluid balance, effects on many other organ systems/organ system failure, intravascular volume overload, coma and death. It can be characterized by oliguria or anuria (decrease or cessation of urine production), although nonoliguric ARF may occur. AKI is a serious complication in hospitals, resulting in a prolonged hospital stay and high mortality. Cardiac disease and cardiac surgery are both common causes of AKI. Once patients have AKI, the mortality thereof is high.

AKI may be a consequence of various causes including a) pre-renal (causes in the blood supply), which includes, hypovolemia or decreased blood volume, usually from shock or dehydration and fluid loss or excessive diuretics use; hepatorenal syndrome, in which renal perfusion is compromised due to liver failure; vascular problems, such as atheroembolic disease and renal vein thrombosis, which can occur as a complication of nephrotic syndrome; infection, usually sepsis, and systemic inflammation due to infection; severe burns; sequestration due to pericarditis and pancreatitis; and hypotension due to antihypertensives and vasodilators; b) intrinsic renal damage, which includes renal ischemia (transient blood flow reductions or interruption) toxins or medication (e.g. some NSAIDs, aminoglycoside antibiotics, iodinated contrast, lithium, phosphate nephropathy due to bowel preparation for colonoscopy with sodium phosphates); rhabdomyolysis or breakdown of muscle tissue, where the resultant release of myoglobin in the blood affects the kidney, which can also be caused by injury (especially crush injury or extensive blunt trauma), statins, stimulants and some other drugs; hemolysis or breakdown of red blood cells, which can be caused by various conditions such as sickle-cell disease, and lupus erythematosus; multiple myeloma, either due to hypercalcemia or "cast nephropathy"; acute glomerulonephritis which may be due to a variety of causes, such as anti-glomerular basement membrane disease/Goodpasture's syndrome, Wegener's granulomatosis, or acute lupus nephritis with systemic lupus erythematosus; and c) post-renal causes (obstructive causes in the urinary tract) which include, medication interfering with normal bladder emptying (e.g. anticholinergics); benign prostatic hypertrophy or prostate cancer; kidney stones; abdominal malignancy (e.g. ovarian cancer, colorectal cancer); obstructed urinary catheter; or drugs that can cause crystalluria and drugs that can lead to myoglobinuria & cystitis.

Methods of the current disclosure include protecting the kidney by inducing acquired cytoresistance. As stated, appropriate therapeutically effective amounts can initially be determined using animal models to identify dose ranges. Particular exemplary therapeutically effective amounts of active ingredient include 10 mg/kg; 20 mg/kg; 30 mg/kg; 40 mg/kg; 50 mg/kg; 60 mg/kg; 70 mg/kg; 80 mg/kg; 90 mg/kg, and 100 mg/kg.

Exemplary animal models of kidney injury include: glycerol-induced renal failure (mimics rhabdomyolysis); ischemia-reperfusion-induced ARF (simulates the changes induced by reduced kidney blood flow, resulting in tissue ischemia and cell tubule cell death); drug-induced models such as gentamicin, cisplatin, NSAID, ifosfamide-induced ARF (mimics the renal failure due to clinical administration of respective drugs); uranium, potassium dichromate-induced ARF (mimics the occupational hazard); S-(1,2-dichlorovinyl)-L-cysteine-induced ARF (simulates contaminated water-induced renal dysfunction); sepsis-induced ARF (mimics the infection-induced renal failure); and radiocontrast-induced ARF (mimics renal failure in patients during use of radiocontrast media at the time of cardiac catheterization). For more information regarding these models, see Singh et al., Pharmacol. Rep. 2012, 64(1): 31-44.

Known tests of kidney function include ultrasound; CT scan; and measuring lactate dehydrogenase (LDH), blood urea nitrogen (BUN), creatinine, creatinine clearance, iothalamate clearance, glomerular filtration rate, and inulin clearance.

Hepatic Protection. Exemplary animal models of liver injury include: ischemic reperfusion injury; chemically-induced liver fibrosis using hepatotoxins (carbon tetrachloride, thioacetamide, dimethyl, or diethyl nitrosamine); bile duct ligation; the Schistosomiasis model; the Concanavalin A hepatitis model; inducible HCV transgenic mice; various genetic models; the Enteral ethanol infusion model (Tsukamoto-French model); and the methionine and choline deficiency model.

Further, a number of hepatotoxic compounds, including certain therapeutics, induce cytotoxicity. Hepatotoxic compounds can produce liver cytotoxicity by direct chemical attack or by the production of a toxic metabolite. Cytotoxicity can be induced by direct chemical attack using the following drugs: Anesthetics, such as, Enflurane, Fluroxene, Halothane, and Methoxyflurane; Neuropsychotropics, such as, Cocaine, Hydrazides, Methylphenidate, and Tricyclics; Anticonvulsants, such as, Phenyloin and Valproic acid; Analgesics, such as, Acetaminophen, Chlorzoxazone, Dantrolene, Diclofenac, Ibuprofen, Indomethacin, Salicylates, Tolmetin, and Zoxazolamine; Hormones, such as, Acetohexamide, Carbutamide, Glipizide, Metahexamide, Propylthiouracil, Tamoxifen, Diethylstilbestrol; Antimicrobials, such as, Amphotericin B, Clindamycin, Ketoconazole, Mebendazole, Metronidazole, Oxacillin, Paraaminosalicylic acid, Penicillin, Rifampicin, Sulfonamides, Tetracycline, and Zidovudine; Cardiovascular drugs, such as, Amiodarone, Dilitiazem, a-Methyldopa, Mexiletine, Hydrazaline, Nicotinic acid, Papaverine, Perhexiline, Procainamide, Quinidine, and Tocainamide; and Immunosuppressives and Antineoplastics, such as, Asparaginase, Cisplatin, Cyclophosphamide, Dacarbazine, Doxorubicin, Fluorouracil, Methotrexate, Mithramycin, 6-MP, Nitrosoureas, Tamoxifen, Thioguanine, and Vincristine; and Miscellaneous drugs, such as, Disulfiram, Iodide ion, Oxyphenisatin, Vitamin A, and Paraaminobenzoic acid.

Hepatotoxic compounds inducing cholestasis, an arrest in the flow of bile, may take several forms. Centribular cholestasis is accompanied by portal inflammatory changes. Bile duct changes have been reported with some drugs such as erythromycin, while pure canalicular cholestasis is characteristic of other drugs such as the anabolic steroids. Chronic cholestasis has been linked to such drugs as methyltestosterone and estradiol. Cholestatic disease can be induced using hepatotoxic compounds including the following: contraceptive steroids, androgenic steroids, anabolic steroids, Acetylsalicylic acid, Azathioprine, Benzodiazepine, Chenodeoxycholic acid, Chlordiazepoxide, Erythromycin estolate, Fluphenazine, Furosemide, Griseofulvin, Haloperidol, Imipramine, 6-Mercaptopurine, Methimazole, Methotrexate, Methyldopa, Methylenediamine, Methyltestosterone, Naproxen, Nitrofurantoin, Penicillamine, Perphenazine, Prochlorperazine, Promazine, Thiobendazole, Thioridazine, Tolbutamide, Trimethoprimsulfamethoxazole, Arsenic, Copper, and Paraquat.

Some drugs, although primarily cholestatic, can also produce hepatoxicity, and therefore the liver injury they cause is mixed. Drugs causing mixed liver injury include, for example, the following: Chlorpromazine, Phenylbutazone, Halothane, Chlordiazepoxide, Diazepam, Allopurinol, Phenobarbital, Naproxen, Propylthiouracil, Chloramphenicol, Trimethoprimsulfamethoxazxole, Aminone, Disopyramide, Azathioprine, Cimetidine, and Ranitidine.

Detection of one or more enzymes of the arginine/urea/NO cycle, sulfuration enzymes, and/or spectrin breakdown related products is diagnostic of liver injury. Examples of these markers include: argininosuccinate synthetase (ASS) and argininosuccinate lyase (ASL), sulfuration (estrogen sulfotransferase (EST)), squalene synthase (SQS), liver glycogen phosphorylase (GP), carbamoyl-phosphate synthetase (CPS-1), α-enolase 1, glucose-regulated protein (GRP), and spectrin breakdown products.

In other embodiments, the detection of biomarkers as a diagnostic of liver injury, such as injury due to ischemia, can be correlated with existing tests. These can include: alkaline phosphatase (AP); 5'-nucleotidase (5'-ND); a-glutamyl transpeptidase (G-GT); leucine aminopeptidase (LAP); aspartate transaminase (AST); alanine transaminase (ALT); fructose-1,6-diphosphate aldolase (ALD); LDH; isocitrate dehydrogenase (ICDH); ornithine-carbamoyltransferase (OCT); sorbitol dehydrogenase (SDH) arginase; guanase; creatine phosphokinase (CPK); cholinesterase (ChE); procollagen type III peptide levels (PIIIP); ammonia blood levels in hepatoencephalopathies; ligand in levels in necrosis and hepatoma; hyaluronate levels due to hepatic endothelial cell damage; α-1-fetoprotein (AFP) levels to detect hepatoma; carcinoembryonic antigen (CEA) levels to detect cancer metastasis to the liver; elevations of antibodies against a variety of cellular components, such as, mitochondrial, and nuclear and specific liver membrane protein; and detection of proteins, such as, albumin, globin, amino acids, cholesterol, and other lipids. Also, biochemical analysis of a variety of minerals, metabolites, and enzymes obtained from liver biopsies can be useful in identifying further biomarkers in inherited, acquired, and experimentally induced liver disorders.

In other embodiments, the amount of detected biomarkers can be correlated to liver function tests to further assess liver injury. As is understood by one of skill in the art, liver function tests include the following: assessment of hepatic clearance of organic anions, such as, bilirubin, indocyanine green (ICG), sulfobromophthalein (BSP) and bile acids; assessment of hepatic blood flow by measurements of galactose and ICG clearance; and assessment of hepatic microsomal function, through the use of the aminopyrine breath test and caffeine clearance test. For example, serum bilirubin can be measured to confirm the presence and severity of jaundice and to determine the extent of hyperbilirubinemia, as seen in parenchymal liver disease. Aminotransferase (transaminase) elevations reflect the severity of active hepatocellular damage, while alkaline phosphatase elevations are found with cholestasis and hepatic infiltrates (Isselbacher, K. and Podolsky, D. in Hartison's Principles of Internal Medicine, 12th edition. Wilson et al. eds., 2: 1301-1308 (1991)).

Additional scoring systems and parameters used to assess liver function include the Child-Pugh scoring system as follows:

| Child-Pugh scoring system | | | |
|---|---|---|---|
| Measure | 1 point | 2 points | 3 points |
| Bilirubin (total) µmol/l (mg/dl) | <34 (<2) | 34-50 (2-3) | >50 (>3) |
| Serum albumin g/l | >35 | 28-35 | <28 |
| INR | <1.7 | 1.71-2.20 | >2.20 |

Child-Pugh scoring system

| Measure | 1 point | 2 points | 3 points |
|---|---|---|---|
| Ascites | None | Mild | Severe |
| Hepatic encephalopathy | None | Grade I-II (or suppressed with medication) | Grade III-IV (or refractory) |

The indocyanine plasma clearance test using a fingertip light sensor can be used as well as a postoperative liver function scoring system developed by Schindl et al (Schindl M et al. 2005, Archives of Surgery 140(2):183-189). This system grades liver dysfunction according to the levels of lactic acid, total bilirubin, INR, and encephalopathy postoperatively. Total scores of 0, 1-2, 3-4, or >4 are used to classify liver dysfunction as absent, mild, moderate, or severe, respectively. Further, the bile salt to phospholipid ratio can be evaluated.

Cardiac Protection. Exemplary animal models of cardiac injury include: myocardial infarction (MI) models, post-MI remodeling models, gene therapy models, cell therapy models, transverse aortic constriction (TAC) models, acute ischemic stroke models, renal and limb ischemia models, the Langendorff perfusion model, and the doxorubicin-induced cardiomyopathy model. See also, for example, cardiac injury animal models practiced by the Cardiovascular Research Laboratory, Baltimore, Md.

Various methods of detecting cardiac injury may be used, including non-invasive imaging, such as Magnetic Resonance Imaging (MRI), ultrasound, X-ray Computed Tomography (CT), single photon emission computed tomography (SPECT) and/or positron emission tomography (PET). Additional measures can include echocardiography, electrocardiogram, Mikro-tip pressure catheter, telemetry, immunohistochemistry, and molecular biological studies. U.S. Patent No. 2002/0115936 describes a method and apparatus for assessment of cardiac function by monitoring movement of the trachea.

Known tests of cardiac function include measuring PDH levels, plasma lactate levels, and/or cardiac carbohydrate oxidation. Markers associated with non-ischemic heart injury include: Alpha-2-HS-glycoprotein precursor (e.g., SEQ ID NO:22); Asporin; ATP synthase subunit delta (mitochondrial); Blood vessel epicardial substance (e.g., SEQ ID NO:23); C6ORF142; Carbonic anhydrase 1; Carbonic anhydrase 3; Ceruloplasmin; Coagulation factor IX; Collagen alpha-3(VI) chain; Dermatopontin; EGF-containing fibulin-like extracellular matrix protein 1; Fibrinogen gamma chain; Fibulin-1; Fibulin-2; Heat shock protein HSP 90-beta (e.g., SEQ ID NO:24); Hemoglobin subunit alpha; Hemoglobin subunit beta; Ig alpha-1 chain C region; Ig alpha-2 chain C region; Ig gamma-2 chain C region; Ig lambda chain C regions; Ig mu chain C region; Latent-transforming growth factor β-binding protein 2; Microfibril-associated glycoprotein 4; Myosin-2; Serum amyloid A protein; Sorbin and SH3 domain-containing protein 2 (e.g., SEQ ID NO:25); and Sorbin and SH3 domain-containing protein 2 (e.g., SEQ ID NO:26).

Markers associated with ischemic heart injury include: Alpha-2-HS-glycoprotein precursor (e.g., SEQ ID NO:22); Alpha-2-macroglobulin; Carbonic anhydrase 1; Hemoglobin subunit alpha; Hemoglobin subunit beta; Ig alpha-1 chain C region; Ig alpha-2 chain C region; Ig mu chain C region; Leiomodin-1 (e.g., SEQ ID NO:27); Myosin regulatory light chain MRLC2 (e.g., SEQ ID NO:28); Nexilin (e.g., SEQ ID NO:29); Pyruvate dehydrogenase E1 component subunit a; serum amyloid A protein; and somatic form.

Pulmonary Protection. Animal models of lung injury, including acute lung injury include injury inducement by intratracheal instillation of endotoxin (LPS), mechanical ventilation, hypoxemia, live bacteria (E. coli), hyperoxia, bleomycin, oleic acid, cecal ligation and puncture, and acid aspiration. For more information regarding lung injury models, see Assay Depot, described as the World's Largest On-Line Marketplace for Pharmaceutical Research Services.

Symptoms of lung injury include labored, rapid breathing, low blood pressure, and shortness of breath. Any type of pulmonary function testing can be used.

Pulmonary function testing generally can be divided into three main areas. The first type of pulmonary testing is generally referred to as spirometry which provides measurements in terms of volume and breathing rates of different patient inspiratory and expirarory efforts. In addition, various flow rates at various stages of a test are also the type of data generated from spirometry testing. A second area of pulmonary testing is a set of procedures designed to determine the uniformity of the distribution of inspired air throughout the lungs of a patient. By virtue of such tests, pulmonary insufficiency can be determined even though the alveolor ventilation of a patient is normal. A third type of pulmonary testing concerns the ability of the lungs to diffuse inspired air through alveolar membranes and such tests provide an indication of the ability of the lung to arterialize venous blood by exchanging oxygen for carbon dioxide.

Breathing volume can be assessed using a volume flow-sensing device connected to a subject's airway (e.g. by use of a spirometer or tachymeter) or by measuring the mechanical excursions of the chest and abdominal walls. Techniques that rely on recordings of chest and abdominal wall movements that are either strain gauge based (recording of changes in body circumference length), or based on elastic inductive electrical conductor loops arranged around the chest and abdomen of the patient can also be used. Recordings of the inductance of the loops can then be used to estimate the magnitude of cross sectional area variations of the chest and abdominal compartments. U.S. Pat. No. 4,308,872 is an example of this self-inductance loop estimation technology. Such methods can be used for quantitative measurements of respiratory volumes after a calibration procedure.

In particular embodiments, tests of pulmonary function include measuring breathing volume, arterial blood gases, and/or the A-a $O_2$ gradient.

Protection Against Sepsis. Sepsis, or Systemic Inflammatory Response Syndrome (SIRS), is characterized by a whole-body inflammatory state with the presence of infection. Sepsis can lead to fever, rapid breathing and low blood pressure and can injure all organs including organs of the cardiovascular system, the immunological system and the endocrine system.

Animal models of sepsis include cecal ligation and puncture (CLP)-induced sepsis alone or in combination with instillation of bacteria (e.g., Pseudomonas aeruginosa or Streptococcus pneumoniae). Sepsis animal models also include intravenous or intraperitoneal administration of a toll-like receptor (TLR) agent such as lipopolysaccharide (LPS or endotoxin) or zymosan. Other sepsis models include ascending colon stent peritonitis and late-stage immunostimulatory models. For more information regarding sepsis models, see Assay Depot, described as the World's Largest On-Line Marketplace for Pharmaceutical Research Services.

Protection against sepsis can be confirmed by measuring blood pressure, blood gasses, cytokine measurements, and secondary organ function as described elsewhere herein (e.g., lung, liver, heart, kidney function).

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A kit for protecting a subject's organ(s) from injury, the kit including a therapeutically effective amount of myoglobin, iron, and/or vitamin B12 wherein administration of the therapeutically effective amount of myoglobin, iron, and/or vitamin B12 to the subject protects the subject's organ(s) from injury without causing organ injury.
2. A kit for protecting a subject's organ(s) from injury, the kit including a therapeutically effective amount of a heme protein, iron, and/or vitamin B12 wherein administration of the therapeutically effective amount of heme protein, iron, and/or vitamin B12 to the subject protects the subject's organ(s) from injury without causing organ injury.
3. A kit of embodiment 2 wherein the heme protein, iron, and/or vitamin B12 is formulated within a composition.
4. A kit of any one of embodiments 2 or 3 wherein the heme protein is a heme protein variant, a heme protein d-substituted analog, a heme protein modification, or combination thereof.
5. A kit of any one of embodiments 2-4 wherein the heme protein is a modified heme protein.
6. A kit of embodiment 5 wherein the modified heme protein is a nitrited heme protein or a PEGylated heme protein.
7. A kit of any one of embodiments 2-6 wherein the heme protein is myoglobin.
8. A kit of any one of embodiments 2-7 wherein the heme protein is a myoglobin variant and/or a myoglobin modification.
9. A kit of embodiment 8 wherein the modified myoglobin is a nitrited myoglobin or a PEGylated myoglobin.
10. A kit of any one of embodiments 2-9 further including a heme protein degradation inhibitor, optionally, a nitrited heme protein degradation inhibitor.
11. A kit of embodiment 10 wherein the heme protein degradation inhibitor is formulated within a composition.
12. A kit of any one of embodiments 10 or 11 wherein the heme protein degradation inhibitor and the heme protein, iron, and/or vitamin B12 are formulated within the same composition.
13. A kit of any one of embodiments 10-12 wherein the heme protein degradation inhibitor is a heme oxygenase inhibitor.
14. A kit of embodiment 13 wherein the heme oxygenase inhibitor is a protoporphyrin, hemin, and/or hematin, optionally, a nitrited protoporphyrin, hemin, and/or hematin.
15. A kit of any one of embodiments 13 or 14 wherein the heme oxygenase inhibitor is a metal protoporphyrin, optionally, a nitrited metal protoporphyrin.
16. A kit of embodiment 15 wherein the metal protoporphyrin is Sn-protoporphyrin.
17. A kit of any one of embodiments 2-16 further including administration instructions.
18. A kit of any one of embodiments 2-17 wherein absence of organ injury caused by the administration is confirmed by comparison to a reference level.
19. A kit of any one of embodiments 2-18 wherein protection is evidenced by comparison to a reference level.
20. A kit of any one of embodiments 18 or 19 wherein the reference level is provided within the kit.
21. A kit of any one of embodiments 2-20 wherein the organ is protected from an injury based on an insult.
22. A kit of embodiment 21 wherein the insult is scheduled.
23. A kit of embodiment 22 wherein the administration occurs at least 8 hours before the scheduled insult.
24. A kit of any one of embodiments 22 or 23 wherein the scheduled insult is surgery, induced cardiac/cerebral ischemic reperfusion, cardiovascular surgery, balloon angioplasty, chemotherapy, nephrotoxic drug administration, and/or radiocontrast toxicity.
25. A kit of embodiment 24 wherein the surgery is an organ transplant surgery.
26. A kit of embodiment 21 wherein the insult is sepsis.
27. A kit of any one of embodiments 2-26 wherein the organ is a transplanted organ.
28. A kit of any one of embodiments 2-27 wherein the organ is a heart, kidney, liver, or lung.
29. A kit of any one of embodiments 2-28 wherein the organ is a heart and protection is evidenced by improvement of cardiac function, and/or reduction in cardiac enzyme release.
30. A kit of embodiment 29 wherein the cardiac enzyme is troponin.
31. A kit of any one of embodiments 2-30 wherein the organ is a kidney and protection is evidenced by prevention or reduction in blood urea nitrogen (BUN) or serum creatinine increases.
32. A kit of any one of embodiments 2-31 wherein the organ is a liver and protection is evidenced by prevention or reduction in liver enzyme increases.
33. A kit of any one of embodiments 2-32 wherein the organ is a lung and protection is evidenced by reduction in blood gas deterioration, reduction in need for supplemental oxygen, and/or reduced ventilator requirements.
34. A kit for generating acquired cytoresistance in a subject's organ(s), the kit including a therapeutically effective amount of a heme protein, iron, and/or vitamin B12 wherein administration of the therapeutically effective amount of heme protein, iron, and/or vitamin B12 to the subject generates acquired cytoresistance in the subject's organ(s) without causing organ injury.
35. A kit of embodiment 34 wherein the heme protein, iron, and/or vitamin B12 is formulated within a composition.
36. A kit of any one of embodiments 34 or 35 wherein the heme protein is a heme protein variant, a heme protein d-substituted analog, a heme protein modification, or a combination thereof.
37. A kit of any one of embodiments 34-36 wherein the heme protein is a modified heme protein.
38. A kit of embodiment 37 wherein the modified heme protein is a nitrited heme protein or a PEGylated heme protein.
39. A kit of any one of embodiments 34-38 wherein the heme protein is myoglobin.
40. A kit of embodiment 34-39 wherein the heme protein is a myoglobin variant and/or a myoglobin modification.

41. A kit of embodiment 40 wherein the modified myoglobin is a nitrited myoglobin or a PEGylated myoglobin.
42. A kit of any one of embodiments 34-41 further including a heme protein degradation inhibitor, optionally a nitrited heme protein degradation inhibitor.
43. A kit of embodiment 42 wherein the heme protein degradation inhibitor is formulated within a composition.
44. A kit of any one of embodiments 42 or 43 wherein the heme protein degradation inhibitor and the heme protein are formulated within the same composition.
45. A kit of any one of embodiments 42-44 wherein the heme protein degradation inhibitor is a heme oxygenase inhibitor.
46. A kit of embodiment 45 wherein the heme oxygenase inhibitor is a protoporphyrin, hemin, and/or hematin, optionally a nitrited protoporphyrin, hemin, and/or hematin.
47. A kit of any one of embodiments 45 or 46 wherein the heme oxygenase inhibitor is a metal protoporphyrin.
48. A kit of embodiment 47 wherein the metal protoporphyrin is Sn-protoporphyrin.
49. A kit of any one of embodiments 34-48 further including administration instructions.
50. A kit of any one of embodiments 34-49 wherein absence of organ injury caused by the administration is confirmed by comparison to a reference level.
51. A kit of any one of embodiments 34-50 wherein the acquired cytoresistance protects the organ from an injury.
52. A kit of embodiment 51 wherein protection is evidenced by comparison to a reference level.
53. A kit of any one of embodiments 50 or 52 wherein the reference level is provided within the kit.
54. A kit of any one of embodiments 51-53 wherein the organ is protected from an injury based on an insult.
55. A kit of embodiment 54 wherein the insult is scheduled.
56. A kit of embodiment 55 wherein the administration occurs at least 8 hours before the scheduled insult.
57. A kit of any one of embodiments 55 or 56 wherein the scheduled insult is surgery, chemotherapy, or radiocontrast toxicity.
58. A kit of embodiment 57 wherein the surgery is an organ transplant surgery.
59. A kit of embodiment 54 wherein the insult is sepsis.
60. A kit of any one of embodiments 34-59 wherein the organ is a transplanted organ.
61. A kit of any one of embodiments 34-60 wherein the organ is a heart, kidney, liver, or lung.
62. A kit of any one of embodiments 51-61 wherein the organ is a heart and protection is evidenced by improvement of cardiac function, and/or reduction in cardiac enzyme release.
63. A kit of embodiment 62 wherein the cardiac enzyme is troponin.
64. A kit of any one of embodiments 51-63 wherein the organ is a kidney and protection is evidenced by prevention or reduction in BUN or serum creatinine increases.
65. A kit of any one of embodiments 51-64 wherein the organ is a liver and protection is evidenced by prevention or reduction in liver enzyme increases.
66. A kit of any one of embodiments 51-65 wherein the organ is a lung and protection is evidenced by reduction in blood gas deterioration, reduction in need for supplemental oxygen, and/or reduced ventilator requirements.
67. A kit for up-regulating expression of protective stress proteins in a subject's organ(s), the kit including a therapeutically effective amount of a heme protein, iron and/or vitamin B12 wherein administration of the therapeutically effective amount of heme protein, iron and/or vitamin B12 to the subject up-regulates expression of protective stress proteins in the subject's organ(s) without causing organ injury.
68. A kit of embodiment 67 wherein the heme protein, iron and/or vitamin B12 is formulated within a composition.
69. A kit of any one of embodiments 67 or 68 wherein the heme protein is a heme protein variant, a heme protein d-substituted analog, a heme protein modification, or a combination thereof.
70. A kit of any one of embodiments 67-69 wherein the heme protein a modified heme protein.
71. A kit of embodiment 70 wherein the modified heme protein is a nitrited heme protein or a PEGylated heme protein.
72. A kit of any one of embodiments 67-71 wherein the heme protein is myoglobin.
73. A kit of any one of embodiments 67-72 wherein the heme protein is a myoglobin variant and/or a myoglobin modification.
74. A kit of embodiment 73 wherein the modified myoglobin is a nitrited myoglobin or a PEGylated myoglobin.
75. A kit of any one of embodiments 67-74 wherein the protective stress proteins are selected from heme oxygenase, haptoglobin, hemopexin, hepcidin, alpha-1 antitrypsin, interleukin-10, heat-shock proteins, neutrophil gelatinase-associated lipocalin, and HMG CoA reductase.
76. A kit of any one of embodiments 67-75 further including a heme protein degradation inhibitor, optionally a nitrited heme protein degradation inhibitor.
77. A kit of embodiment 76 wherein the heme protein degradation inhibitor is formulated within a composition.
78. A kit of any one of embodiments 76 or 77 wherein the heme protein degradation inhibitor and the heme protein are formulated within the same composition.
79. A kit of any one of embodiments 76-78 wherein the heme protein degradation inhibitor is a heme oxygenase inhibitor.
80. A kit of embodiment 79 wherein the heme oxygenase inhibitor is a protoporphyrin, hemin, and/or hematin, optionally a nitrited protoporphyrin, hemin and/or hematin.
81. A kit of any one of embodiments 79 or 80 wherein the heme oxygenase inhibitor is a metal protoporphyrin.
82. A kit of embodiment 81 wherein the metal protoporphyrin is Sn-protoporphyrin.
83. A kit of any one of embodiments 67-82 further including administration instructions.
84. A kit of any one of embodiments 67-83 wherein absence of organ injury caused by the administration is confirmed by comparison to a reference level.
85. A kit of any one of embodiments 67-84 wherein the up-regulation of protective stress proteins protects the organ from an injury.
86. A kit of embodiment 85 wherein protection is evidenced by comparison to a reference level.
87. A kit of any one of embodiments 84 or 86 wherein the reference level is provided within the kit.
88. A kit of any one of embodiments 85-87 wherein the organ is protected from an injury based on an insult.
89. A kit of embodiment 88 wherein the insult is scheduled.
90. A kit of embodiment 89 wherein the administration occurs at least 8 hours before the scheduled insult.
91. A kit of any one of embodiments 89 or 90 wherein the scheduled insult is surgery, chemotherapy, or radiocontrast toxicity.

92. A kit of embodiment 91 wherein the surgery is an organ transplant surgery.
93. A kit of embodiment 88 wherein the insult is sepsis.
94. A kit of any one of embodiments 67-93 wherein the organ is a transplanted organ.
95. A kit of any one of embodiments 67-94 wherein the organ is a heart, kidney, liver, or lung.
96. A kit of any one of embodiments 85-95 wherein the organ is a heart and protection is evidenced by improvement of cardiac function, and/or reduction in cardiac enzyme release.
97. A kit of embodiment 96 wherein the cardiac enzyme is troponin.
98. A kit of any one of embodiments 85-97 wherein the organ is a kidney and protection is evidenced by prevention or reduction in BUN or serum creatinine increases.
99. A kit of any one of embodiments 85-98 wherein the organ is a liver and protection is evidenced by prevention or reduction in liver enzyme increases.
100. A kit of any one of embodiments 85-99 wherein the organ is a lung and protection is evidenced by reduction in blood gas deterioration, reduction in need for supplemental oxygen, and/or reduced ventilator requirements.
101. A composition including myoglobin, a myoglobin variant, a myoglobin d-substituted analog, a myoglobin modification, or a combination thereof, optionally iron and/or vitamin B12.
102. A composition of embodiment 101 wherein the myoglobin is a modified myoglobin.
103. A composition of embodiment 102 wherein the modified myoglobin is a nitrited myoglobin or a PEGylated myoglobin.
104. A composition of any one of embodiments 101-103 wherein the myoglobin is a myoglobin variant.
105. A composition of any one of embodiments 101-104 further including a heme protein degradation inhibitor, optionally a nitrited heme protein degradation inhibitor.
106. A composition of embodiment 105 wherein the heme protein degradation inhibitor is a heme oxygenase inhibitor.
107. A composition of embodiment 106 wherein the heme oxygenase inhibitor is a protoporphyrin, hemin, and/or hematin, optionally a nitrited protoporphyrin, hemin and/or hematin.
108. A composition of any one of embodiments 106 or 107 wherein the heme oxygenase inhibitor is a metal protoporphyrin.
109. A composition of embodiment 108 wherein the metal protoporphyrin is Sn-protoporphyrin.
110. A composition including a heme protein and a heme protein degradation inhibitor, optionally iron and/or vitamin B12.
111. A composition of embodiment 110 wherein the heme protein is a modified heme protein.
112. A composition of embodiment 111 wherein the modified heme protein is a nitrited heme protein or a PEGylated heme protein.
113. A composition of any one of embodiments 110-112 wherein the heme protein is myoglobin.
114. A composition of any one of embodiments 110-113 wherein the heme protein is a myoglobin variant and/or a myoglobin modification.
115. A composition of embodiment 114 wherein the modified myoglobin is a nitrited myoglobin or a PEGylated myoglobin.
116. A composition of any one of embodiments 110-115 wherein the heme protein degradation inhibitor is a heme oxygenase inhibitor.
117. A composition of embodiment 116 wherein the heme oxygenase inhibitor is a protoporphyrin, hemin, and/or hematin, optionally a nitrited protoporphyrin, hemin and/or hematin.
118. A composition of any one of embodiments 116 or 117 wherein the heme oxygenase inhibitor is a metal protoporphyrin.
119. A composition of embodiment 118 wherein the metal protoporphyrin is Sn-protoporphyrin.
120. A method of protecting a subject's organ(s) from injury including administering to the subject a therapeutically effective amount of a composition including a heme protein, iron and/or vitamin B12 before the injury to the organ occurs, wherein the administering protects the subject's organ(s) from the injury without causing organ injury.
121. A method of embodiment 120 wherein the composition includes a modified heme protein.
122. A method of embodiment 121 wherein the modified heme protein is a nitrited heme protein or a PEGylated heme protein.
123. A method of any one of embodiments 120-122 wherein the heme protein is myoglobin.
124. A method of any one of embodiments 120-123 wherein the heme protein is a myoglobin variant and/or a myoglobin modification.
125. A method of embodiment 124 wherein the modified myoglobin is a nitrited myoglobin or a PEGylated myoglobin
126. A method of any one of embodiments 120-125 wherein the composition further includes a heme protein degradation inhibitor, optionally a nitrited heme protein degradation inhibitor.
127. A method of any one of embodiments 120-126 further including administering to the subject a second composition including a heme protein degradation inhibitor, optionally a nitrited heme protein degradation inhibitor.
128. A method of any one of embodiments 126 or 127 wherein the heme protein degradation inhibitor is a heme oxygenase inhibitor.
129. A method of embodiment 128 wherein the heme oxygenase inhibitor is a protoporphyrin, hemin, and/or hematin, optionally a nitrited protoporphyrin, hemin and/or hematin.
130. A method of any one of embodiments 128 or 129 wherein the heme oxygenase inhibitor is a metal protoporphyrin.
131. A method of embodiment 130 wherein the metal protoporphyrin is Sn-protoporphyrin.
132. A method of any one of embodiments 120-131 wherein absence of organ injury caused by the administration is confirmed by comparison to a reference level.
133. A method of any one of embodiments 120-132 wherein protection is evidenced by comparison to a reference level.
134. A method of any one of embodiments 120-133 wherein the injury is an injury based on an insult.
135. A method of embodiment 134 wherein the insult is scheduled.
136. A method of embodiment 135 wherein the administration occurs at least 8 hours before the scheduled insult.
137. A method of any one of embodiments 135 or 136 wherein the scheduled insult is surgery, chemotherapy, or radiocontrast toxicity.

138. A method of embodiment 137 wherein the surgery is an organ transplant surgery.
139. A method of embodiment 134 wherein the insult is sepsis.
140. A method of any one of embodiments 120-139 wherein the organ is a transplanted organ.
141. A method of any one of embodiments 120-140 wherein the organ is a heart, kidney, liver, or lung.
142. A method of any one of embodiments 120-141 wherein the organ is a heart and protection is evidenced by improvement of cardiac function, and/or reduction in cardiac enzyme release.
143. A method of embodiment 142 wherein the cardiac enzyme is troponin.
144. A method of any one of embodiments 120-143 wherein the organ is a kidney and protection is evidenced by prevention or reduction in BUN or serum creatinine increases.
145. A method of any one of embodiments 120-144 wherein the organ is a liver and protection is evidenced by prevention or reduction in liver enzyme increases.
146. A method of any one of embodiments 120-145 wherein the organ is a lung and protection is evidenced by reduction in blood gas deterioration, reduction in need for supplemental oxygen, and/or reduced ventilator requirements.
147. A method of generating acquired cytoresistance in a subject's organ(s) including administering to the subject a therapeutically effective amount of a composition including a heme protein, iron, and/or vitamin B12 wherein the administering generates acquired cytoresistance without causing organ injury.
148. A method of embodiment 147 wherein the composition includes a modified heme protein.
149. A method of embodiment 148 wherein the modified heme protein is a nitrited heme protein or a PEGylated heme protein.
150. A method of any one of embodiments 147-149 wherein the heme protein is myoglobin.
151. A method of any one of embodiments 147-150 wherein the heme protein is a myoglobin variant and/or a myoglobin modification.
152. A method of embodiment 151 wherein the modified myoglobin is a nitrited myoglobin or a PEGylated myoglobin.
153. A method of any one of embodiments 147-152 wherein the composition further includes a heme protein degradation inhibitor.
154. A method of any one of embodiments 147-153 further including administering to the subject a second composition including a heme protein degradation inhibitor, optionally a nitrited heme protein degradation inhibitor.
155. A method of any one of embodiments 153 or 154 wherein the heme protein degradation inhibitor is a heme oxygenase inhibitor.
156. A method of embodiment 155 wherein the heme oxygenase inhibitor is a protoporphyrin, hemin, and/or hematin, optionally nitrited protoporphyrin, hemin and/or hematin.
157. A method of any one of embodiments 155 or 156 wherein the heme oxygenase inhibitor is a metal protoporphyrin.
158. A method of embodiment 157 wherein the metal protoporphyrin is Sn-protoporphyrin.
159. A method of any one of embodiments 147-158 wherein absence of organ injury caused by the administration is confirmed by comparison to a reference level.
160. A method of any one of embodiments 147-159 wherein the acquired cytoresistance protects an organ from injury.
161. A method of embodiment 160 wherein the protection is evidenced by comparison to a reference level.
162. A method of any one of embodiments 160 or 161 wherein the injury is injury based on an insult.
163. A method of embodiment 162 wherein the insult is scheduled.
164. A method of embodiment 163 wherein the administration occurs at least 8 hours before the scheduled insult.
165. A method of any one of embodiments 163 or 164 wherein the scheduled insult is surgery, chemotherapy, or radiocontrast toxicity.
166. A method of embodiment 165 wherein the surgery is an organ transplant surgery.
167. A method of embodiment 162 wherein the insult is sepsis.
168. A method of any one of embodiments 147-167 wherein the organ is a transplanted organ.
169. A method of any one of embodiments 147-168 wherein the organ is a heart, kidney, liver, or lung.
170. A method of any one of embodiments 160-169 wherein the organ is a heart and protection is evidenced by improvement of cardiac function, and/or reduction in cardiac enzyme release.
171. A method of embodiment 170 wherein the cardiac enzyme is troponin.
172. A method of any one of embodiments 160-171 wherein the organ is a kidney and protection is evidenced by prevention or reduction in BUN or serum creatinine increases.
173. A method of any one of embodiments 160-172 wherein the organ is a liver and protection is evidenced by prevention or reduction in liver enzyme increases.
174. A method of any one of embodiments 160-173 wherein the organ is a lung and protection is evidenced by reduction in blood gas deterioration, reduction in need for supplemental oxygen, and/or reduced ventilator requirements.
175. A method of up-regulating expression of protective stress proteins in a subject's organ(s) including administering to the subject a therapeutically effective amount of a composition including a heme protein, iron and/or vitamin B12 wherein the administering up-regulates expression of protective stress proteins in the subject's organs without causing organ injury.
176. A method of embodiment 175 wherein the protective stress proteins are selected from heme oxygenase, haptoglobin, hemopexin, hepcidin, alpha-1 antitrypsin, interleukin-10, heat-shock proteins, neutrophil gelatinase-associated lipocalin, and/or HMG CoA reductase.
177. A method of any one of embodiments 175 or 176 wherein the composition includes a modified heme protein.
178. A method of embodiment 177 wherein the modified heme protein is a nitrited heme protein or a PEGylated heme protein.
179. A method of any one of embodiments 175-178 wherein the heme protein is myoglobin.
180. A method of any one of embodiments 175-179 wherein the heme protein is a myoglobin variant and/or a myoglobin modification.
181. A method of any one of embodiments 180 wherein the modified myoglobin is a nitrited myoglobin or a PEGylated myoglobin 182. A method of any one of embodiments 175-181 wherein the composition further includes a heme protein degradation inhibitor, optionally a nitrited heme protein degradation inhibitor.
183. A method of any one of embodiments 175-182 further including administering to the subject a second composition including a heme protein degradation inhibitor, optionally a nitrited heme protein degradation inhibitor.
184. A method of any one of embodiments 182 or 183 wherein the heme protein degradation inhibitor is a heme oxygenase inhibitor.
185. A method of embodiment 184 wherein the heme oxygenase inhibitor is a protoporphyrin, hemin, and/or hematin, optionally a nitrited protoporphyrin, hemin and/or hematin.
186. A method of any one of embodiments 184 or 185 wherein the heme oxygenase inhibitor is a metal protoporphyrin.
187. A method of embodiment 186 wherein the metal protoporphyrin is Sn-protoporphyrin.
188. A method of any one of embodiments 175-187 wherein absence of organ injury caused by the administration is confirmed by comparison to a reference level.
189. A method of any one of embodiments 175-188 wherein the up-regulated expression of protective stress proteins protects an organ from injury.
190. A method of embodiment 189 wherein protection is evidenced by comparison to a reference level.
191. A method of any one of embodiments 189 or 190 wherein the injury is an injury based on an insult.
192. A method of embodiment 191 wherein the insult is scheduled.
193. A method of embodiment 192 wherein the administration occurs at least 8 hours before the scheduled insult.
194. A method of any one of embodiments 192 or 193 wherein the scheduled insult is surgery, chemotherapy, or radiocontrast toxicity.
195. A method of embodiment 194 wherein the surgery is an organ transplant surgery.
196. A method of embodiment 191 wherein the insult is sepsis.
197. A method of any one of embodiments 175-196 wherein the organ is a transplanted organ.
198. A method of any one of embodiments 175-197 wherein the organ is a heart, kidney, liver, or lung.
199. A method of any one of embodiments 189-198 wherein the organ is a heart and protection is evidenced by improvement of cardiac function, and/or reduction in cardiac enzyme release.
200. A method of embodiment 199 wherein the cardiac enzyme is troponin.
201. A method of embodiment any one of embodiments 189-200 wherein the organ is a kidney and protection evidenced by prevention or reduction in BUN or serum creatinine increases.
202. A method of any one of embodiments 189-201 wherein the organ is a liver and protection evidenced by prevention or reduction in liver enzyme increases.
203. A method of any one of embodiments 189-202 wherein the organ is a lung and protection is evidenced by reduction in blood gas deterioration, reduction in need for supplemental oxygen, and/or reduced ventilator requirements.
204. An embodiment of any one of embodiments 1-203 wherein the composition is formulated for intravenous delivery, oral delivery, subcutaneous delivery, or intramuscular delivery.
205. An embodiment of any one of embodiments 1-204 wherein the composition is formulated within a slow-release depot.

206. A composition of matter comprising the structure

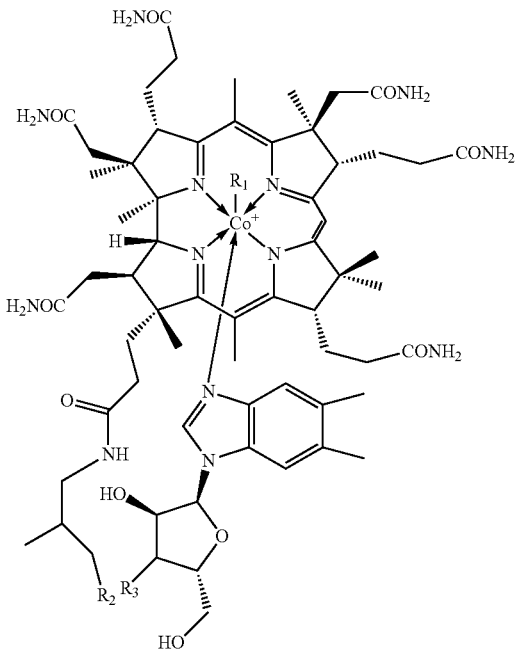

where $R_1$ is 5'-deoxyadenosyl, $CH_3$, OH, or CN; $R_2$ is OH or H; and $R_3$ is OH or H.

207. An embodiment of any one of embodiments 1-205, wherein the B12 has a structure

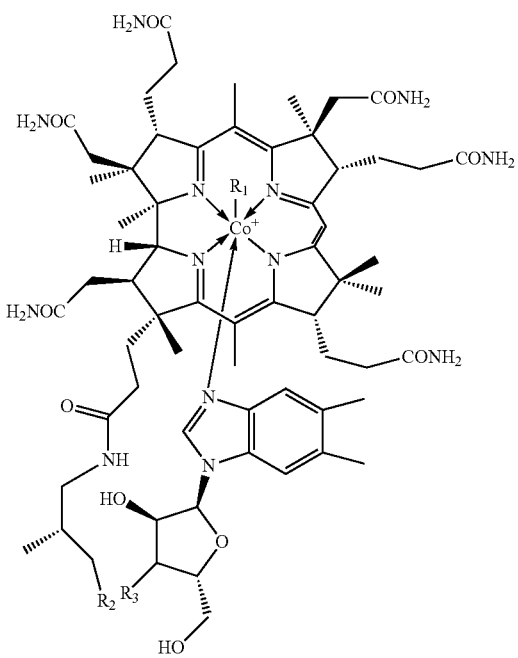

where $R_1$ is 5'-deoxyadenosyl, $CH_3$, OH, or CN; $R_2$ is OH or H; and $R_3$ is OH or H.

208. An embodiment of any of the proceeding embodiments wherein rather than administration to an organ through administration to a subject, administration is directly to an organ.

209. A composition of matter comprising the structure

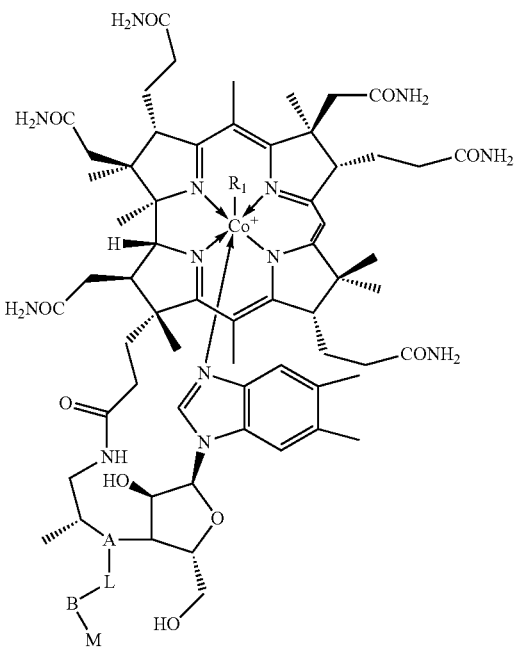

where $R_1$ is 5'-deoxyadenosyl, $CH_3$, OH, or CN; A is a phosphate group, L is a linker, B is a saccharide-based structure, and M is a metal complexed with the saccharide-based structure.

210. A composition of matter of embodiment 209, wherein A is $PO_4$, L is a hydrazone linker, B is a saccharide-based structure, and M is Fe.

211. A composition of matter of embodiment 209 or 210, wherein B has 10-16 carbon atoms, 9-15 oxygen atoms, and 16-28 hydrogen atoms.

212. A composition of matter of embodiment 209, 210, or 211, wherein B is derived from sucrose 213. A composition of matter comprising the structure

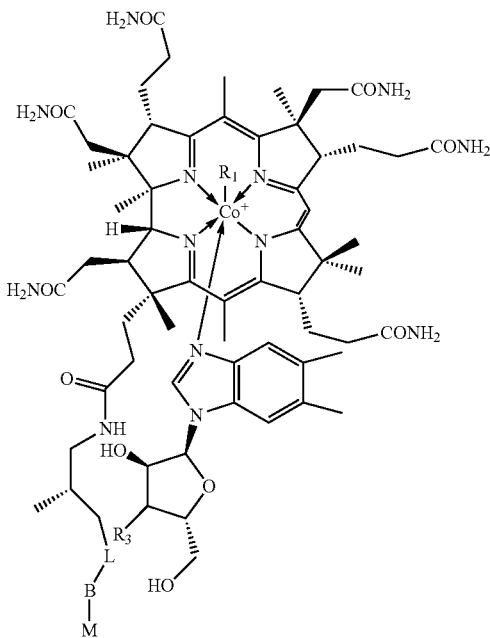

where $R_1$ is 5'-deoxyadenosyl, $CH_3$, OH, or CN; $R_3$ is OH or H; L is a linker, B is a saccharide-based structure, and M is a metal complexed with the saccharide-based structure.

214. A composition of matter of embodiment 213, wherein L is a hydrazone linker and M is Fe.

215. A composition of matter of embodiment 213, or 214, wherein B includes 10-16 carbon atoms, 9-15 oxygen atoms, and 16-28 hydrogen atoms.

216. A composition of matter of embodiment 213, 214, or 215, wherein B is derived from sucrose.

217. A composition of matter comprising the structure:

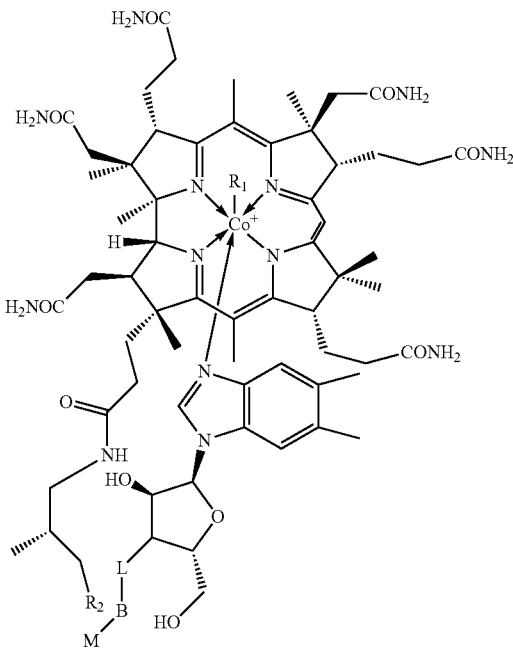

where $R_1$ is 5'-deoxyadenosyl, $CH_3$, OH, or CN; $R_3$ is OH or H; L is a linker, B is a saccharide-based structure, and M is a metal complexed with the saccharide-based structure.

218. A composition of matter of embodiment 217, wherein L is a hydrazone linker and M is Fe.

219. A composition of matter of embodiment 217 or 218, wherein B includes 10-16 carbon atoms, 9-15 oxygen atoms, and 16-28 hydrogen atoms.

220. A composition of matter of embodiment 217, 218, or 219, wherein B is derived from sucrose.

221. A composition of matter comprising the structure:

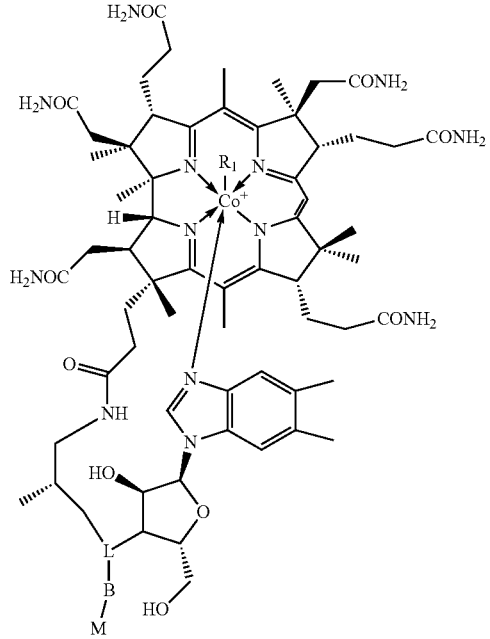

where $R_1$ is 5'-deoxyadenosyl, $CH_3$, OH, or CN; L is a linker, B is a saccharide-based structure, and M is a metal complexed with the saccharide-based structure.
222. A composition of matter of embodiment 221, wherein L is a hydrazone linker and M is Fe.
223. A composition of matter of embodiment 221 or 222, wherein B has 10-16 carbon atoms, 9-15 oxygen atoms, and 16-28 hydrogen atoms.
224. A composition of matter of embodiment 221, 222, or 223, wherein B is derived from sucrose.
225. A composition of matter comprising the structure:

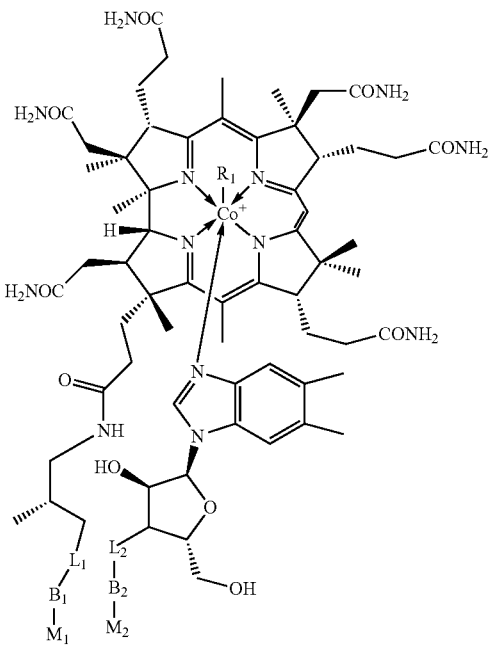

where $R_1$ is 5'-deoxyadenosyl, $CH_3$, OH, or CN; $L_1$ is a first linker, $L_2$ is a second linker, $B_1$ is a first saccharide-based structure, $B_2$ is a second saccharide-based structure, $M_1$ is a first metal, and $M_2$ is a second metal complexed with the saccharide-based structure.
226. A composition of matter of embodiment 225, wherein $L_1$ and $L_2$ are each independently a hydrazone linker and $M_1$ and $M_2$ are each independently Fe.
227. A composition of matter of embodiment 225 or 226, wherein $B_1$ and $B_2$ each independently include 10-16 carbon atoms, 9-15 oxygen atoms, and 16-28 hydrogen atoms.
228. A composition of matter of embodiment 225, 226, or 227, wherein $B_1$ and $B_2$ are each independently derived from sucrose.

Example 1

Renal Protection.

The data described in FIGS. 1-4 and Tables 1-7 was collected using the following protocols:

The Glycerol Model of AKI.

This is a widely used model of rhabdomyolysis-induced AKI that has been employed worldwide for 50 years. The model was used to test whether prophylactic interventions confer protection against AKI. Basically, the protocol is as follows: Male CD-1 mice (35-45 grams), obtained from Charles River Laboratories, Wilmington, Mass. were studied. Mice were maintained under standard vivarium conditions and generally housed for 1-3 weeks prior to study. The mice were placed in a cylindrical restraining cage, and then were given a tail vein injection of the test substances (see below) or test substance vehicle. The mice were then returned to their cages. Eighteen hours (hrs) later, the mice were briefly anesthetized by isoflurane inhalation, and given an intramuscular injection of hypertonic (50%) glycerol in a dose of 9 ml/Kg body weight. The dose is divided in two, with half injected into the muscle of each of the hind limbs. The mice were then returned to their cages. Eighteen hrs later, the mice were deeply anesthetized with pentobarbital (50-100 mg/Kg), the abdominal cavity was opened through a midline abdominal incision, a blood sample was obtained from the abdominal vena cava and the kidneys were resected. A kidney cross section was obtained and fixed in formalin for subsequent histologic analysis. The terminal blood samples were analyzed for BUN and creatinine, using commercially available assay kits. The remaining kidney tissue was subjected to cortical dissection, and the cortical tissues were then extracted for protein and RNA. The protein samples were saved for analysis of HO-1 levels, and the RNA samples were subjected to RT-PCR to quantify HO-1 mRNA as well as levels of other stress gene mRNAs (e.g. NGAL, haptoglobin, hemopexin, hepicidin).

Test preparation: Lyophilized horse skeletal muscle (myoglobin) (Sigma Chemicals) was used as the test agent.

Myoglobin+SnPP: To 5 mg of dry myoglobin was added 0.9 ml of PBS+0.1 ml of a stock SnPP solution (50 umole/ml). The resulting final concentrations were 5 mg/ml myoglobin+5 umoles/ml of SnPP. The tail vein was injected with 200 ul of this solution, which equals 1 mg myoglobin+1 umole SnPP.

Nitrited Myoglobin: Na nitrite was added to myoglobin to achieve a 1-5 mole/mole ratio to myoglobin (e.g. 1-5 umole of nitrite/1 umole of myoglobin). The resulting final concentrations were 5-10 mg/ml myoglobin+0.04-0.4 mg/ml nitrite. The tail vein was injected with 200 ul of this solution.

Myoglobin+PEG: To a stock solution of 20 mg/ml Mgb in PBS was added 100 mg/ml of PEG-6000; 0.250 ul. This was administered as a subcutaneous injection in the dorsal neck (250 ul total injection). For combined Mgb/PEG+SnPP, SnPP was added to the above in a concentration of 3 mg/ml.

These are the test materials administered to mice to assess protection against the glycerol AKI model, as noted above.

Independent effects of each test agent: To assess whether myoglobin+SnPP had a greater effect than either myoglobin alone or SnPP alone, the same solutions as noted above were created as follows: myoglobin+SnPP; SnPP alone, or myoglobin alone. These were used in the above noted glycerol model.

Four hr post myoglobin vs myoglobin+SnPP vs SnPP alone experiments. To confirm that the myoglobin+SnPP has a synergistic effect in inducing HO-1 mRNA and HO-1 protein levels, each of the above combinations have been administered alone via tail vein injection. Four hrs later, the mice were sacrificed as noted above and the kidneys were harvested for assessment of HO-1 mRNA and protein levels. For additional information regarding methods, see Zager et al., Am J Physiol Renal Physiol. 2014 Jul. 30. Pii.

TABLE 1

SnPP quadruples the amount of HO-1 mRNA induction at 4 hrs post injection vs. myoglobin alone (HO-1/GAPDH mRNA)

|  | 4 hr IV Control | 4 hr IV Myoglobin | 4 hr IV SnPP | 4 hr IV Myoglobin & SnPP |
|---|---|---|---|---|
|  | 1.80 | 2.58 | 6.95 | 13.80 |
|  | 2.49 | 2.41 | 2.85 | 12.05 |
|  | 1.50 | 7.78 | 9.72 | 13.51 |
|  |  | 2.93 | 8.25 | 12.36 |
| Average | 1.93 | 3.93 | 6.94 | 12.93 |
| Std Error | 0.29 | 1.29 | 1.48 | 0.43 |
| Unpaired p (vs Control) |  | 0.25 | 0.036 | 0.000006 |
| Unpaired p (vs Ovnt Myoglobin) |  |  | 0.17 | 0.00057 |
| Unpaired p (vs Ovnt SnPP) |  |  |  | 0.0080 |

As shown in Table 2, at the 4 hr time point, there is a preferential increase in HO-1 protein expression (by ELISA). Given that it is just 4 hrs post injection, the mRNA increases are greater than the protein increases as protein synthesis must follow the mRNA induction-requiring more time.

TABLE 2

Preferential Increase in HO-1 Protein Expression (by ELISA) at the 4 Hr Time Point (Cortex: ng HO-1/mg protein)

|  | 4 Hr IV PBS | 4 hr IV Carrier (0.01N NaOH) | 4 hr IV 1 mg Myoglobin | 4 hr IV 1 μmole SnPP | 4 hr IV 1 mg Myoglobin & 1 μmole SnPP |
|---|---|---|---|---|---|
|  | 12.6 | 20.2 | 64.7 | 53.6 | 68.8 |
|  | 12.9 | 22.8 | 36.0 | 32.2 | 41.7 |
|  | 15.6 |  | 40.7 | 31.5 | 88.6 |
|  | 13.1 |  | 40.2 | 20.5 | 86.4 |
| Average | 13.5 | 21.5 | 45.4 | 34.4 | 71.4 |
| Std Error | 0.7 | 1.3 | 6.5 | 6.9 | 10.8 |
| Unpaired p (vs Control) |  | 0.0037 | 0.0028 | 0.024 | 0.0018 |
| Unpaired p (vs Carrier - 0.01N NaOH) |  |  | 0.071 | 0.28 | 0.038 |
| Unpaired p (vs IV myoglobin) |  |  |  | 0.29 | 0.086 |
| Unpaired p (vs IV SnPP) |  |  |  |  | 0.028 |

Table 3 shows HO-1 mRNA induction roughly 18 hrs (overnight) post injection vs. myoglobin alone (HO-1/GAPDH mRNA) vs. myoglobin in combination with SnPP.

TABLE 3

HO-1 mRNA induction overnight post injection with control (PBS), myoglobin alone (HO-1/GAPDH mRNA), and myoglobin in combination with SnPP.

| Subject | Ovnt IV Control (PBS) | Ovnt IV 1 mg Myoglobin | Ovnt IV 1 mg Myoglobin + 1 μmole SnPP |
|---|---|---|---|
| 1 | 0.28 | 0.51 | 0.75 |
| 2 | 0.47 | 0.71 | 2.26 |
| 3 | 0.62 | 0.53 | 6.76 |
| Average | 0.46 | 0.58 | 3.26 |
| Std Error | 0.10 | 0.06 | 1.81 |
| unpaired p (vs Normal) |  | 0.35 | 0.20 |
| unpaired p (vs IV Myoglobin) |  |  | 0.21 |

Table 4 shows HO-1 protein induction roughly 18 hrs (overnight) post control injection vs. myoglobin alone (HO-1/GAPDH mRNA) vs. myoglobin in combination with SnPP.

TABLE 4

HO-1 protein induction overnight post control injection, myoglobin alone (HO-1/GAPDH mRNA), and myoglobin in combination with SnPP.

| Subject | Ovnt IV Control (PBS) | Ovnt IV 1 mg Myoglobin | Ovnt IV 1 mg Myoglobin + 1 μmole SnPP |
|---|---|---|---|
| 1 | 24.8 | 24.6 | 61.4 |
| 2 | 16.0 | 50.6 | 93.6 |
| 3 | 20.6 | 34.9 | 102.6 |
| Average | 20.5 | 36.7 | 85.9 |
| Std Error | 2.5 | 7.6 | 12.5 |
| unpaired p (vs Control) |  | 0.11 | 0.0068 |
| unpaired p (vs Myoglobin) |  |  | 0.028 |
| Correlation protein vs mRNA r= |  |  | 0.80 |

FIGS. 1A and 1B show HO mRNA expression (FIG. 1A) and protein expression (FIG. 1B) following vehicle (control), myoglobin (Mgb), or myoglobin in combination with SnPP (Mgb+SnPP) administration 18 hours before glycerol insult. The data indicate that there is a potentiation of myoglobin induced HO-1 induction with concomitant SnPP treatment.

Table 5 shows induction of haptoglobin protein expression following exposure to myoglobin alone or myoglobin in combination with PEG as compared to carrier control. The data demonstrate that myoglobin+PEG induce far greater increases in cytoprotective haptoglobin expression than myoglobin alone.

TABLE 5

Haptoglobin Protein Expression 4 hour time point after SQ injection.

| Control | Myoglobin Alone | Myoglobin + PEG |
|---|---|---|
| 9.5 ± −2.9 ng/mg protein | 32.7 ± 6.3 ng/mg protein | 118.8 ± 20 ng/mg protein<br>p < 001 vs control;<br>p < 0.025 vs Myoglobin alone |

Table 6 shows plasma LDH levels—a sensitive marker of liver, kidney, lung, and heart injury. Myoglobin+SnPP did not cause an LDH increase at the 4 hr time point.

TABLE 6

Myoglobin + SnPP Does not cause an LDH increase at the 4 hr time point (Plasma: Absorbance U LDH/ml)

| Subject | 4 hr IV Carrier | 4 hr IV Myoglobin | 4 hr IV SnPP | 4 hr IV Myoglobin & SnPP |
|---|---|---|---|---|
| 1 |  | 4.54 | 4.54 | 5.06 |
| 2 |  | 4.91 | 5.29 | 5.63 |
| 3 | 5.36 | 4.54 | 5.00 | 5.78 |
| 4 | 3.49 | 3.90 | 3.23 | 3.30 |
| Average | 4.43 | 4.47 | 4.51 | 4.94 |
| Std Error | 0.94 | 0.21 | 0.46 | 0.57 |
| Unpaired p (vs Carrier) |  | 0.95 | 0.93 | 0.64 |
| Unpaired p (vs Myoglobin) |  |  | 0.94 | 0.47 |
| Unpaired p (vs SnPP) |  |  |  | 0.58 |

FIG. 2 left panels show cellular kidney damage following glycerol insult and the FIG. 2 right panels show the protective effect of pre-treatment with myoglobin in combination with SnPP.

Figure 3:
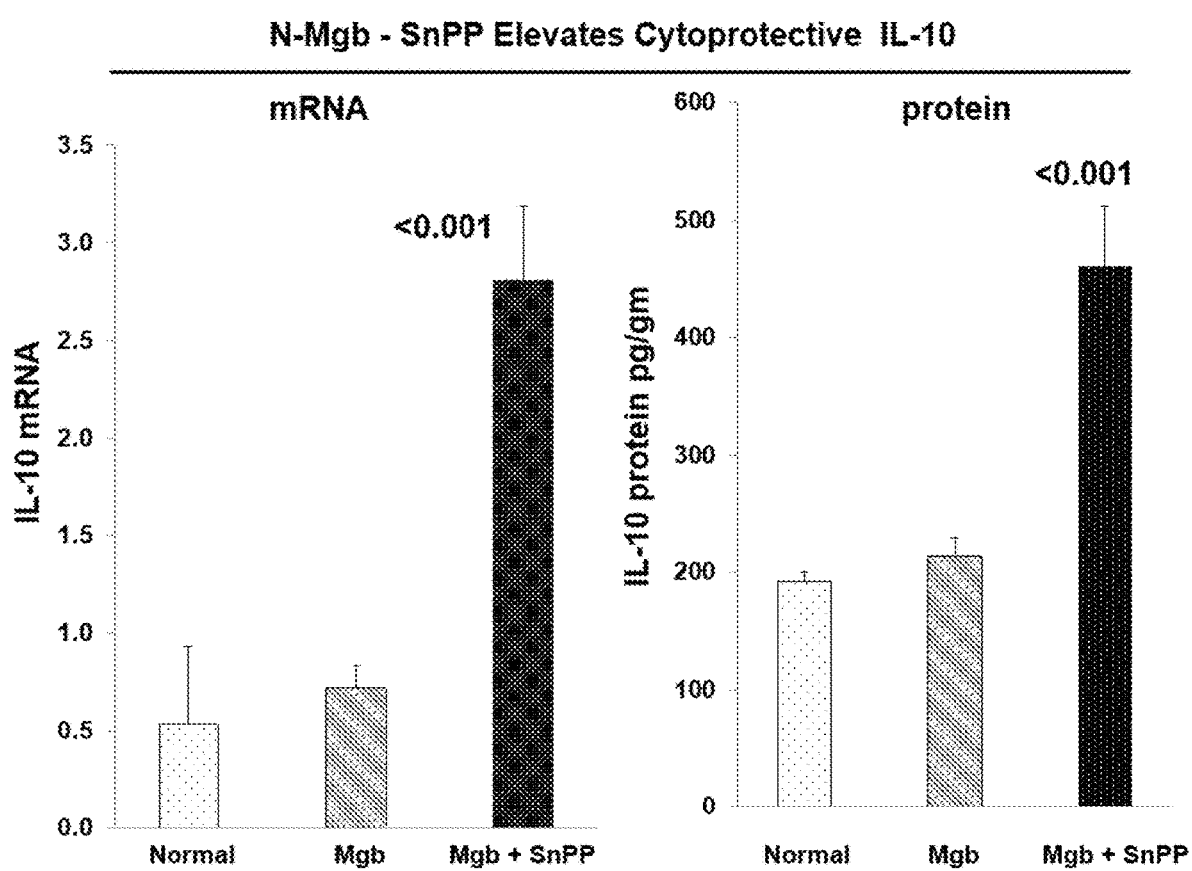
FIG. 3 shows that N-Mgb+SnPP elevates mRNA for the protective stress protein, interleukin-10 (IL-10).

FIG. 3 shows that N-Mgb+SnPP preferentially elevate the protective stress protein, interleukin-10 (IL-10).

Figure 4:
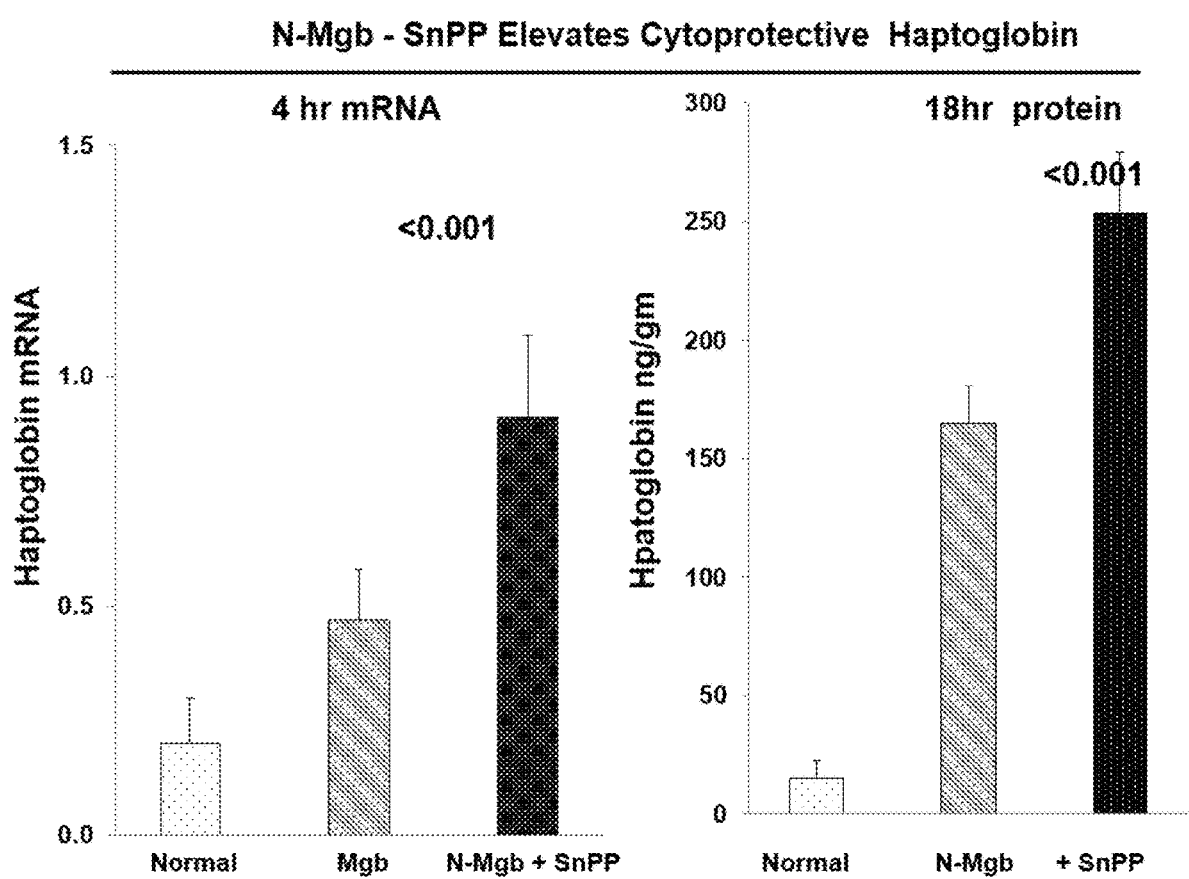
FIG. 4 shows that N-Mgb+SnPP elevates the hatpoglobin mRNA (left) and protein levels (right).

FIG. 4 shows that N-Mgb+SnPP elevates the protective stress protein, haptoglobin.

Example 2

Hepatic Protection.

Hepatotoxic injury was assessed by plasma LDH levels 24 hrs after insult. Liver insult included 9 ml/kg glycerol injection (this is the same model that is used to cause renal injury). Liver injury raised plasma LDH from 3.5 to 114 units/ml. With myoglobin/SnPP pre-treatment, plasma LDH levels were reduced by 75%.

TABLE 7

Hepatotoxic injury assessed by plasma LDH levels 24 hrs after insult.

| Subject No. | Control | Hepatic Injury | Hepatic Injury + Myoglobin + SnPP |
|---|---|---|---|
| 1 | 3.7 | 4.4 | |
| 2 | 2.1 | 130.1 | 10.4 |
| 3 | 3.9 | 69.5 | 20.9 |
| 4 | 4.1 | 87.5 | 60.2 |
| 5 | | 128.3 | 38.9 |
| 6 | | 155.4 | 61.3 |
| Mean | 3.5 | 114.2 | 32.7 |
| Std Error | 0.5 | 15.6 | 10.1 |
| Unpaired t test (injury +/− myoglobin + SnPP) | | | $p < 0.0014$ |

The data described in Examples 1 and 2 show that heme protein, modified heme protein, and heme protein in combination with a heme protein degradation inhibitor protect the kidney and liver from injury due to glycerol insult. The protection is evidenced through markers of injury (LDH), organ function (BUN and creatinine) and induction of protective stress proteins (HO-1 and haptoglobin).

Example 3

Figure 5:
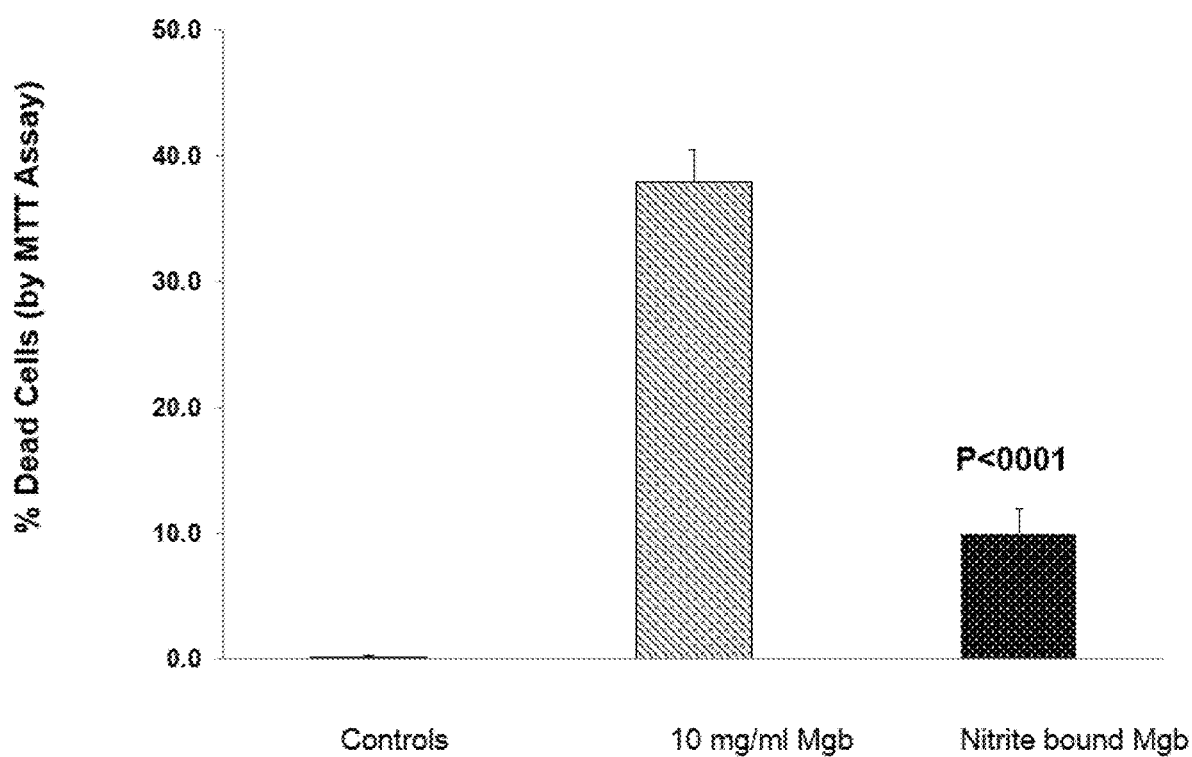
FIG. 5 shows assessment of the impact of equimolar nitrite binding to myoglobin Fe on the expression of myoglobin toxicity. HK-2 cells (a proximal tubule cell line derived from normal human kidney) were incubated in keratinocyte serum free medium either under normal (control) conditions or in the presence of 10 mg/mL horse skeletal muscle myoglobin or nitrited myoglobin (produced by equimolar Na nitrite addition to 10 mg/ml myoglobin). After 18 hr incubations, the severity of cell injury (% cell death) was assessed by MTT assay. Myoglobin induced 40% cell death (40% decrease in MTT cell uptake), compared to control incubated cells. Nitrite binding to myoglobin reduced cell death by 75%. Thus, nitrite binding is able to reduce myoglobin's cytotoxic effects.

FIG. 5 shows assessment of the impact of equimolar nitrite binding to myoglobin Fe on the expression of myoglobin toxicity. HK-2 cells (a proximal tubule cell line derived from normal human kidney) were incubated in keratinocyte serum free medium either under normal (control) conditions or in the presence of 10 mg/mL horse skeletal muscle myoglobin or nitrited myoglobin (produced by equimolar Na nitrite addition to 10 mg/ml myoglobin). After 18 hr incubations, the severity of cell injury (% cell death) was assessed by MTT assay. Myoglobin induced 40% cell death (40% decrease in MTT cell uptake), compared to control incubated cells. Nitrite binding to myoglobin reduced cell death by 75%. Thus, nitrite binding is able to reduce myoglobin's cytotoxic effects.

Figure 6:
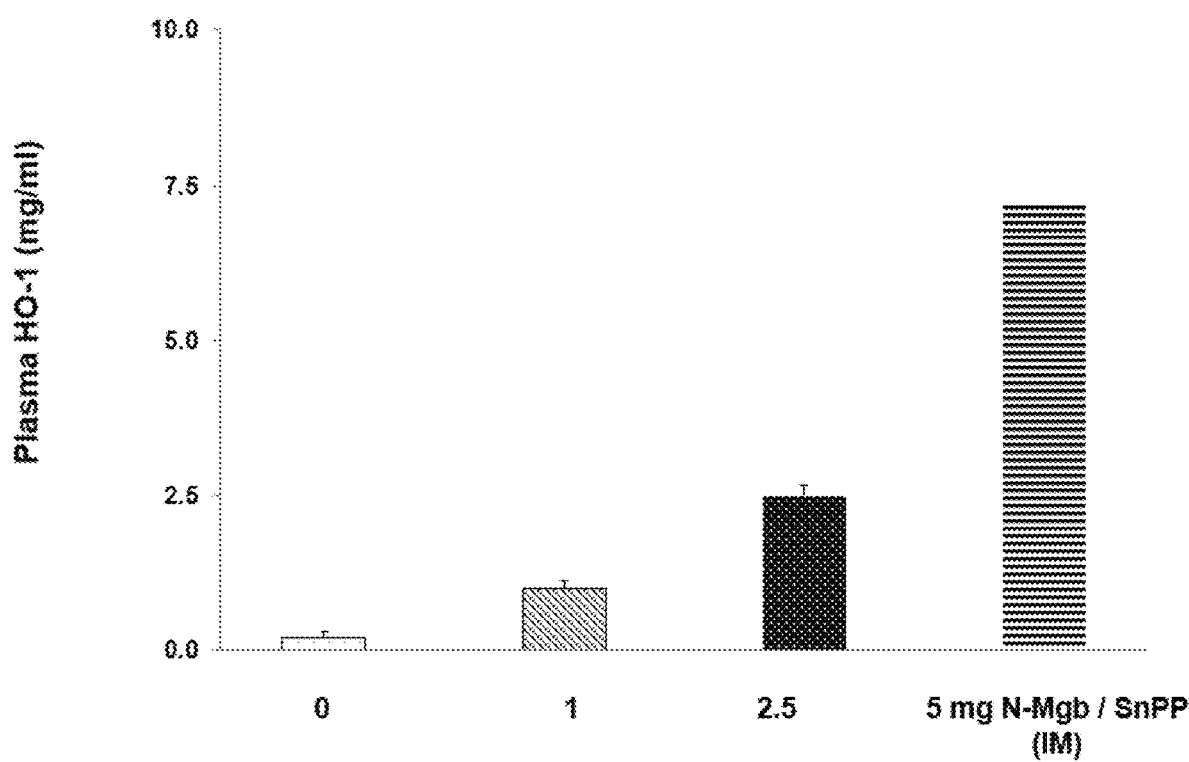
FIG. 6 shows the dose-response relationship between plasma heme oxygenase 1 (HO-1) and administered N-myoglobin dose. Normal mice were injected intramuscularly (IM) with either 0, 1, 2, or 5 mg/Kg nitrited myoglobin+ SnPP (constant dose of 1 µmole). Eighteeen hrs later, plasma HO-1 levels were assessed by ELISA. A steep dose— response relationship between the administered N-myoglobin dose and plasma HO-1 levels was observed. Thus, HO-1 assay has potential biomarker utility for N-Mgb/SnPP induced HO-1 induction.

FIG. 6 shows the dose-response relationship between plasma heme oxygenase 1 (HO-1) and administered N-myoglobin dose. Normal mice were injected IM with either 0, 1, 2, or 5 mg/Kg nitrited myoglobin+SnPP (constant dose of 1 μmole). Eighteeen hrs later, plasma HO-1 levels were assessed by ELISA. A steep dose—response relationship between the administered N-myoglobin dose and plasma HO-1 levels was observed. Thus, HO-1 assay has potential biomarker utility for N-Mgb/SnPP induced HO-1 induction.

Figure 7:
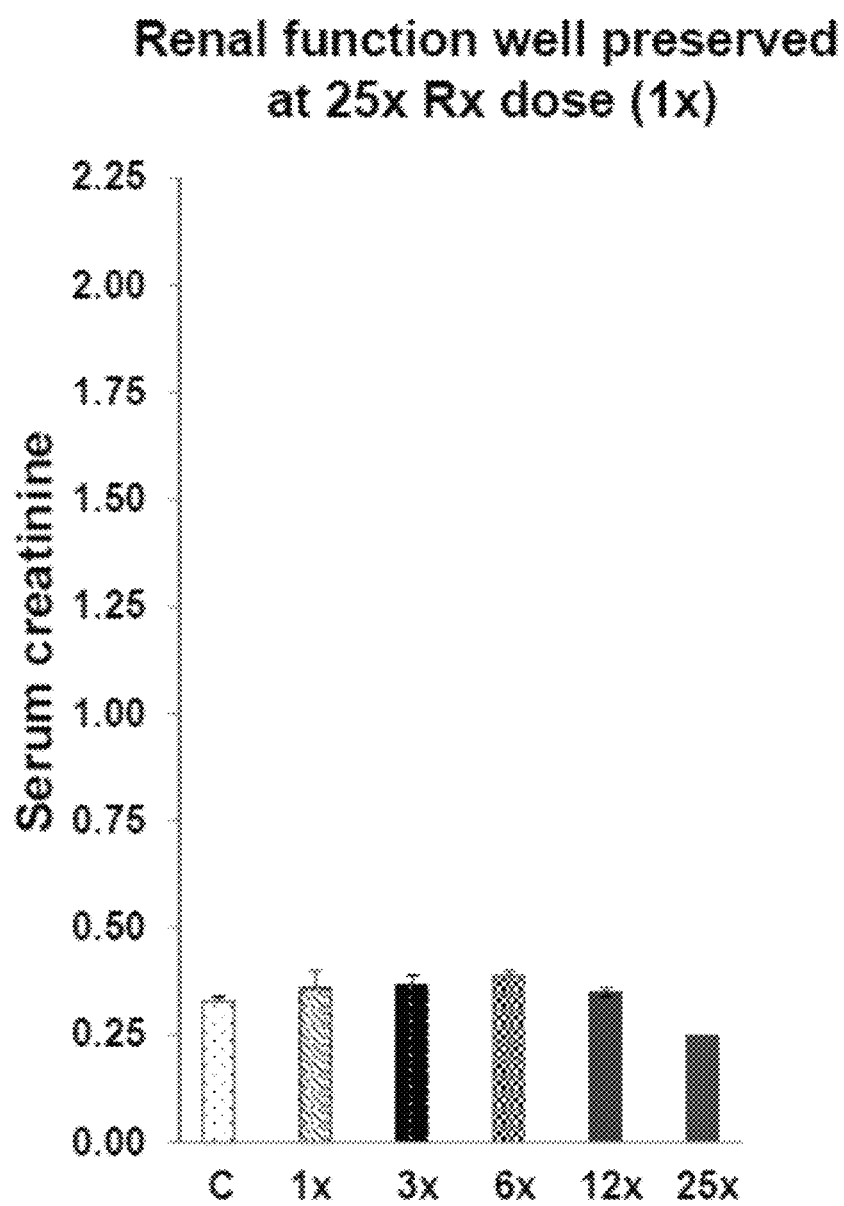
FIG. 7 shows maintenance of normal serum creatinine levels over a 25 fold variation in N-myoglobin dose. Mice were subjected to a 2 hr subcutaneous infusion of 1, 3, 6, 12, or 25 mg/Kg of nitrited myoglobin (holding SnPP at a constant dose of 1 µmole). Eighteen hrs later, potential renal injury was assessed by measuring serum creatinine concentrations. No significant increase was observed at any of the N-Mgb doses, indicating a lack of over toxicity (n, 2-4 mice/group).

FIG. 7 shows maintenance of normal serum creatinine levels over a 25 fold variation in N-myoglobin dose. Mice were subjected to a 2 hr subcutaneous infusion of 1,3,6,12, or 25 mg/Kg of nitrited myoglobin (holding SnPP at a constant dose of 1 μmole). Eighteen hrs later, potential renal injury was assessed by measuring serum creatinine concentrations. No significant increase was observed at any of the N-Mgb doses, indicating a lack of over toxicity (n, 2-4 mice/group).

Example 4

Introduction.

Acute kidney injury (AKI) is a well-recognized risk factor for morbidity, mortality, and the initiation of chronic kidney disease (CKD; Ishani et al. J Am Soc Nephrol 2009; 20:223-8; Xue et al. J Am Soc Nephrol 2006; 17:1135-42; Liangos et al. Clin J Am Soc Nephrol 2006; 1:43-51; Wald et al. JAMA 2009; 302:1179-85; Goldberg et al. Kidney Int 2009; 76:900-6). However, no proven ways to prevent AKI currently exist. It is well established that after an initial bout of ischemic or toxic injury, the kidney develops marked resistance to subsequent damage (e.g., Honda et al. Kidney Int 1987; 31:1233-8; Zager et al. Kidney Int 1984; 26:689-700; Zager et al. Lab Invest 1995; 72:592-600; Zager, Kidney Int 1995; 47:1336-45; Zager, Kidney Int 1995; 47:628-37). This phenomenon, which is mediated in part by an upregulation of cytoprotective and anti-inflammatory "stress" proteins (e.g., heme oxygenase 1 (HO-1), ferritin, haptoglobin, hemopexin, alpha 1 antitrypsin, interleukin 10 (IL-10) has been referred to as "ischemic preconditioning" or the "acquired cytoresistance" state. Zager et al. J Am Soc Nephrol 2014; 25:998-1012; Deng et al. Kidney Int 2001; 60: 2118-28; Zarjou et al. J Clin Invest 2013; 123:4423-34; Nath et al. J Clin Invest 1992; 90:267-70; Zager et al. Am J Physiol 2012; 303:F1460-72; Fink, J Leukoc Biol 2009; 86:203-4 Arredouani et al. Immunology 2005; 114:263-71; Blum et al. J Am Coll Cardiol 2007; 49:82-7; Galicia et al. Eur J Immunol 2009; 39:3404-12; Zager et al. Am J Physiol 2012; 303:F139-48; Zager et al. PLoS One 2014; 9:e9838; Hunt & Tuder, Curr Mol Med 2012; 12:827-35; Janciauskiene et al. J Biol Chem 2007; 282:8573-82.

Given the profound protective nature of acquired cytoresistance, investigators have sought ways to safely recapitulate it in humans. Notable in this regard is so-called "remote preconditioning," whereby recurrent bouts of upper and lower limb ischemia are induced by recurrently inflating and deflating blood pressure cuffs. Yang et al. Am J Kidney Dis 2014; 64:574-83; Mohd et al. J Surg Res 2014; 186:207-16; Li et al. J Cardiothorac Surg 2013; 8:43. The goal is to release unknown tissue "conditioning factors" into the systemic circulation that will trigger protective tissue responses (e.g., in brain, heart, liver, and kidney). Despite its appeal, this approach has had only questionable success, likely because of the following reasons: (1) the "factors" released from postischemic limbs that might induce "preconditioning," and how much factor release is required to induce this state, are unknown; (2) the cellular pathways by which such factors impact distant organs to induce cytoresistance have not been defined; and (3) it is impossible to judge whether the desired preconditioning actually develops in any given individual.

An alternative approach for inducing acquired cytoresistance was sought. To this end, a pharmacologic regimen including low dose nitrited myoglobin (N-Mgb)+tin protoporphyrin (SnPP), which markedly and synergistically upregulate a host of renal tubular cell cytoprotectants (e.g., HO-1, haptoglobin, and IL-10) in the absence of obvious renal or extrarenal toxicities was developed. Within 18 hours of agent administration, striking resistance to nephrotoxic AKI, adenosine triphosphate (ATP) depletion-induced AKI, and post-AKI progression to CKD result. In addition, hepatic protection against postischemic and toxic injury is expressed. Lastly, it was observed that the induction of this cytoresistant state can be gauged noninvasively by using plasma HO-1 and haptoglobin levels as "biomarkers" of its induction.

Methods.

General approach. Animals. All experiments were conducted using male CD-1 mice (35-45 g; Charles River Laboratories, Wilmington, Mass.). They were housed under standard vivarium conditions with free food and water access throughout. The used protocols were approved by the Institution's Institutional Animal Care and Utilization Committee (IACUC) according to the National Institutes of Health guidelines.

Cytoresistance-Inducing Reagents.

Horse skeletal muscle (#Mb0360; Sigma) was used as the primary cytoresistance-inducing agent. However, because myoglobin (Mgb) has an inherent nephrotoxic potential (particularly under conditions of volume depletion and aciduria), two approaches were used to mitigate Mgb's potential adverse effects. First, the Mgb was converted into a nitrited form by the addition of equimolar amount of sodium (Na) nitrite. In this regard, nitrite is an ambidentate molecule that directly binds 1:1 to myoglobin Fe either via its oxygen or nitrogen component. Cotton et al. Advanced inorganic chemistry. Hobocken, N.J.: Wiley-Interscience, 1999:1355; Silaghi-Dumitrescu et al. Nitric Oxide 2014; 42C:32-9. Noteworthy is that Fe is the dominant mediator of Mgb's cytotoxic effect, (Zager et al. J Clin Invest 1992; 89:989-95; Zager & Burkhart, Kidney Int 1997; 51:728-38) and this toxicity is substantially reduced by prior nitrite binding. Rassaf et al. Circ Res 2014; 114:1601-10; Totzeck et al. Circulation 2012; 126:325-34 [J Clin Invest 1992; 89: 989-95]; Totzeck et al. PLoS One 2014; 22:e105951; Hendgen-Cotta et al. Proc Natl Acad Sci USA 2008; 105:10256-61.

In addition to its ability to decrease Fe-mediated toxicity, nitrite has been implicated as a mediator of "remote preconditioning," possibly through nitric oxide (NO) generation. Rassaf, supra. In this regard, heme proteins directly reduce nitrite, with resultant NO production. Juncos et al. Am J Pathol 2006; 169:21-31; Kellerman, J Clin Invest 1993; 92:1940-9; Zager et al. Am J Physiol 2008; 294:F187-97. Thus, by binding nitrite directly to Mgb, Mgb injection with subsequent proximal tubule endocytic uptake, results in direct proximal tubule nitrite and NO targeting.

Second, for heme Fe to induce most of its cytotoxicity, it must first be released from its sequestration site within the porphyrin ring. This Fe release is mediated via porphyrin ring cleavage via HO-1. Hence, to attenuate potential Mgb cytotoxicity, it was administered along with a transient HO-1 inhibitor, SnPP. In this regard, it has previously been reported that SnPP addition to Mgb-exposed cultured proximal tubule (HK-2) cells or to in vivo heme loaded mouse proximal tubule segments reduces Mgb toxicity by as much as 85%. Zager & Burkhart, Kidney Int 1997; 51:728-38. This cytoprotective action is further indicated by observations that SnPP may mitigate postischemic acute renal failure (ARF). Juncos et al. Am J Pathol 2006; 169:21-31; Kaizu et al. Kidney Int 2003; 63:1393-403.

Impact of Mgb, SnPP, and Mgb 1 SnPP on renal cortical heme signaling. It was postulated that (1)N-Mgb would be a potent signaling molecule, leading to the upregulation of heme responsive element and redox sensitive genes, which evoke cytoprotective activities (e.g., HO-1, haptoglobin, hemopexin, and IL-10); (2) SnPP can independently upregulate such genes; and (3) when administered together, N-Mgb+SnPP coadministration can lead to additive or synergistic heme responsive element signaling. The following experiment tested these hypotheses.

Thirty-two mice were divided into 4 equal groups: (1) control mice; (2) mice treated with 1 mg of N-Mgb injection (as a bolus through the tail vein); (3) mice treated with 1 mmol of SnPP (via tail vein); and (4) mice treated with combined N-Mgb 1 SnPP. After either 4 hours (n=16) or 18 hours (n=16), the mice were deeply anesthetized with pentobarbital (50 mg/kg), the abdomen was opened through a midline abdominal incision, and the kidneys were removed. To determine potential effects on extrarenal organs, a liver lobe and the heart were also removed. The tissues were iced and then extracted for protein and RNA (RNeasy Plus Mini; Qiagen, Valencia, Calif.) and subjected to enzyme linked immunosorbent assay (ELISA) and reverse transcriptase polymerase chain reaction (RT-PCR) for HO-1, haptoglobin, and IL-10 protein and messenger RNAs (mRNAs). Zager et al. J Am Soc Nephrol 2014; 25:998-1012; Zager et al. Am J Physiol 2012; 303:F139-48. As an assessment of renal function, control mice and the 18 hour after N-Mgb+SnPP-treated mice had blood urea nitrogen (BUN) and plasma creatinine levels measured. Additionally, transverse 10% formalin fixed kidney sections (3 mM) were cut and stained with hematoxylin and eosin (H&E) and periodic acid Schiff (PAS) to further assess potential injury.

Assessments of cytoresistance. Glycerol model of rhabdomyolysis-induced AKI. Twenty mice were divided into 4 equal groups (controls, mice treated with N-Mgb, SnPP, and mice treated with N-Mgb+SnPP tail vein injections) as described previously. 18 hours later, the mice were briefly anesthetized with isoflurane and immediately injected with 9 mL/kg of 50% glycerol, administered in equally divided doses into each hind limb. At 18 hours after glycerol injection, the mice were anesthetized with pentobarbital, the abdomen was opened, a blood sample for BUN and creatinine assessments was obtained from the vena cava, and the kidneys were resected. The control post-glycerol group and the N-Mgb+SnPP-pretreated glycerol group had kidney sections stained with H&E.

Maleate model of AKI. When injected into rodents, maleate undergoes selective proximal tubule uptake via organic anion transporters and induces profound, proximal tubule-specific ATP depletion. Kellerman, J Clin Invest 1993; 92:1940-9; Zager et al. Am J Physiol 2008; 294:F187-97. This culminates in severe AKI. The following experiment assessed whether N-Mgb+SnPP pretreatment can protect against this form of renal damage. Twelve mice were divided into 2 equal groups, which received either N-Mgb–SnPP or vehicle injection. Eighteen hours later, they all received an intraperitoneal (IP) injection of Na maleate (600 mg/kg). Zager et al. Am J Physiol 2008; 294:F187-97. 18 hours later, the mice were anesthetized, and terminal blood samples were obtained from the inferior vena cava for BUN and creatinine measurements.

Postischemic AKI progression to CKD.

After 30 minutes of unilateral renal ischemia, the damaged kidney undergoes a transition to CKD, manifested by progressive tubular dropout, interstitial inflammation, and fibrosis, culminating in a 40% loss of renal mass (kidney weight). Zager et al. Am J Physiol 2011; 301:F1334-45; Zager et al. Kidney Int 2013; 84:703-12. To ascertain whether N-Mgb–SnPP treatment could mitigate postischemic disease progression, 6 mice were pretreated with these agents and 18 hours later they were anesthetized with pentobarbital and subjected to 30 minutes of left renal pedicle occlusion performed through a midline abdominal incision at a body temperature of 37° C.

The right kidney was left untouched. After the period of renal ischemia, the vascular clamp was removed and complete reperfusion was confirmed by loss of renal cyanosis. The mice were then sutured and allowed to recover from anesthesia. Six mice, subjected to the same surgical protocol, but without N-Mgb–SnPP pretreatment, served as controls. Two weeks later, the abdominal incision was reopened and the kidneys were resected. Relative degree of renal injury between the 2 groups was assessed by loss of left renal mass (as determined by renal wet weight) vs weight of left kidneys from 6 normal mice. Renal cortical neutrophil gelatinase associated lipocalin (NGAL) mRNA and protein levels were also assessed as additional markers of renal damage.

Dose-response relationships after IP N-Mgb–SnPP injections. To assess whether a slower delivery rate of N-Mgb–SnPP (vs via intravenous [IV] bolus injection) also induces an upregulation of cytoprotective proteins and renal cytoresistance, mice were injected with 0, 1, 2.5, or 5 mg of N-Mgb 1 the standard SnPP dose (1 mmol) (3 mice each; 1 mL saline vehicle). Eighteen hours later, the mice were anesthetized with pentobarbital, a blood sample was obtained, and the kidneys were resected to determine HO-1 and haptoglobin mRNA and protein levels. To test whether plasma HO-1 and haptoglobin levels rose and reflected degrees of renal HO-1 and haptoglobin upregulation, plasma HO-1 and haptoglobin levels were also determined.

To assess whether the previously determined plasma and kidney HO-1 and haptoglobin levels correlated with degrees of cytoresistance, additional mice were injected with 0, 2.5, or 5 mg of N-Mgb 11 mmol of SnPP (n=3 mice per group). Eighteen hours later, all mice were subjected to the glycerol AKI model as described previously. Severities of AKI were determined 18 hours after glycerol injection by BUN and plasma creatinine analyses.

Hepatic ischemia experiments. Fourteen mice were subjected to the previously published partial hepatic ischemia model, which is conducted by occluding blood flow (at the portal triad) to 3 of 5 hepatic lobes for 25 minutes. Zager et al. Am J Physiol Renal Physiol 2014; 307:F856-68. Half of the mice were pretreated 18 hours earlier with 1 mg N-Mgb+1 mmol SnPP as described previously. Reperfusion after the ischemic period was assessed by restoration of normal hepatic color in the 3 involved liver lobes. Eighteen hours later, the mice were reanesthetized, the abdominal cavity was reopened, and a terminal blood sample was obtained for plasma alanine aminotransferase (ALT) and lactate dehydrogenase (LDH) levels as markers of postischemic liver damage.

Hepatotoxic Injury.

To assess whether N-Mgb–SnPP can protect against a toxic form of liver injury, 12 anesthetized mice received injections of 50% glycerol. The glycerol (8 mg/kg) was given via an IP injection to favor hepatocellular uptake via the portal circulation. Half of the mice had been pretreated 18 hours earlier with N-Mgb–SnPP (1 mg Mgb/1 mmol SnPP) as described previously. Four hours after IP glycerol injection, when the mice were still anesthetized, they were sacrificed via transection of the abdominal vena cava. The extent of acute hepatic injury was gauged by plasma ALT concentrations.

Calculations and Statistics.

All values are given as the mean 6 standard error of the mean. Statistical comparisons were made by unpaired Student's t test. If multiple comparisons were made, the Bonferroni correction was applied. The severity of renal histologic injury in the glycerol AKI model was graded on a 11 to 41 scale (least to most severe tubular necrosis and cast formation observed). The histologic results were compared by Wilcoxon rank sum test. Statistical significance was taken as a P value of <0.05.

Results.

Renal function and histology after IV N-Mgb+SnPP injection. Neither BUN nor plasma creatinine increases were observed at 18 hours after IV injection of 1 mg N-Mgb+SnPP (BUN, 22±3 vs 25±3 mg/dL; creatinine, 0.32±0.03 vs 0.30±0.04 mg dL; controls vs Mgb/SnPP treatment, respectively). Furthermore, there was no evidence of renal morphologic injury as evidenced by either PAS or H&E staining. In particular, no evidence of tubular necrosis or heme cast formation was apparent in the treatment group (see FIG. 8) The proximal tubular brush border as depicted by PAS staining, remained entirely intact (upper 2 panels). In this regard, brush border blebbing and swelling into proximal tubule lumina are judged to be highly sensitive light microscopic markers of tubular damage. Venkatachalam et al. Kidney Int 1978; 14:31-49; Donohoe et al. Kidney Int 1978; 13:208-22. Thus, these data indicated that the IV N-Mgb–SnPP treatment was well tolerated by the kidney.

Figure 9:
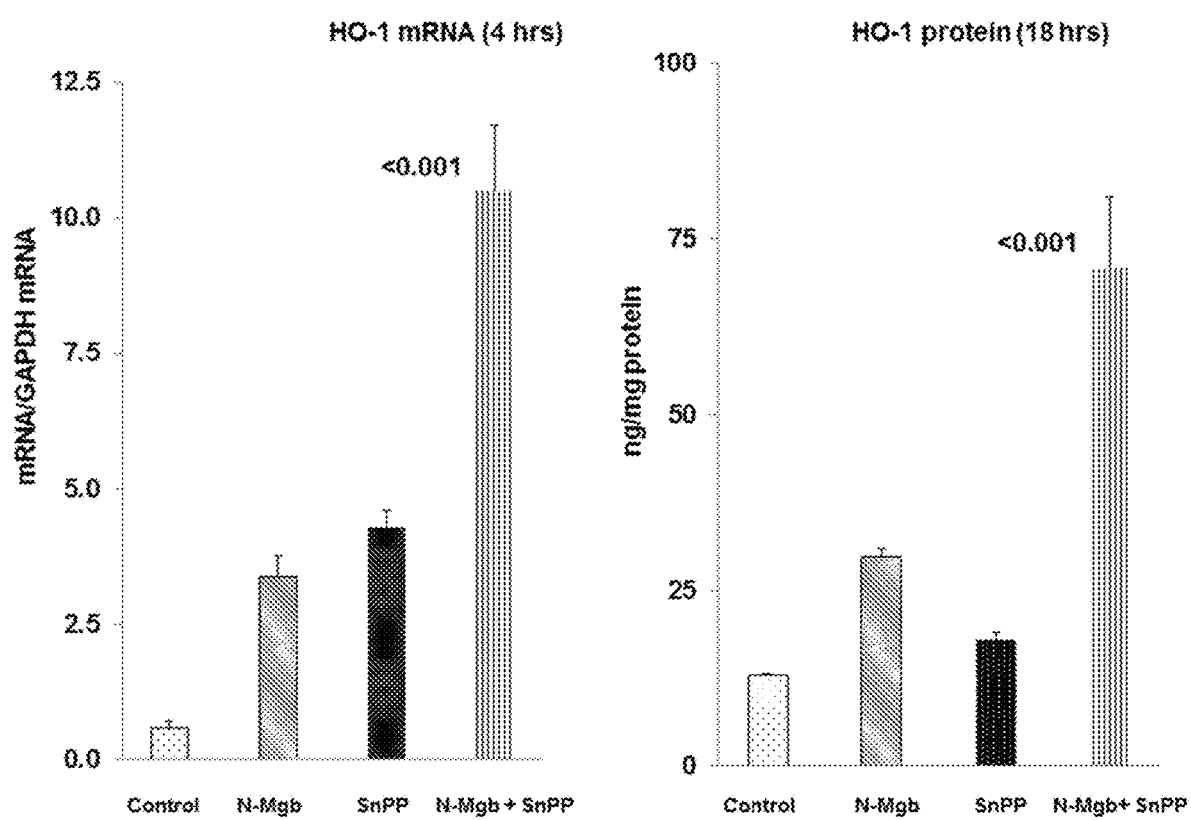
FIG. 9 shows synergistic induction of HO-1 with N-Mgb–SnPP treatment of normal mice. The left panel depicts HO-1 mRNA levels 4 hours after treatment. Whereas N-Mgb alone and SnPP alone induced modest mRNA increases, a 20-fold HO-1 mRNA increase is seen with combined agent administration. At 18 hours after administration, a synergistic HO-1 protein increase was observed (P values vs controls). GAPDH, glyceraldehyde-3-phosphate dehydrogenase; HO-1, heme oxygenase 1; mRNA, messenger RNA; N-Mgb, nitrited myoglobin; SnPP, tin protoporphyrin.

Impact of IV N-Mgb and SnPP, alone and in combination on HO-1, IL-10, and haptoglobin expressions. Renal HO-1 assessments. As shown in FIG. 9, left panel, N-Mgb alone and SnPP alone caused only modest increases in 4 hour HO-1 mRNA levels. In contrast, a 20-fold increase in HO-1 mRNA was observed at 4 hours after combined N-Mgb+SnPP injection. By 18 hours post-treatment, these mRNA increases translated into marked HO-1 protein increases, being 7-fold higher than control values. In contrast, only relatively small HO-1 protein increases were observed with N-Mgb alone or SnPP alone at the 18-hour time point. To sum up, these 4 hour mRNA and 18 hour HO-1 protein increases indicate a synergistic effect of N-Mgb+SnPP on renal cortical HO-1 gene expression. (Additional HO-1 mRNA [18 hours] and protein data [4 hours] are presented in Table 8).

TABLE 8

Kidney mRNA and protein values 4 h (a) and 18 h (b) after Rx treatment

| Measured substance | Control | N-Mgb | SnPP | SnPP 1 N-Mgb |
|---|---|---|---|---|
| (a) 4 h after Rx treatment Kidney mRNA | | | | |
| HO-1 | 0.61 ± 0 1 | 3.38 ± 0.38 | 4.38 ± 0.28 | 10.5 ± 1.23 (<0.0001) |
| Haptoglobin | 0.20 ± 0.06 | 1.94 ± 0.31 | 0.19 ± 0.01 | 5.45 ± 1.16 (<0.005) |
| IL-10 | 0.56 ± 0.20 | 1.45 ± 0.6 | 0.39 ± 0.15 | 5.18 ± 1.23 (<0.005) |

TABLE 8-continued

Kidney mRNA and protein values 4 h (a) and 18 h (b) after Rx treatment

| Measured substance | Control | N-Mgb | SnPP | SnPP 1 N-Mgb |
|---|---|---|---|---|
| HO-1 protein | 13.3 ± 1.3 | 36.1 ± 2.9 | 22.9 ± 2.6 | 55.5 ± 3.7 (<0.001) |
| Haptoglobin | 7.9 ± 1.9 | 17.6 ± 1 | 13.1 ± 1.3 | 18.9 ± 2.7 (<0.001) |
| IL-10 | 304 ± 29 | 265 ± 54 | 550 ± 86 | 838 ± 63 (<0.001) |
| (b) 18 h after Rx treatment | | | | |
| Kidney mRNA cortex | | | | |
| HO-1 | 0.61 ± 0 1 | 0.58 ± 0.18 | 0.63 ± 0.06 | 1.45 ± 0.61 (NS) |
| Haptoglobin | 0.20 ± 0.06 | 0.24 ± 0.04 | 0.23 ± 0.08 | 0.4 ± 0.19 (NS) |
| IL-10 | 0.56 ± 0.20 | 0.43 ± 0.10 | 0.18 ± 0.09 | 0.57 ± 0.13 (NS) |
| Kidney protein | | | | |
| HO-1 | 13.3 ± 1.3 | 30 ± 6 | 18 ± 2 | 71 ± 10 (<0.001) |
| Haptoglobin | 10.3 ± 2.7 | 183.8 ± 20.4 | 53.5 ± 17.2 | 203 ± 8 (<0.0001) |
| IL-10 | 304 ± 29 | 292 ± 54 | 454 ± 51 | 840 ± 60 (<0.001) |

Abbreviations: HO-1, heme oxygenase 1; IL-10, interleukin 10; mRNA, messenger RNA; N-Mgb, nitrited myoglobin; NS, not significant; Rx, treatment; SnPP, tin protoporphyrin.
Individual renal cortical mRNA and protein levels induced by the test agents administered alone or in combination at 4 h (a) and 18 h (b) after injection.

Renal IL-10 Assessments.

Figure 10:
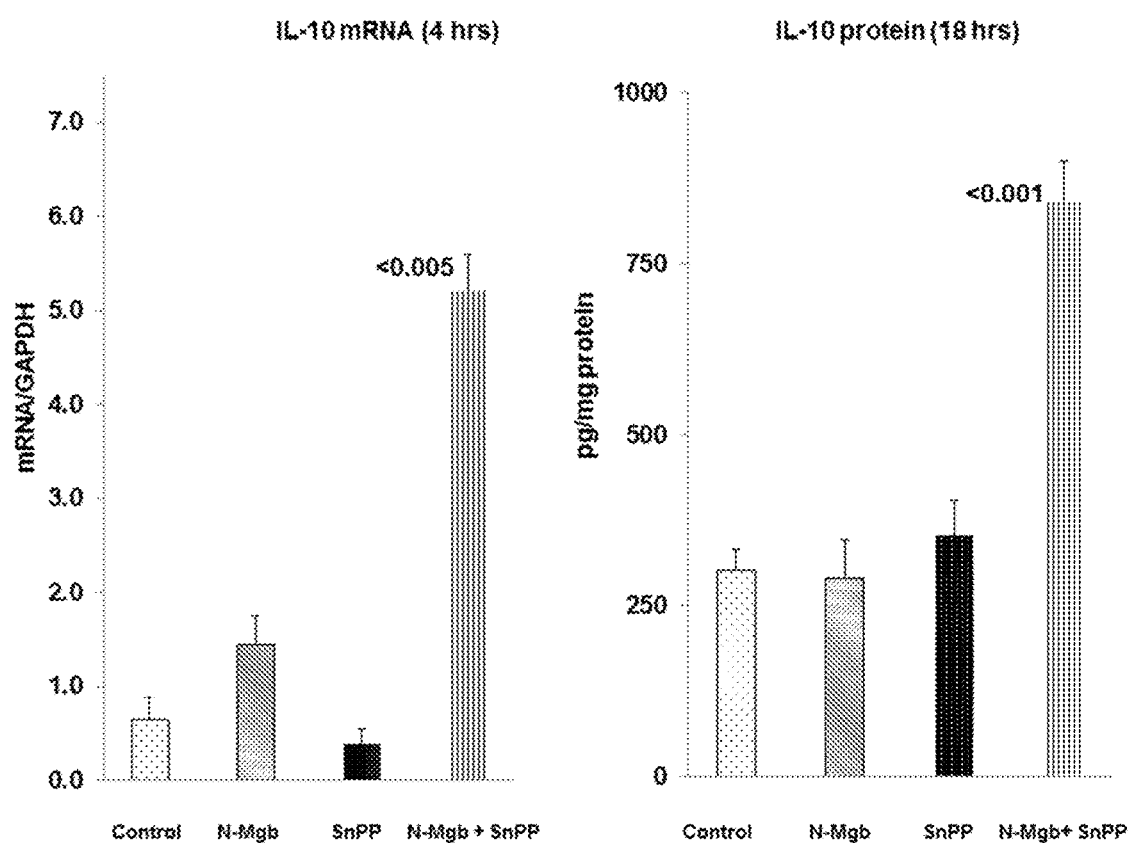
FIG. 10 shows synergistic induction of IL-10 with N-Mgb–SnPP treatment of normal mice. The left panel depicts IL-10 mRNA levels at 4 hours after treatment. N-Mgb alone and SnPP alone evoked either minimal or no IL-10 mRNA increases. However, with combined administration, a 10-fold IL-10 mRNA increase was observed. As shown in the right panel, only the combined treatment induced IL-10 protein increases as assessed at the 18-hour time point (P values vs controls).

As shown in FIG. 10, left panel, N-Mgb alone and SnPP alone had either minimal or no impact on IL-10 mRNA levels at the 4-hour time point. In contrast, combined N-Mgb+SnPP caused a 10-fold IL-10 mRNA increase at 4 hours after injection. Corresponding to these results was the absence of IL-10 protein increases at 18 hours after N-Mgb alone or SnPP injection alone. Conversely, a >2-fold increase in IL-10 protein was seen at 18 hours after combined N-Mgb–SnPP injection. (Additional IL-10 mRNA [18 hours] and protein data [4 hours] are presented in Table 8).

Renal Cortical Haptoglobin Assessments.

Figure 11:
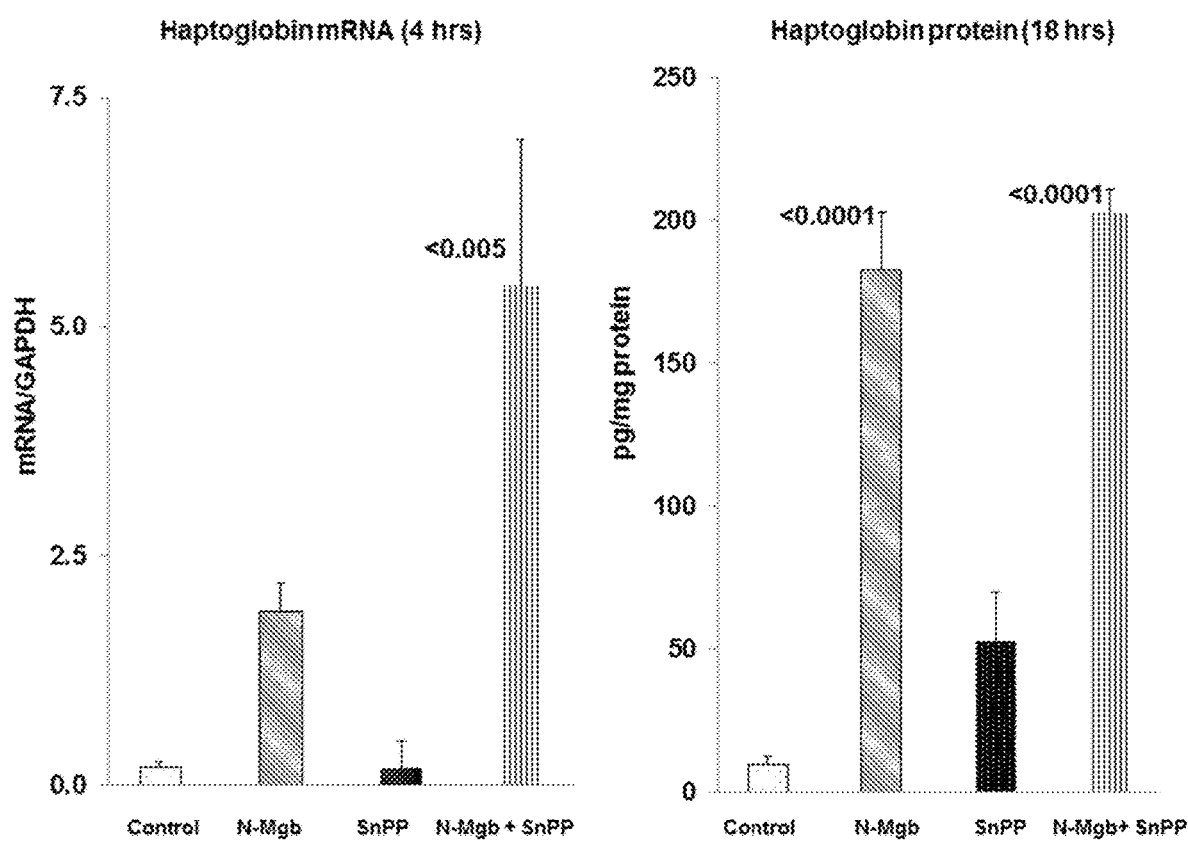
FIG. 11 shows haptoglobin mRNA and protein expression after N-Mgb–SnPP administration to normal mice. Combined N-Mgb 1 SnPP evoked far greater haptoglobin mRNA increases at 4 hours after injection than did either agent alone. However, by 18 hours after agent administration, N-Mgb alone and N-Mgb+SnPP induced comparable haptoglobin protein increases. This suggests that N-Mgb accounted for the haptoglobin increases that were produced by combined N-Mgb+SnPP administration. (P values vs controls).

As with HO-1 and IL-10, the combination of N-Mgb+SnPP induced the greatest haptoglobin mRNA increases at 4 hours after agent injection (FIG. 11). At 18 hours after injections, a massive (20-fold) increase in renal cortical haptoglobin protein levels was observed in response to N-Mgb–SnPP injection. However, the haptoglobin protein levels were comparably increased with N-Mgb alone at the 18-hour time point. This implies that it was the N-Mgb component of the combined therapy that drove the 18-hour haptoglobin protein increases. (Given this massive increase, it is conceivable that no added increase could be induced by the combination therapy). Additional haptoglobin mRNA (18 hours) and protein data (4 hours) are presented in Table 8.

Figure 12:
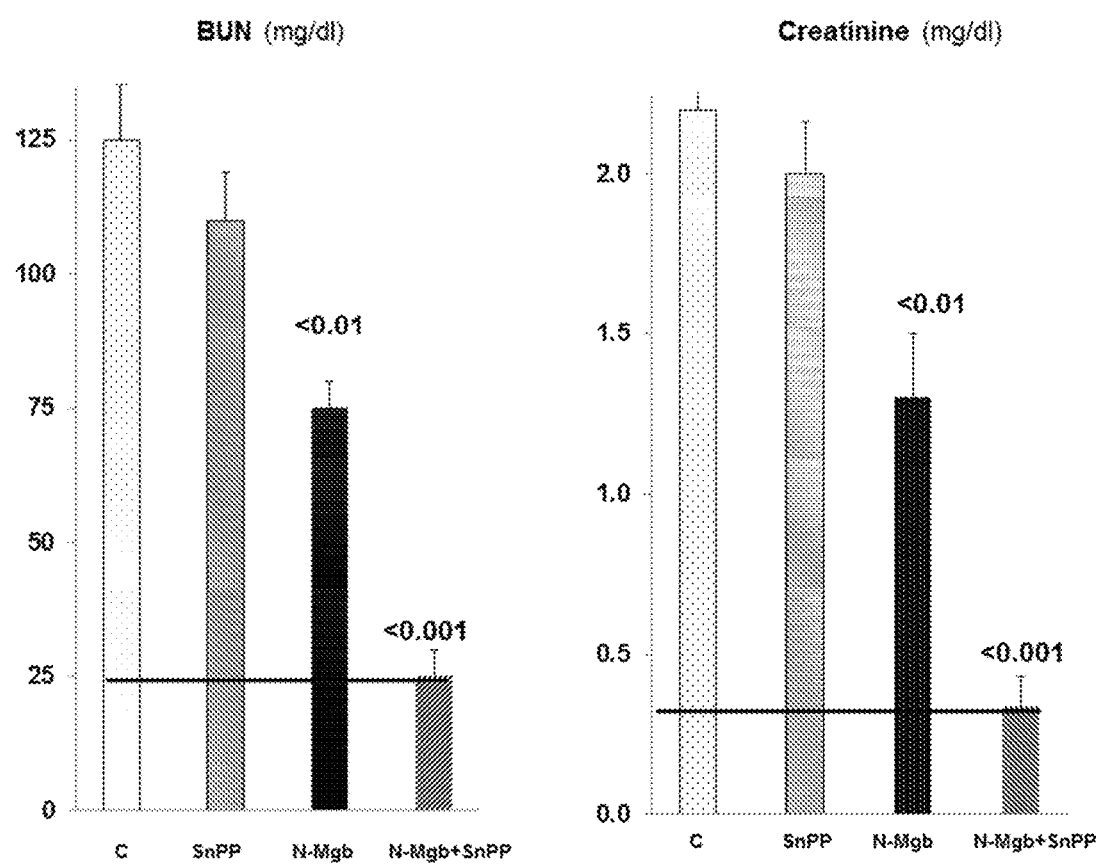
FIG. 12 shows degrees of protection induced by test agents in the glycerol model of rhabdomyolysis-induced AKI. Control mice (C) developed marked AKI as denoted by BUN and creatinine concentrations. SnPP conferred no significant protection, whereas N-Mgb induced a modest protective effect. Conversely, combined N-Mgb–SnPP administration conferred complete functional protection as gauged by normal BUN and creatinine levels at 18 hours after glycerol administration (normal levels are depicted by the solid horizontal line).

Impact of IV N-Mgb alone, SnPP alone, and N-Mgb+SnPP on the severity of the glycerol AKI model. As shown in FIG. 12, pretreatment with SnPP alone had virtually no effect on the severity of glycerol-induced AKI. N-Mgb alone induced modest protection as judged by BUN/creatinine levels. However, when N-Mgb+SnPP were used together, complete functional protection was observed (BUN/creatinine levels remained at normal values). Coinciding histologic protection was also observed (3.5±0.25 vs 1.25±0.25 histologic scores for the glycerol vs the N-Mgb+SnPP-treated group; P<0.05). In this regard, the untreated glycerol group manifested widespread tubular necrosis and cast formation as previously depicted. Zager et al. Am J Physiol Renal Physiol 2014; 307:F856-68. These changes were virtually absent in the N-Mgb+SnPP pretreatment group.

Maleate AKI Model.

Figure 13:
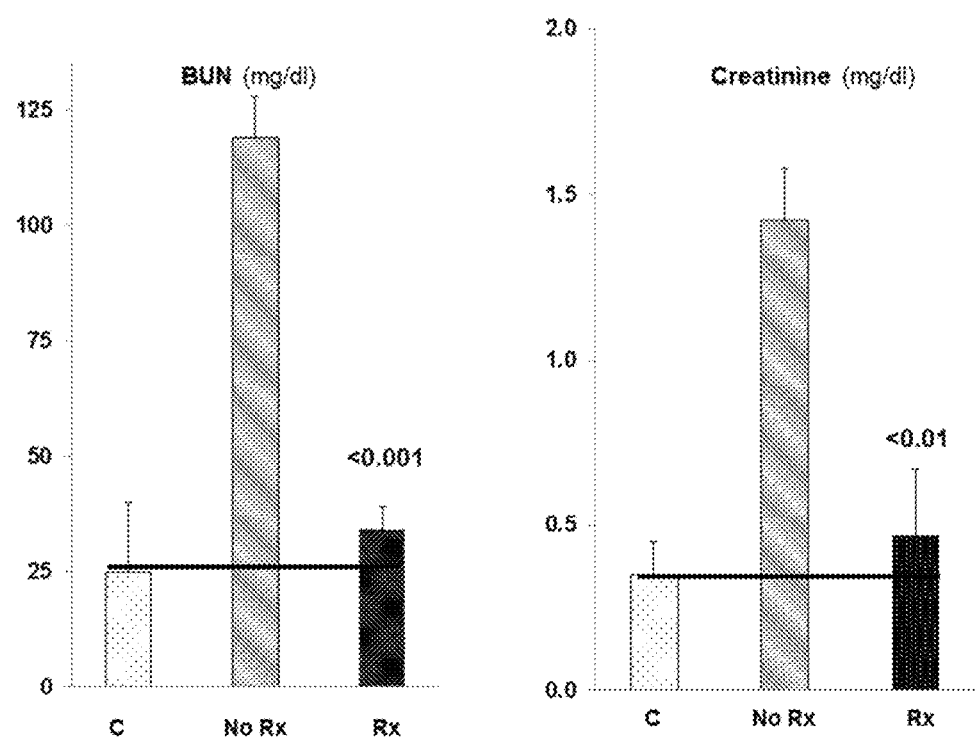
FIG. 13 shows combined N-Mgb 1 SnPP (Rx) treatment confers marked protection against the maleate model of AKI. Maleate injection caused marked BUN and creatinine increases. Treatment (Rx) conferred a near complete protective effect (horizontal lines represent normal BUN and creatinine concentrations). P value vs no treatment (no Rx).

As depicted in FIG. 13, maleate injection caused severe renal injury as denoted by marked BUN/creatinine increases. Pretreatment with N-Mgb+SnPP conferred almost complete protection against this injury as denoted by near normal BUN/creatinine levels.

Figure 14:
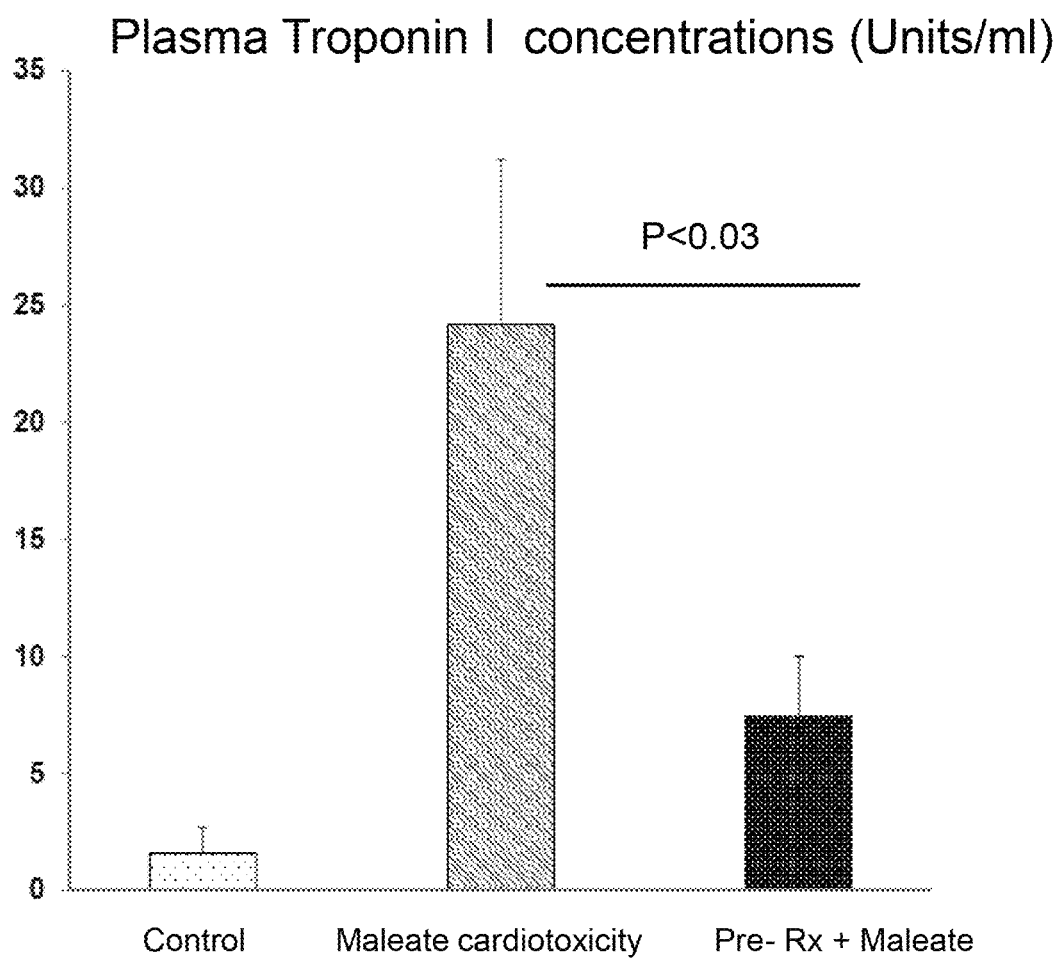
FIG. 14 shows maleate-induced cardiotoxicity is reduced by pretreatment with N-Mgb+SnPP. Mice were treated with 1 mg/Kg N-myoglobin+1 µmole SnPP or IV vehicle injection). Eighteen hrs later, 800 mg/Kg maleate was administered IP. The extent of myocardial injury was determined 18 hrs post maleate injection by measuring plasma troponin I concentrations (by ELISA). Maleate injection caused a 10 fold increase in plasma troponin levels. Pre-treatment with N-Mgb+SnPP reduced the maleate induced troponin increase by 75%.

FIG. 14 shows maleate-induced cardiotoxicity is reduced by pretreatment with N-Mgb+SnPP. Mice were treated with 1 mg/Kg N-myoglobin+1 μmole SnPP or IV vehicle injection). Eighteen hrs later, 800 mg/Kg maleate was administered IP. The extent of myocardial injury was determined 18 hrs post maleate injection by measuring plasma troponin I concentrations (by ELISA). Maleate injection caused a 10 fold increase in plasma troponin levels. Pre-treatment with N-Mgb+SnPP reduced the maleate induced troponin increase by 75%.

Postischemic AKI Model.

Figure 15:
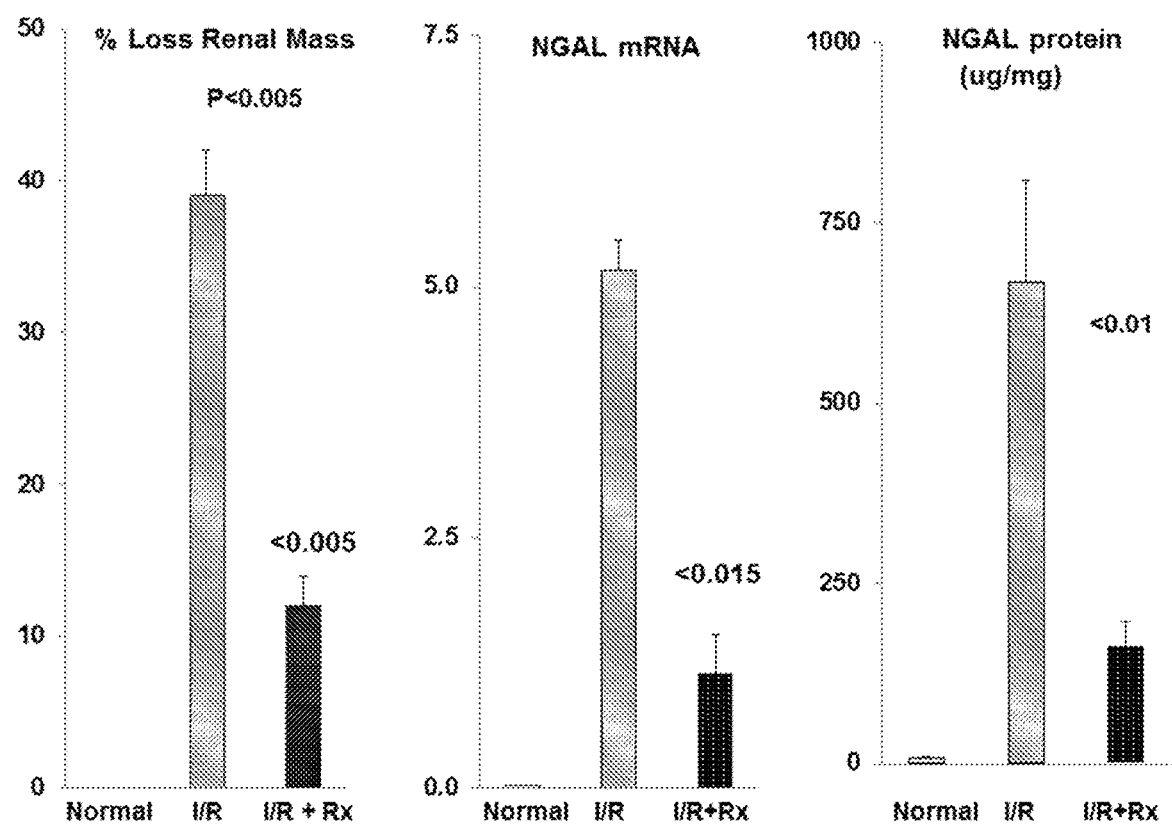
FIG. 15 shows N-Mgb+SnPP (Rx) treatment confers protection against unilateral ischemia-reperfusion (I/R)-induced progressive kidney disease. Mice were subjected to 30 minutes of left renal ischemia with or without N-Mgb–SnPP pretreatment 18 hours earlier. At 2 weeks postischemia, I/R led to a 38% reduction in renal mass (gauged by kidney weight). Pretreatment (Rx) conferred significant protection as gauged by only a 12% reduction in renal mass. Protection was also implied by marked reductions in NGAL mRNA and protein levels in the 2-week post-ischemic left kidneys.

By 2 weeks postischemia, a 38% reduction in postischemic left renal mass was observed in the control unilateral ischemia mice (FIG. 15). In contrast, only a 12% reduction was seen in the mice that had received prophylactic N-Mgb+SnPP treatment (P<0.005). This reduction in renal injury was also denoted by marked reductions in NGAL mRNA and protein levels in the N-Mgb–SnPP pretreatment group (FIG. 15).

Figure 16:
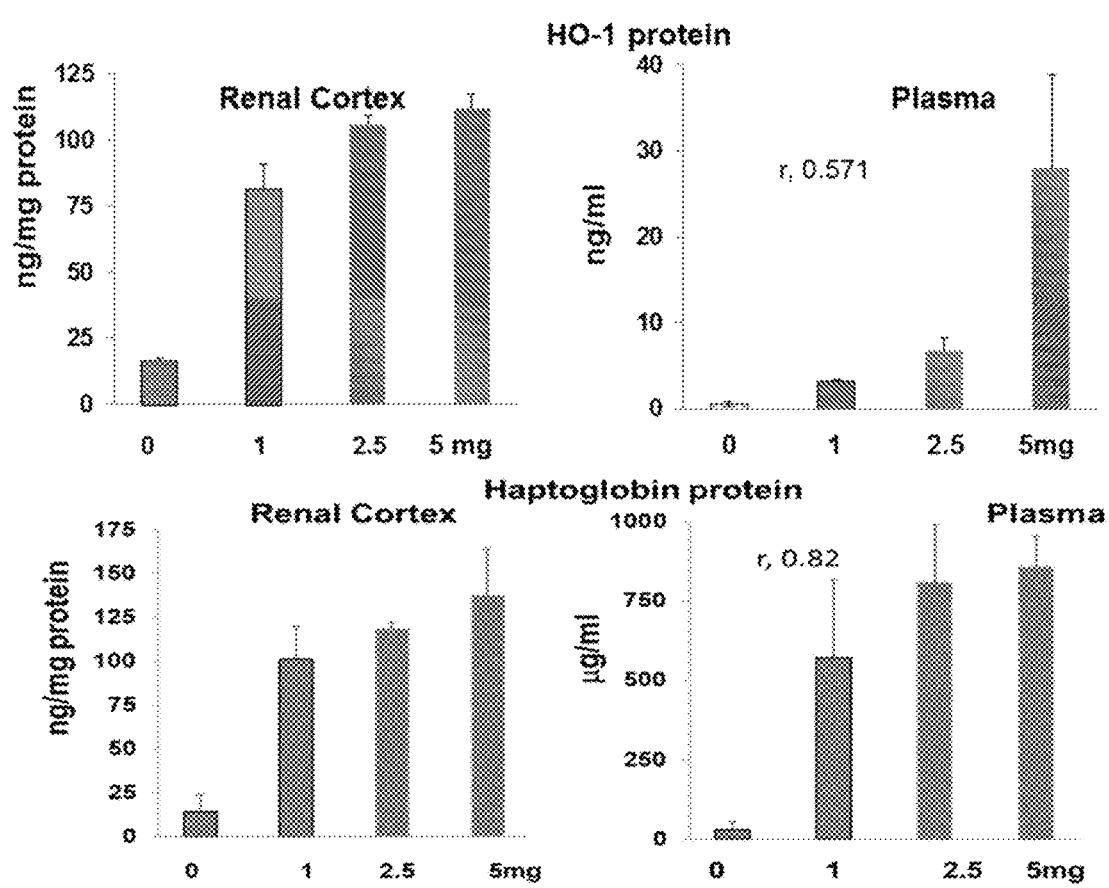
FIG. 16 shows a dose-response relationship between increasing doses of N-Mgb (with a fixed dose of SnPP, 1 umol) and HO-1/haptoglobin protein levels in renal cortex and plasma. Increasing doses of N-Mgb, administered intraperitoneally, led to increasing levels of each protein in plasma and renal cortex. The correlation coefficients for plasma vs renal concentrations were 0.57 and 0.82 for HO-1 and haptoglobin, respectively. The correlations between the dose administered and plasma protein levels were r=0.85 and r=0.75 for HO-1 and haptoglobin, respectively.
Figure 17:
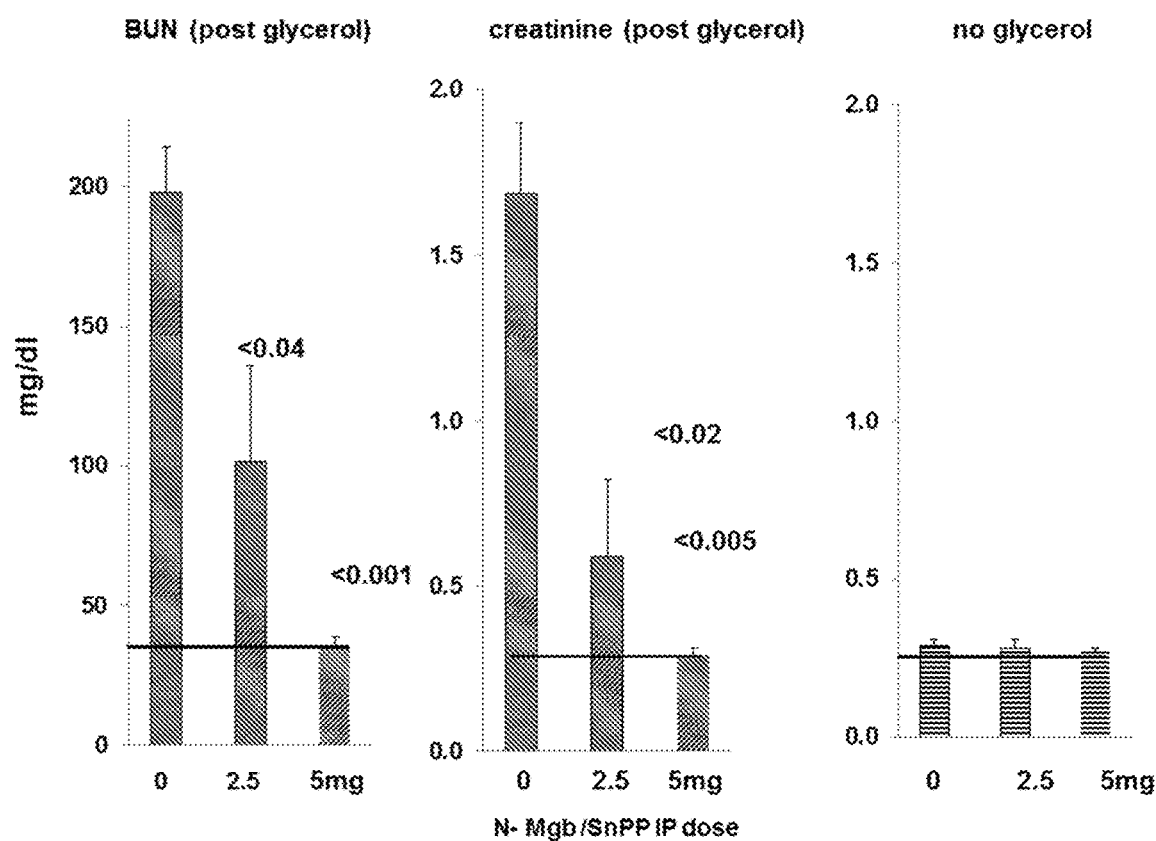
FIG. 17 shows a dose-response relationship between administered IP dose of N-Mgb vs BUN/creatinine concentrations at 18 hours after glycerol administration. Increasing doses of N-Mgb (with a fixed dose of SnPP; 1 umol) led to increasing degrees of protection against glycerol-induced AKI. When analyzed with the results given in FIG. 16, strong direct relationships between plasma and renal cortical HO-1/haptoglobin concentrations and degrees of protection against glycerol-induced AKI are apparent. The horizontal lines indicate normal BUN and creatinine concentrations. As shown in the right panel, the administered doses were well tolerated by the kidney as evidenced by maintenance of normal 18-hour plasma creatinine concentrations across the tested dosage range.

Dose-response relationships between renal cortical and plasma HO-1/haptoglobin levels and degrees of protection against glycerol-induced AKI. As shown in FIG. 16, progressive increases in IP N-Mgb dosages into normal mice produced progressive increases in renal cortical and plasma HO-1 and haptoglobin levels. Significant correlations between plasma and renal cortical HO-1 and haptoglobin levels were observed (e.g., r=0.82 between renal cortical and plasma haptoglobin levels). Furthermore, these increasing N-Mgb doses were associated with progressive (50%; 100%) protection against the glycerol AKI model (FIG. 17). Thus, these data imply that the degree of plasma HO-1 or haptoglobin increases can serve as biomarkers of N-Mgb–SnPP-induced renal gene induction and the degrees of resistance to subsequent ARF. Despite administering 5 mg of N-Mgb (+standard SnPP dose), no evidence of renal injury (normal BUN, creatinine; see FIG. 17, right panel) was observed.

Figure 18:
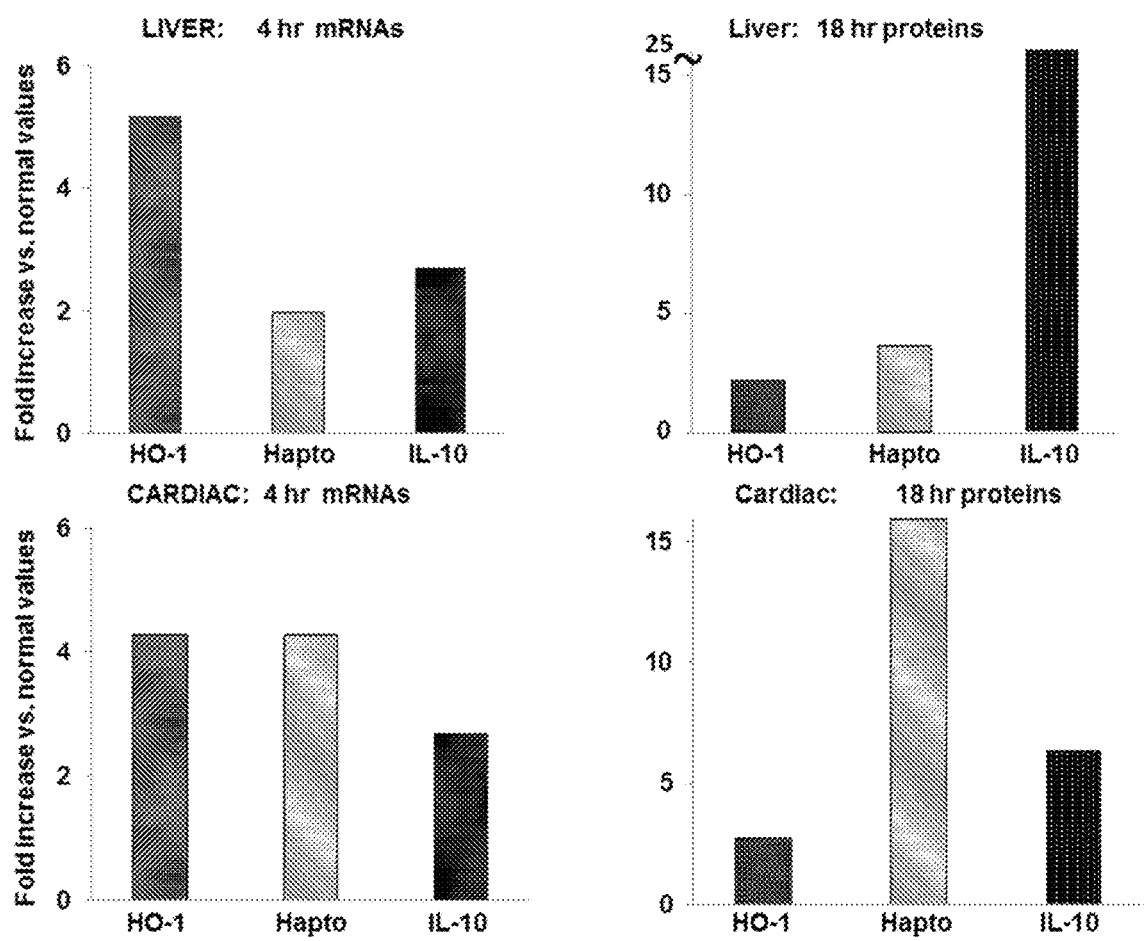
FIG. 18 shows upregulation of HO-1, haptoglobin (hapto), and IL-10 gene expression in liver and heart with combined N-Mgb/SnPP treatment. The degrees of increase with treatment, expressed as a fold increase over control values are presented. Each was increased in both liver (top 2 panels) and heart (bottom 2 panels). Individual values are given in Tables 9 and 10.

Liver assessments. Hepatic HO-1, IL-10, and haptoglobin expressions in liver in response to N-Mgb/SnPP injections. The fold increases over control values for HO-1, IL-10, and haptoglobin mRNAs (4 hours) and for protein levels (18 hours) are depicted in FIG. 18, top panels. Marked increases in each were observed. Individual values for each agent alone or in combination are given in Table 9.

TABLE 9

Liver mRNA and protein levels 4 h (a) and 18 h (b) after Rx treatment

| Measured substance | Control | N-Mgb | SnPP | SnPP 1 N-Mgb |
|---|---|---|---|---|
| (a) 4 h after Rx treatment | | | | |
| Liver mRNA | | | | |
| HO-1 | 1.1 ± 0.12 | 1.83 ± 0.33 | 3.15 ± 0.25 | 5.66 ± 0.29 (<0.001) |
| Haptoglobin | 0.5 ± 0.1 | 0.98 ± 0.1 | 0.32 ± 0.02 | 1.01 ± 0.12 (<0.01) |
| IL-10 | 0.06 ± 0.0.02 | 0.67 ± 0.46 | 0.14 ± 0.1 | 1.12 ± 0.64 (<0.001) |
| Liver protein | | | | |
| HO-1 protein | 10.2 ± 1.2 | 17 ± 2 | 7.4 ± 0.7 | 15.1 ± 1.4 (<0.025) |
| Haptoglobin | 115.3 ± 9.6 | 359.5 ± 39.6 | 130.0 ± 8.9 | 351.0 ± 40.7 (<0.001) |
| IL-10 | 314 ± 36 | 286 ± 32 | 485 ± 47 | 412 ± 34 (=0.1) |
| (b) 18 h after Rx treatment | | | | |
| Liver mRNA | | | | |
| HO-1 | 1.1 ± 0.12 | 0.82 ± 0.07 | 2.56 ± 0.21 | 2.86 ± 0.4 (<0.001) |
| Haptoglobin | 0.5 ± 0.1 | 0.91 ± 0.07 | 0.65 ± 0.17 | 1.19 ± 0.4 (<0.05) |
| IL-10 | 0.06 ± 0.02 | 0.06 ± 0.02 | 0.05 ± 0.01 | 0.06 ± 0.02 (NS) |
| Liver protein | | | | |
| HO-1 protein | 10.2 ± 1.2 | 14.9 ± 0.3 | 18 ± 2.5 | 22.9 ± 1.2 (<0.0001) |
| Haptoglobin | 115.3 ± 9.6 | 358.8 ± 32.8 | 212.0 ± 63.6 | 410 ± 64.3 (<0.001) |
| IL-10 | 314 ± 36 | 5988 ± 549 | 8198 ± 725 | 8015 ± 225 (<0.0001) |

Abbreviations: HO-1, heme oxygenase 1; IL-10, interleukin 10; mRNA, messenger RNA; N-Mgb, nitrited myoglobin; NS, not significant; Rx, treatment; SnPP, tin protoporphyrin.
Individual liver mRNA and protein levels induced by the test agents administered alone or in combination at 4 h (a) and 18 h (b) after injection.

At 4 hours after injection, hepatic HO-1, IL-10, and haptoglobin mRNA levels were significantly higher with combined N-Mgb+SnPP injection vs either agent alone (Table 9). This translated into greater hepatic HO-1, IL-10, and haptoglobin protein increases as assessed at the 18-hour time point (P<0.001 for each protein vs control tissues).

Hepatic ischemic model. Hepatic ischemia induced marked increases in plasma ALT and LDH concentrations (see FIG. 19). The LDH and ALT increases were reduced by 75% and 50%, respectively, with N-Mgb+SnPP pretreatment (corresponding to the hepatic HO-1, haptoglobin, and IL-10 protein increases; Table 9). As shown in FIG. 20 (top), widespread necrosis was observed in gross sections of postischemic liver. Pretreatment with N-Mgb+SnPP led to a much more normal gross hepatic appearance (FIG. 20 (bottom)).

Hepatotoxic Injury.

Figure 19:
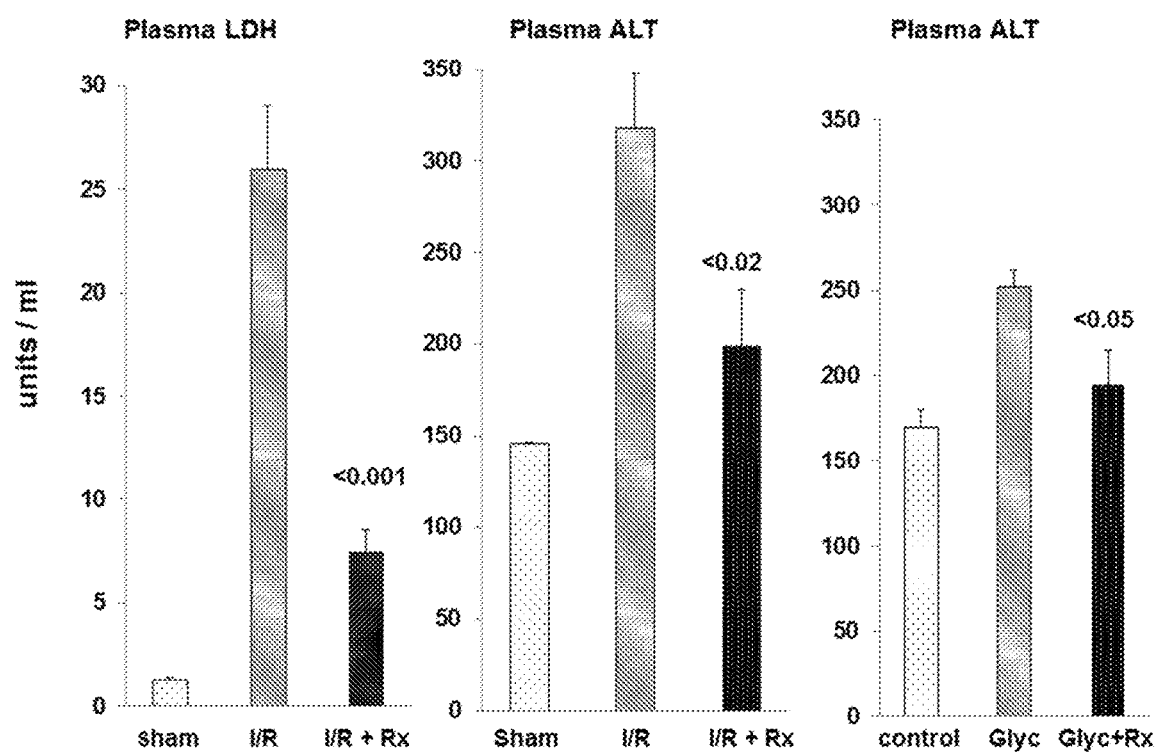
FIG. 19 shows preconditioning with N-Mgb–SnPP mitigates postischemic liver injury and hepatotoxic injury. Degrees of hepatic ischemic-reperfusion (I/R) injury were judged by plasma lactate dehydrogenase (LDH) and alanine aminotransferase (ALT) levels. Pretreatment with N-Mgb–SnPP significantly decreased both LDH and ALT concentrations (left and middle panels). It also decreased the extent of hepatotoxic injury induced by intraperitoneal glycerol injection (right panel).
Figure 20:
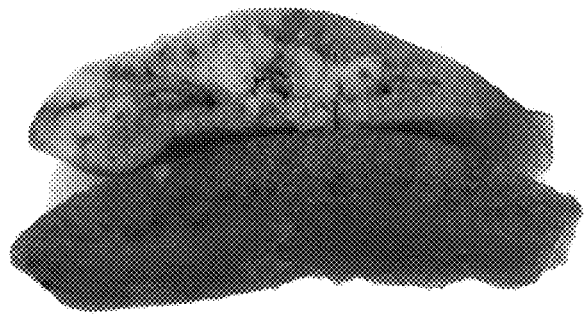
FIG. 20 shows gross appearance of liver sections obtained at 18-hour postischemia without (top) and with (bottom)N-Mgb–SnPP pretreatment. Liver ischemia evoked extensive gross necrosis as evidenced by whitish-gray liver appearance (top). However, with N-Mgb–SnPP pretreatment, the liver retained a near normal appearance (bottom).
Figure 21:
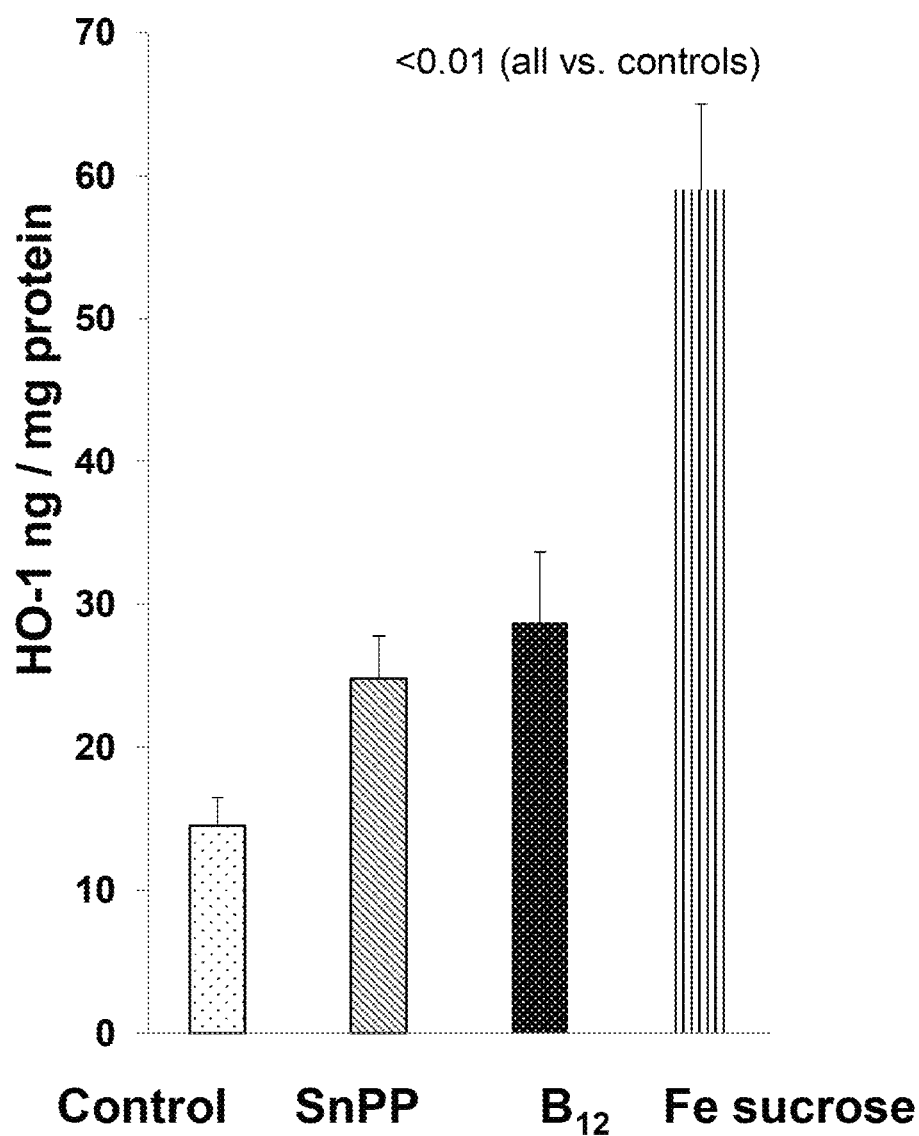
FIG. 21 shows vitamin B12 and Fe sucrose each induces marked HO-1 protein increases within 4 hrs and persists for 18 hrs of their IV injection.
Figure 21:
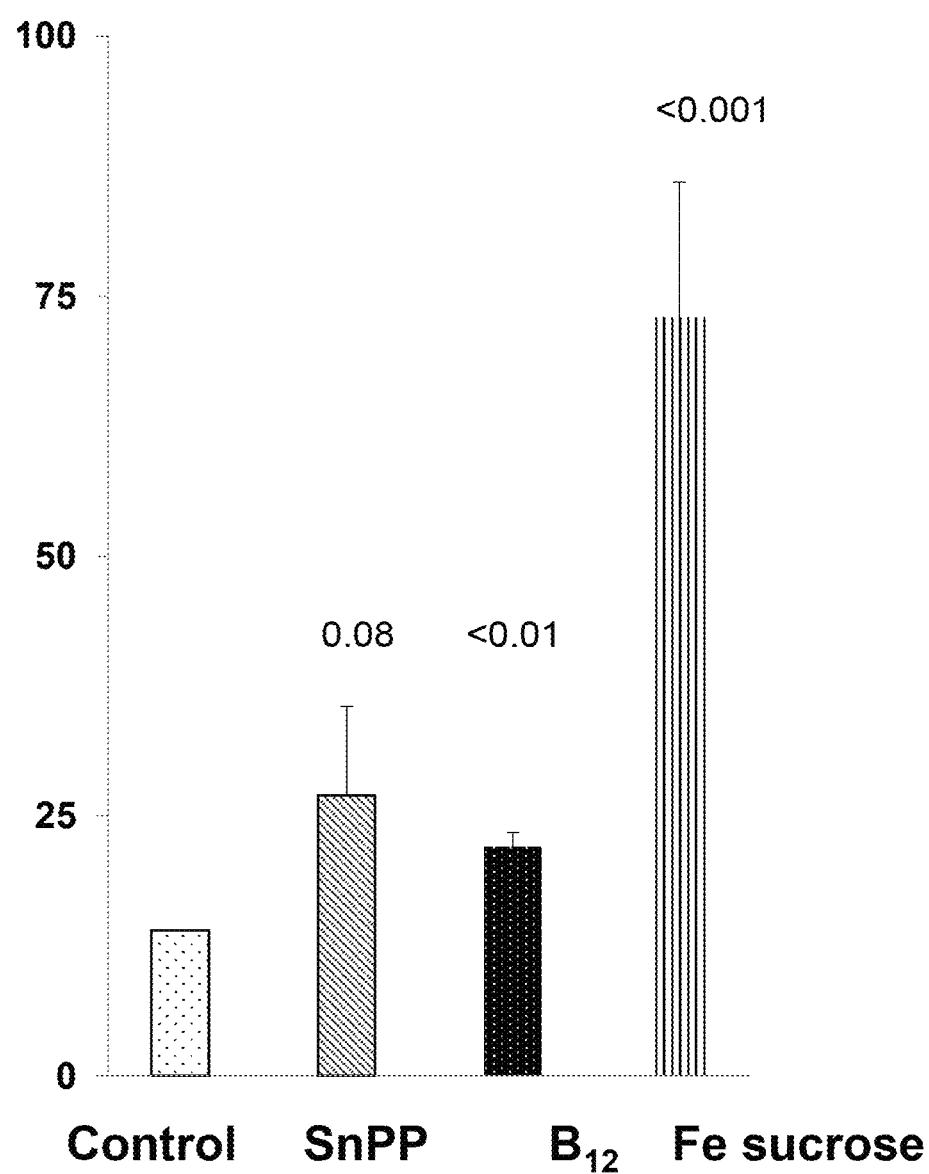

As shown in the right panel of FIG. 19, N-Mgb+SnPP treatment also reduced the extent of IP glycerol-induced liver injury as assessed by plasma ALT levels.

Cardiac HO-1, IL-10, and haptoglobin mRNA and protein levels. As shown at the bottom of FIG. 18, combined N-Mgb+SnPP induced 3- to 4-fold increases in HO-1, haptoglobin, and IL-10 mRNAs at 4 hours, and up to 3- to 15-fold increases in their protein levels at the 18-hour time point. Individual values are given in Table 10.

TABLE 10

Cardiac mRNA and protein levels 4 h (a) and 18 h (b) after Rx treatment

| Measured substance | Control | N-Mgb | SnPP | SnPP + N-Mgb |
|---|---|---|---|---|
| (a) 4 h after Rx treatment | | | | |
| Cardiac mRNA | | | | |
| HO-1 | 0.07 ± 0.01 | 0.09 ± 0.01 | 0.14 ± 0.01 | 0.3 ± 0.01 (<0.001) |
| Haptoglobin | 0.31 ± 0.07 | 0.75 ± 0.10 | 0.52 ± 0.21 | 1.32 ± 0.22 (<0.002) |
| IL-10 | 0.36 ± 0.10 | 0.86 ± 0.11 | 0.58 ± 0.16 | 0.96 ± 0.22 (<0.04) |
| Cardiac Protein | | | | |
| HO-1 | 1.50 ± 08 | 1.64 ± 0.19 | 1.310.13 | 1.54 ± 0.09 (NS) |
| Haptoglobin | 15.6 ± 5.0 | 40.4 ± 8.6 | 19.1 ± 2.1 | 29.4 ± 4.1 (<0.1) |
| IL-10 | 8.1 ± 5 | 21 ± 12 | 15.8 ± 10 | 41 ± 14 (<0.035) |
| (b) 18 h after Rx treatment | | | | |
| Cardiac mRNA | | | | |
| HO-1 | 0.07 ± 0.01 | 0.08 ± 0.01 | 0.09 ± 0.03 | 0.24 ± 0.07 (<0.005) |
| Haptoglobin | 0.31 ± 0.07 | 0.53 ± 0.21 | 0.59 ± 0.17 | 1.28 ± 0.2 (<0.002) |
| IL-10 | 0.36 ± 0.10 | 0.67 ± 0.10 | 0.53 ± 0.10 | 0.64 ± 0.14 (=0.1) |

TABLE 10-continued

Cardiac mRNA and protein levels 4 h (a) and 18 h (b) after Rx treatment

| Measured substance | Control | N-Mgb | SnPP | SnPP + N-Mgb |
|---|---|---|---|---|
| Cardiac protein | | | | |
| HO-1 | 1.5 ± 0.08 | 1.9.7 ± 0.37 | 2.67 ± 0.4 | 4.2 ± 0.98 (<0.01) |
| Haptoglobin | 15.6 ± 5.0 | 249.6 ± 15.0 | 96.1 ± 36.2 | 250.7 ± 37.8 (<0.001) |
| L-10 | 8 ± 5 | 14.5 ± 10 | 23.4 ± 14 | 51.4 ± 19 (<0.035) |

Abbreviations: HO-1, heme oxygenase 1; IL-10, interleukin 10; mRNA, messenger RNA; N-Mgb, nitrited myoglobin; NS, not significant; Rx, treatment; SnPP, tin protoporphyrin.
Individual cardiac mRNA and protein levels induced by the test agents administered alone or in combination at 4 h (a) and 18 h (b) after injection.

In general, far greater mRNA and protein increases were observed with combined agent administration vs either agent alone.

Discussion In 1992, Nath et al. (J Clin Invest 90:267-70) demonstrated that hemoglobin administration in the rat can induce marked protection against subsequent (24 hours later) glycerol-mediated rhabdomyolysis-induced ARF. This protective response was ascribed to heme-mediated HO-1 upregulation, based on 2 pivotal observations: (1) heme pretreatment markedly increased renal HO-1 mRNA and protein levels, as well as HO-1 enzyme activity, and (2) the glycerol model was markedly worsened by administering the potent HO-1 inhibitor, SnPP, at the time of (and after) glycerol injection. From the time of these seminal observations, the role of HO-1 as a potent antioxidant and anti-inflammatory molecule has been well established in multiple models of AKI (e.g., cisplatin, renal ischemia, endotoxemia; reviewed in Nath, Curr Opin Nephrol Hypertens 2014; 23:17-24). Furthermore, its protective effects have been extensively described in diverse forms of extrarenal tissue damage (e.g., brain, liver, heart, organ transplantation). Kusmic et al. J Transl Med 2014; 12:89; Czibik et al. Basic Res Cardiol 2014; 109:450; Sharp et al. Transl Stroke Res 2013; 6:685-92; Le et al. CNS Neurosci Ther 2013; 12:963-8; Huang et al. World J Gastroenterol 2013; 21:2937-48; Liu et al. Crit Care Med 2014; 42:e762-71; Wszola et al. Prog Transplant 2014; 1: 19-26. However, less certain than the existence of HO's protective actions is the exact mechanism by which that protection is effected. Because HO-1 cleavage of the porphyrin ring releases highly toxic catalytic Fe (which exerts direct adverse effects; Zager & Burkhart, Kidney Int 1997; 51:728-38) it is now believed that secondary consequences of increased HO-1 activity are involved. These include the generation of the antioxidants biliverdin and bilirubin, cytoprotective carbon monoxide production, and increased tissue (H) ferritin levels, with its great capacity for catalytic Fe binding. Zarjou et al. J Clin Invest 2013; 123:4423-34; Nath, Curr Opin Nephrol Hypertens 2014; 23:17-24. Additional complexities in interpreting HO-1 involvement in cytoprotection stem from the fact that HO-1 inducers (e.g., heme) also upregulate a number of other cytoprotective pathways, for example, haptoglobin (Zager et al. Am J Physiol 2012; 303:F139-48), hemopexin (Zager et al. Am J Physiol 2012; 303:F1460-72) alpha 1 antitrypsin (Zager et al. PLoS One 2014; 9:e9838) and IL-10 (as shown in the present disclosure). This complicates interpretation of HO-1 effects on tissue injury given the presence of multiple upregulated tissue protective proteins.

The interplay of SnPP and HO-1 is also complex. First, as a competitive inhibitor of HO-1, SnPP administration can secondarily increase HO-1 mRNA and protein levels either by enzyme "feedback inhibition" or by the induction of a mild pro-oxidant state with counter-balancing HO-1 production (e.g., Kaizu et al. Kidney Int 2003; 63:1393-403). Second, the Sn moiety of SnPP may independently upregulate HO-1 via direct pro-oxidant effects. Barrera-Oviedo et al. Ren Fail 2013; 35:132-7. Third, whenever considering the effects of SnPP, it is important to recognize that secondary HO-1 induction could potentially be offset by SNPP-induced HO-1 inhibition. However, it is noteworthy that SnPP has a relatively short half-life (2-4 hours; Berglund et al. Hepatology 1988; 8:625-31). Thus, delayed HO-1 increases (e.g., 18 hours after glycerol administration or N-Mgb–SnPP treatment) should be free to exert its biological effects because of prior SnPP elimination. This concept is supported by observations that at 24 hours after SnPP administration, upregulated HO-1 was able to exert a cytoprotective effect (e.g., against ischemic ARF; Juncos et al. Am J Pathol 2006; 169:21-31; Kaizu et al. Kidney Int 2003; 63:1393-403).

Figure 8:
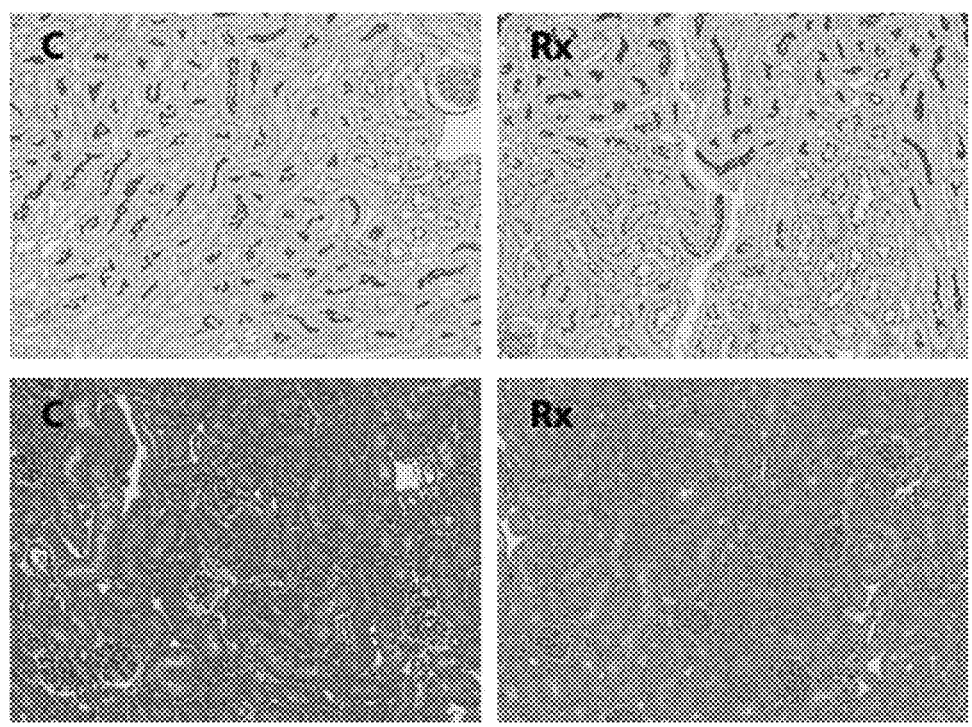
FIG. 8 shows renal histology 18 hours after N-Mgb–SnPP administration. The top 2 panels are PAS-stained kidney sections from a control mouse (C) and a mouse 18 hour after N-Mgb–SnPP treatment (Rx). The tubular epithelium from treated mice maintains a normal histologic appearance with a completely intact brush border (dark staining of luminal membrane). The bottom 2 panels depict hematoxylin and eosin-stained sections. No histologic injury is apparent with N-Mgb–SnPP pretreatment.

In light of the previously mentioned considerations, it was hypothesized that a combination of N-Mgb+SnPP might induce either additive or synergistic increases in HO-1 and in other redox sensitive cytoprotective proteins (e.g., haptoglobin and IL-10). This hypothesis was tested by measuring HO-1, haptoglobin, and IL-10 mRNA and protein levels at 4 and 18 hours after N-Mgb, SnPP, or N-Mgb+SnPP injection. As shown in FIGS. 7-9, combined therapy generally induced synergistic or additive responses. For example, at 4 hours after injection, a 20-fold increase in HO-1 mRNA was observed, more than doubling the increases seen with either N-Mgb or SnPP alone. At 18 hours, this early mRNA increase translated into 7-fold HO-1 protein increases. Qualitatively similar results were observed with IL-10. Particularly noteworthy was a massive (20-fold) increase in haptoglobin protein at 18 hours after N-Mgb–SnPP administration. However, in this case, it appeared that it was N-Mgb rather than an N-Mgb–SnPP interaction, which was largely responsible, given that N-Mgb alone vs N-Mgb+SnPP induced comparable renal haptoglobin increases. Clearly, additional cytoprotective redox sensitive proteins, other than HO-1, IL-10, and haptoglobin, may also have been induced by the N-Mgb–SnPP protocol (e.g., al antitrypsin, hemopexin, hepcidin). Thus, it seems logical that multiple cytoprotective proteins could act in concert to mitigate cell injury responses.

Having observed dramatic renal cortical increases in cytoprotective proteins after N-Mgb–SnPP administration, the latter's effectiveness in protecting against 3 forms of AKI was tested. FIG. 12 depicts the results in the glycerol model. As shown, SnPP administration alone induced no significant reductions in BUN or creatinine levels. When N-Mgb alone was administered, a modest protective effect was observed. However, when administered together, N-Mgb+SnPP pretreatment evoked essentially complete functional protection as indicated by normal BUN and plasma creatinine concentrations at 18 hours after glycerol injection. Furthermore, near normal renal histology was observed. Thus, these findings underscore the principle that synergistic increases in cytoprotective proteins can translate into synergistic protection against ARF.

To further explore the scope of N-Mgb–SnPP-mediated protection, the maleate model of proximal tubular ATP depletion-mediated ARF was used. Again, dramatic or near complete protection was observed (FIG. 13). Because it is now well recognized that AKI can initiate the onset of progressive chronic renal disease, whether N-Mgb–SnPP pretreatment could abrogate this process in a previously published unilateral postischemic renal injury model (Zager et al. Kidney Int 2013; 84:703-12; Zager et al. Am J Physiol Renal Physiol 2014; 307:F856-68) in which a 40% loss of renal mass normally results in 2 weeks was assessed. As shown in FIG. 15, postischemic injury was markedly attenuated with N-Mgb–SnPP pretreatment as evidenced by a reduction in renal mass loss from 38% to 12%, and marked reductions in NGAL mRNA and protein levels. Thus, in each of 3 heterogeneous AKI models, dramatic protection was observed. Although the kidney has the largest exposure to the 2 test agents (e.g., via rapid filtration, Mgb endocytosis), virtually all cells are transiently exposed to them after their IV injection. Furthermore, protoporphyrins can bind to and be taken up by a variety of cells. Anderson et al. J Pharmacol Exp Ther 1984; 228:327-33. Thus, it was questioned whether the disclosed N-Mgb–SnPP regimen might also upregulate protective responses in extrarenal organs. Indeed, this was the case, given that both hepatic and cardiac tissues manifested HO-1, IL-10, and haptoglobin mRNA and protein increases at both 4 and 18 hours after N-Mgb–SnPP injection (as presented in Tables 9 and 10). That N-Mgb alone could induce a response in extrarenal tissues was surprising, given that megalin-cubilin-mediated endocytosis is thought to be a renal specific pathway. This either suggests potential extrarenal uptake, possibly via scavenger receptors, (Canton et al. Nat Rev 2013; 13:621-34) or that when present in the microcirculation, N-Mgb and SnPP are able to activate intracellular cytoprotective genes. To test whether extrarenal protection might result, the impact of N-Mgb+SnPP pretreatment on the extent of postischemic hepatic injury was assessed. As presented in FIG. 18, marked reductions in both LDH and ALT plasma concentrations were observed. Furthermore, obvious protection was indicated by the gross appearance of postischemic hepatic tissues (FIG. 19). To further test hepatic resistance to injury, mice were subjected to an IP injection of glycerol, which on reaching the liver through the portal circulation induces modest hepatic damage. Within 4 hours of IP glycerol injection, increases in plasma ALT resulted, which were largely abrogated by prior N-Mgb–SnPP injection.

It has previously been demonstrated that plasma levels of either haptoglobin or HO-1 can serve as biomarkers of renal cortical haptoglobin and HO-1 increments in the setting of ARF. Z Zager et al. Am J Physiol 2012; 303:F139-48; Zager et al. J Am Soc Nephrol 2012; 23:1048-2057. Thus, it was questioned whether plasma haptoglobin and HO-1 might also serve as biomarkers for induction of these proteins in kidney after N-Mgb–SnPP administration and for the emergence of the cytoresistant state. This indeed was the case. As shown in FIG. 16, increasing doses of N-Mgb–SnPP induced dose-dependent increases in plasma haptoglobin and HO-1 levels, and these increases directly correlated with renal cortical haptoglobin and HO-1 content. Furthermore, striking inverse relationships between N-Mgb–SnPP-induced plasma HO-1 and plasma haptoglobin increases and postglycerol BUN concentrations were observed (r, −0.79/r, −0.71 for BUN vs plasma HO-1 and haptoglobin levels, respectively). Thus, plasma HO-1/haptoglobin increments would likely confirm biological activity of N-Mgb–SnPP in clinical trials, and the degrees of HO-1 and haptoglobin plasma increase might also be predictive of degrees of resistance to subsequent AKI.

An obvious concern by applying this prophylactic strategy to patients is potential renal and/or extrarenal toxicities. However, in this regard, it is noteworthy that SnPP has already been shown to be well tolerated in humans (e.g., Berglund et al. Hepatology 1988; 8:625-31; Kappas et al. Pediatrics 1988; 81:485-97; Reddy et al. J Perinatol 2003; 23: 507-12). Furthermore, it was previously documented in a cell culture system that nitrite addition markedly reduces myoglobin's cytotoxic effects by 75% (unpublished data, 2014). To assess the potential in vivo margin of safety for N-Mgb+SnPP (see Supplemental FIGs.), the maximal amount of N-Mgb that could be given to mice before nephrotoxicity was observed was tested. Up to 25 times the employed N-Mgb dose (with a constant SnPP dose) could be administered (over 2 hours) without induction of nephrotoxicity (normal BUN and creatinine, 18 hours later). Finally, neither the standard N-Mgb–SnPP dosage (1 mg N-Mgb/1 mmol SnPP) nor 5 mg IP N-Mgb (FIG. 17) induced overt renal injury (18 hour BUN/creatinine, or histology), nor did it raise hepatic ALT or cardiac troponin levels. In concert, these data indicate usefulness in clinical application.

Conclusions.

Administration of N-Mgb, along with an inhibitor of its degradation (SnPP), leads to dramatic increases in a number of cytoprotective proteins in kidney. The potency of this response is indicated by observations that the documented renal HO-1 protein increases were 15 times greater than that which has been achieved with bardoxolone methyl, a well recognized Nrf-2-mediated HO-1 inducer. Wu et al. Am J Physiol 2011; 300: F1180-92. Within 18 hours of its administration, N-Mgb+SnPP evoked dramatic protection against 3 diverse models of AKI: glycerol-induced rhabdomyolysis, maleate-induced proximal tubule ATP depletion, and postischemic AKI progression to CKD. Surprisingly, N-Mgb+SnPP administration also induced synergistic increases in cytoprotective proteins in liver, leading to dramatic protection against hepatic ischemic-reperfusion injury and hepatotoxicity. Finally, N-Mgb+SnPP can upregulate cytoprotective proteins in heart, suggesting cardiac protection, and thus, broad ranging cytoprotective effects. Of note, each of these responses was induced in the absence of discernable renal, hepatic, or cardiac toxicity. Thus, these data suggest that N-Mgb+SnPP coadministration can provide a clinical prophylactic strategy for protecting against both renal and extrarenal injuries, such as may result during cardiopulmonary bypass, aortic aneurysm repair, or other complex, high-risk surgeries. Thus, this strategy could potentially meet a number of significant unmet clinical needs.

Example 5

Two mongrel dogs, one male, one female, had baseline blood drawn for measurement of plasma heme oxygenase 1 (HO-1; canine ELISA) BUN, plasma creatinine, and lactate dehydrogenase (LDH) levels. A baseline spot urine sample was also obtained for HO-1 assay. Dog 1 then received a 50 ml/50 min infusion of normal saline/40 mM NaHCO$_3$ containing 5 mg/Kg of nitrited canine myoglobin+3.75 mg/Kg of SnPP. Dog 2 received 2.5 mg/Kg canine N-myoglobin+

7.5 mg/Kg SnPP. Four and 26 hrs later, repeat blood samples were obtained. A second urine sample was collected at 26 hrs post infusion. As shown in Table 11, the infusion evoked massive increases in plasma and urinary HO-1 concentrations in the absence of renal injury (based on pre and BUN and plasma creatinine levels). LDH values remained unchanged, implying an absence of obvious renal/extrarenal tissue injury.

TABLE 11

HO-1 Induction in Dogs

| | Dog 1 (male) | Dog 2 (female) |
|---|---|---|
| Baseline BUN (mg/dl) | 20 → | 28 → |
| 26 hr BUN | 28 | 23 |
| Baseline Creatinine (mg/dl) | 0.5 → | 0.7 → |
| 26 hr Creatinine | 0.5 | 0.6 |
| Baseline LDH (units/dl) | 0.4 → | 0.31 → |
| 26 hr LDH | 0.2 | 0.31 |
| Baseline Plasma HO-1 (mg/ml) | 1.3 → | 4.0 → |
| 4 hr Plasma HO-1 | 34 → | 44.7 → |
| 26 hr Plasma HO-1 | 155 | 90.6 |
| Baseline Urine HO-1 (mg/mg cr) | 2 → | 0.8 → |
| 26 hr Urine HO-1 | 18.8 | 11.1 |

Example 6

Effects of Fe sucrose and cyanocobalamin (Vitamin $B_{12}$) on heme oxygenase 1 induction in kidney. Heme oxygenase-1 (HO-1) upregulation is a critical mediator of N-myoglobin/SnPP's cytoprotective activity in kidney and extra-renal organs. Hence, additional agents were sought that can induce HO-1 up-regulation, and thus, contribute to the emergence of tissue protection against toxic and ischemic forms of injury. Because Fe is the critical mediator of N-Mgb's activity, the impact of an Fe-carbohydrate polymer (Fe sucrose; molecular weight ranging from 34-61 kDa) on HO-1 levels was assessed.

As an alternative and/or complementary strategy, the impact of cyanocobalamin (vitamin B12) on HO-1 induction in kidney was studied. The rationale for B12 testing is that both cobalt and cyanide can independently induce HO-1. Thus, B12 could represent a safe method to administer both cyanide and cobalt, and as a single agent, since both are integral parts of the B12 molecule.

Methods.

Male CD-1 mice (25-40 grams) Charles River, Wilmington, Mass.) were used for all experiments. They were housed under standard vivarium conditions with free food and water access. All experiments were approved by the Fred Hutchinson Cancer Research Center IACUC in accordance with NIH guidelines.

Effects of Fe sucrose (FeS)/tin protoporphyrin (SnPP) on AKI severity. Maleate model of AKI. When injected into rodents, maleate undergoes relatively selective proximal tubule cell uptake via organic anion transporters. Once intracellular accumulation occurs, maleate is a preferred substrate for succinyl-CoA:3-oxoacid CoA transferase. This results in the formation of maleyl-coenzyme A. With subsequent conversion of maleyl CoA into a stable thioether, severe coenzyme A (CoA) depletion results. Ample levels of CoA are essential for fatty acid "activation", allowing for their subsequent metabolism through the Krebs cycle, yielding ATP. In the absence of this process, proximal tubule ATP depletion and cell injury result. Additionally, maleate conjugates the sulfhydryl group of glutathione (GSH), culminating in GSH depletion and potential oxidant tubular stress.

The following experiment tested whether FeS, SnPP or combined FeS+SnPP can mitigate this form of acute kidney injury (AKI). Twenty seven mice were subjected to 200 μL IV tail injections of one of the following: 1) vehicle (phosphate buffered saline, PBS; n, 10); 2) 1 mg FeS (American Regent (Shirley, N.Y.; n, 3); 3) 1 μmole SnPP (Frontier Scientific, Logan, Utah; n 7), or FeS+SnPP, n, 7). Eighteen hrs later, all mice received an IP injection of Na maleate (800 mg/Kg; in 500 ul of PBS). Eighteen hrs later, the mice were deeply anesthetized with pentobarbital (50 mg/Kg IP), the abdominal cavities were opened, and blood samples were obtained from the abdominal vena cava. The severity of kidney injury was assessed by determining plasma blood urea nitrogen (BUN) and plasma creatinine (PCr) concentrations.

Renal ischemic-reperfusion injury (IRI) model of AKI. The following experiment assessed whether combination FeS+SnPP can mitigate the renal artery occlusion model of AKI. Mice received 200 μl tail vein injections of either PBS (n, 9) or FeS+SnPP (n, 8), as noted above. Eighteen hrs later, the mice were deeply anesthetized with pentobarbital (40-50 mg/Kg IP), the abdominal cavities were opened, the renal pedicles were identified and both were occluded with microvascular clamps. Body temperature was maintained at 36-37° C. throughout. Following 22 minutes of bilateral renal ischemia, the clamps were removed, uniform reperfusion was visually confirmed by the reappearance of a normal renal color (loss of tissue cyanosis), and then the abdominal cavities were closed in two layers with silk suture. Eighteen hrs later, the mice were re-anesthetized, the abdominal cavities were re-opened, and terminal blood samples were obtained from the vena cava. The severity of renal injury was determined by BUN and PCr concentrations.

FeS/B12 effects on the severity of AKI. Glycerol model of AKI. Mice received tail vein injections of either PBS vehicle (n 6), or combination FeS+1 μmole B12 (n, 6; B12 from Alfa Aesar, Ward Hill, Mass.). Eighteen hrs later, the mice were lightly anesthetized with isoflurane, and then the glycerol model of rhabdomyolysis AKI was induced (9 ml/Kg 50% glycerol, administered in two equally divided IM injections into the upper hind limbs). Eighteen hrs post glycerol injection, the mice were deeply anesthetized with pentobarbital and terminal vena cava blood samples were obtained. Renal injury severity was gauged by terminal BUN and PCr concentrations.

Maleate model of AKI. Mice received tail vein injections of either combination of FeS+B12 or vehicle (n, 6 per group). Eighteen hrs later they received IP maleate injections, as noted above. The severity of AKI was determined 18 hrs post maleate injection by terminal BUN and PCr assessments.

Effects of FeS, SnPP, and B12 on renal cortical induction of heme oxygenase 1 (HO-1). The following experiments assessed the effects of FeS, SnPP, and B12 on the possible induction of the cytoprotective protein HO-1. To this end, mice were injected with each of these agents, as noted above. Either 4 or 18 hrs later, they were anesthetized and the kidneys were removed through a midline abdominal incision. The renal cortices were dissected on ice and then extracted for protein and mRNA. The samples were then assayed for HO-1 protein by ELISA, and HO-1 mRNA by RT-PCR, factored by GAPDH levels. Five normal mice provided control values.

Results.

Figure 22:
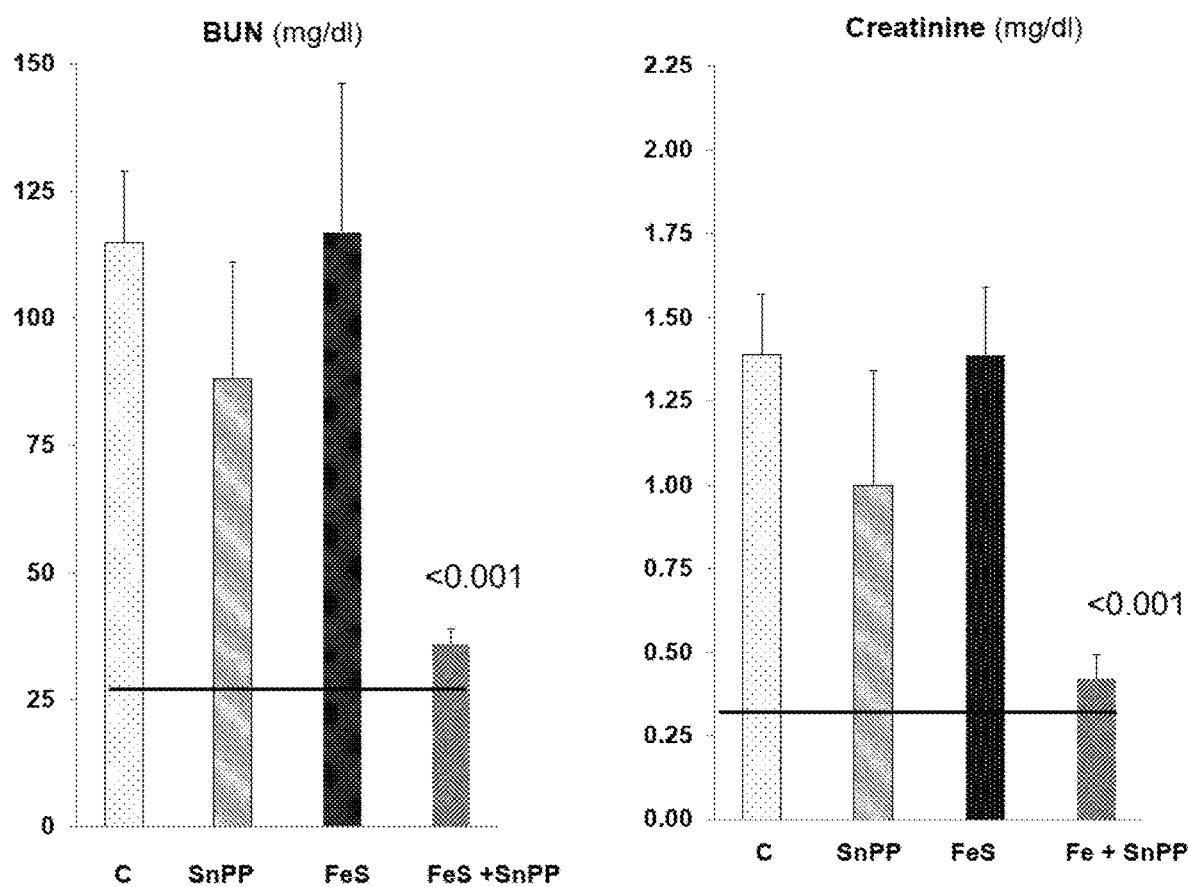
FIG. 22 shows maleate injection caused severe AKI as denoted by marked BUN and PCr increases over maleate injected controls (C). Neither SnPP alone nor FeS alone significantly altered the severity of renal injury. However, combined FeS+SnPP conferred marked protection, as denoted by 75% reductions in BUN/PCr concentrations (the horizontal lines represent the means of BUN/PCr levels in normal mice).

Effects of FeS/SnPP on the severity of AKI. Maleate-induced AKI: As shown in FIG. 22, maleate injection caused severe AKI as denoted by marked BUN and PCr increases over maleate injected controls (C). Neither SnPP alone nor FeS alone significantly altered the severity of renal injury. However, combined FeS+SnPP conferred marked protection, as denoted by 75% reductions in BUN/PCr concentrations (the horizontal lines represent the means of BUN/PCr levels in normal mice).

Figure 23:
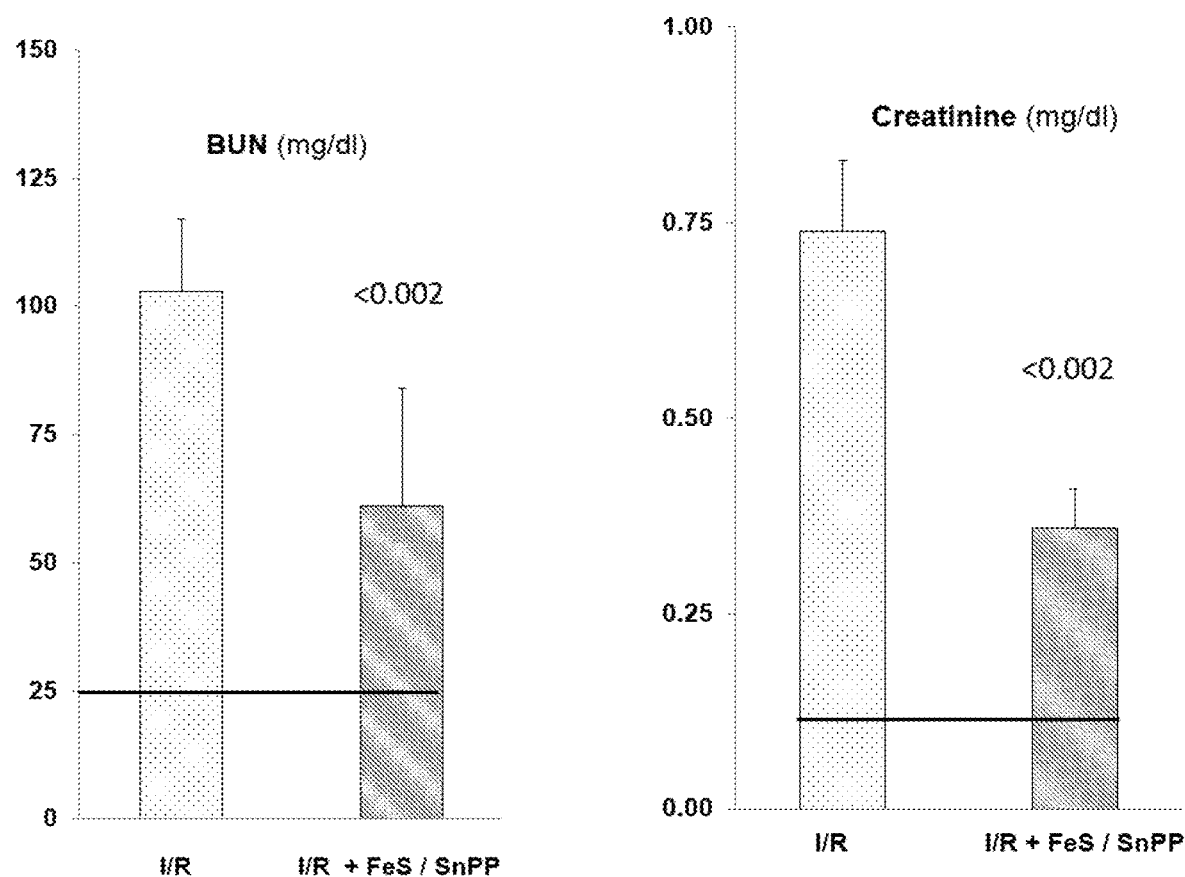
FIG. 23 shows that within 18 hrs of inducing IRI, 4 fold elevations in BUN and PCr concentrations resulted. Pretreatment with FeS+SNPP conferred significant protection, lowering the BUN and PCr levels by 50%. The horizontal lines represent mean BUN/PCr levels in normal mice.

Renal ischemia-reperfusion (IRI) induced AKI: Within 18 hrs of inducing IRI, 4 fold elevations in BUN and PCr concentrations resulted (FIG. 23). Pre-treatment with FeS+SNPP conferred significant protection, lowering the BUN and PCr levels by 50%. The horizontal lines represent mean BUN/PCr levels in normal mice.

Figure 24:
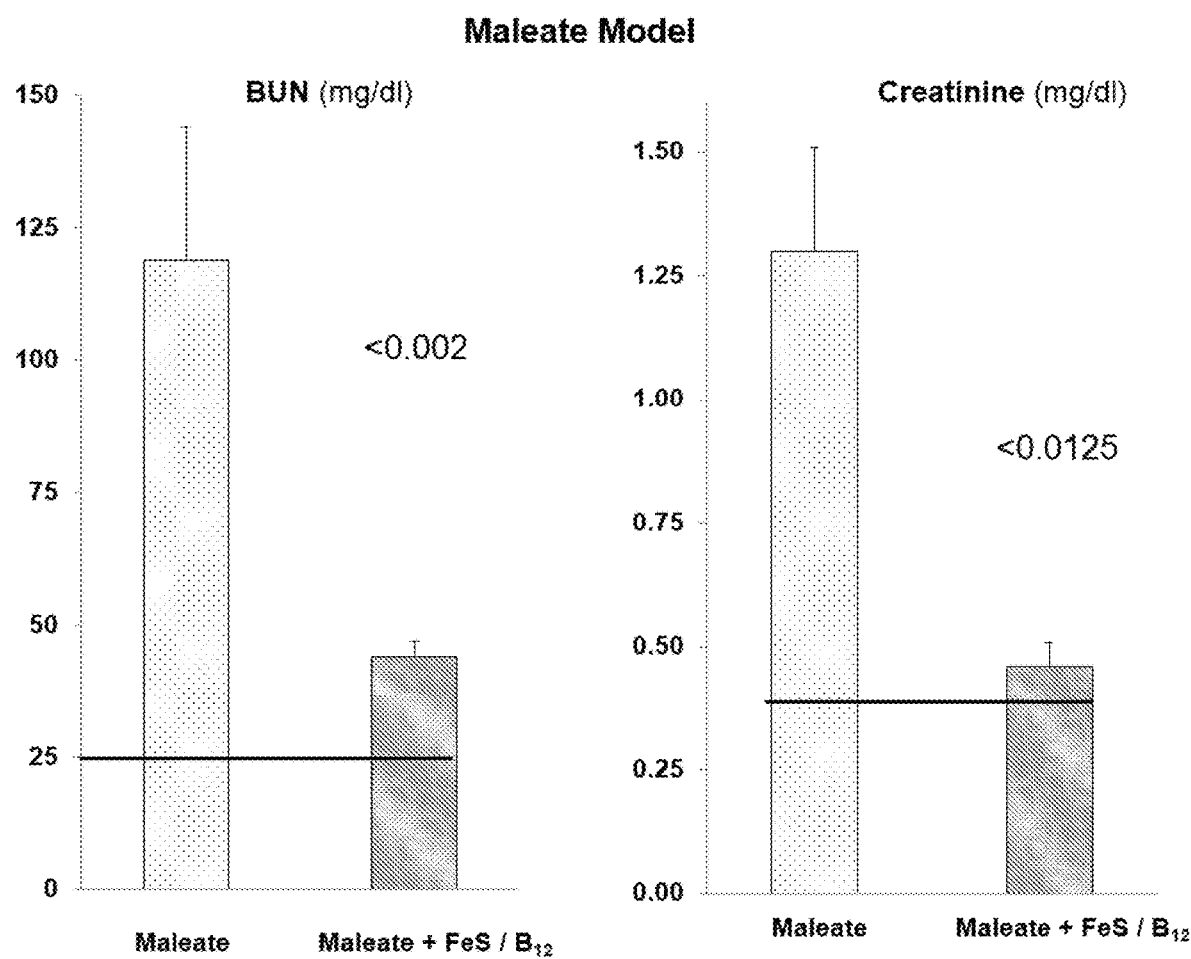
FIG. 24 shows that maleate injection induced severe AKI. Pre-treatment with FeS+B12 markedly mitigated this injury, as denoted by BUN/PCr reductions. The horizontal lines represent mean BUN/PCr levels in normal mice.

Effects of FeS/B12 on AKI severity. Maleate induced AKI: Again, maleate injection induced severe AKI (FIG. 24). Pre-treatment with FeS+B12 markedly mitigated this injury, as denoted by BUN/PCr reductions. The horizontal lines represent mean BUN/PCr levels in normal mice.

Figure 25:
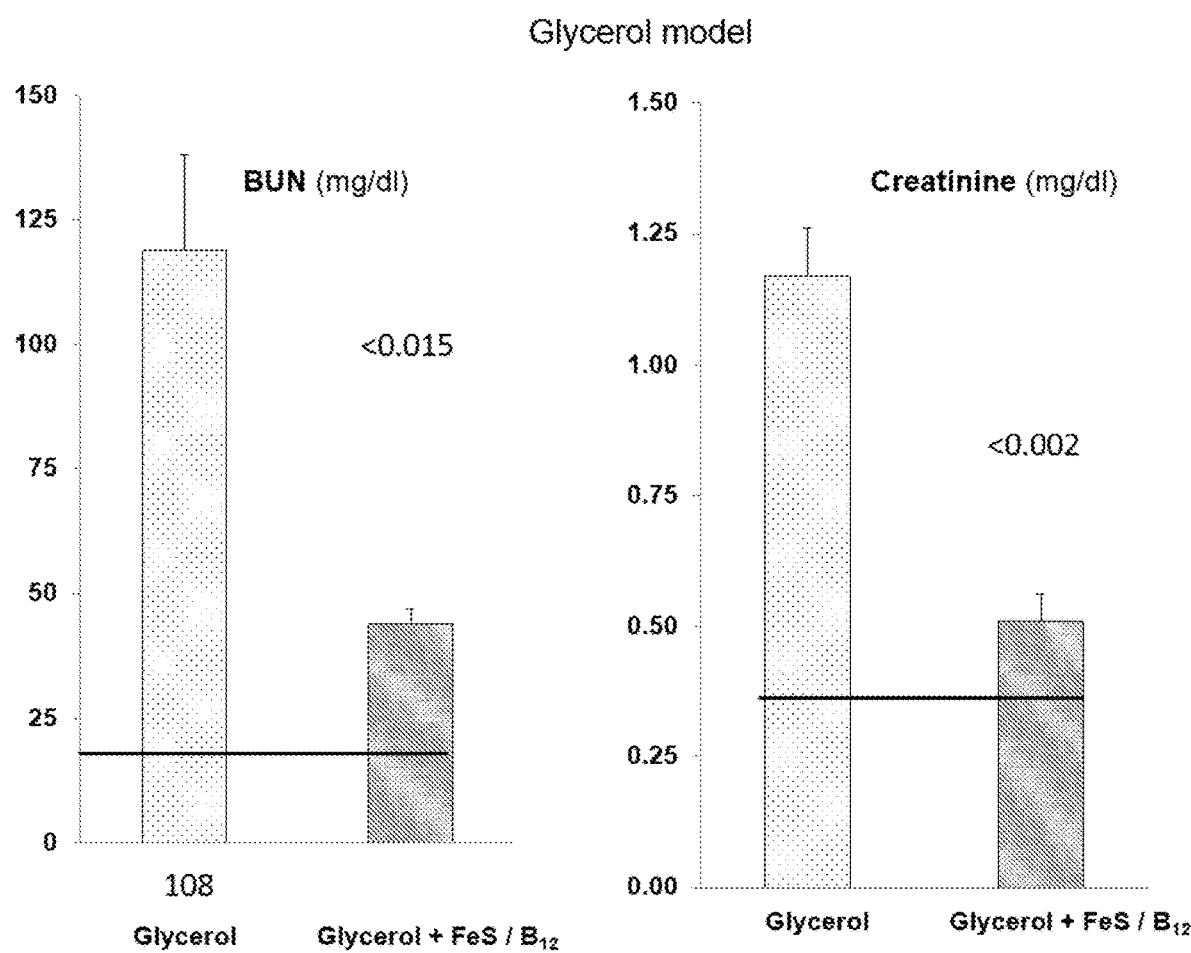
FIG. 25 shows severe renal failure resulted within 18 hrs of glycerol injection. Pre-treatment with FeS+B12 conferred substantial functional protection, as denoted by marked reductions in both 18 hr BUN and PCr concentrations. The horizontal lines represent mean BUN/PCr levels for normal mice.

Glycerol model of AKI: Severe renal failure resulted within 18 hrs of glycerol injection (FIG. 25). Pre-with FeS+B12 conferred substantial functional protection, as denoted by marked reductions in both 18 hr BUN and PCr concentrations. The horizontal lines represent mean BUN/PCr levels for normal mice.

Figure 26:
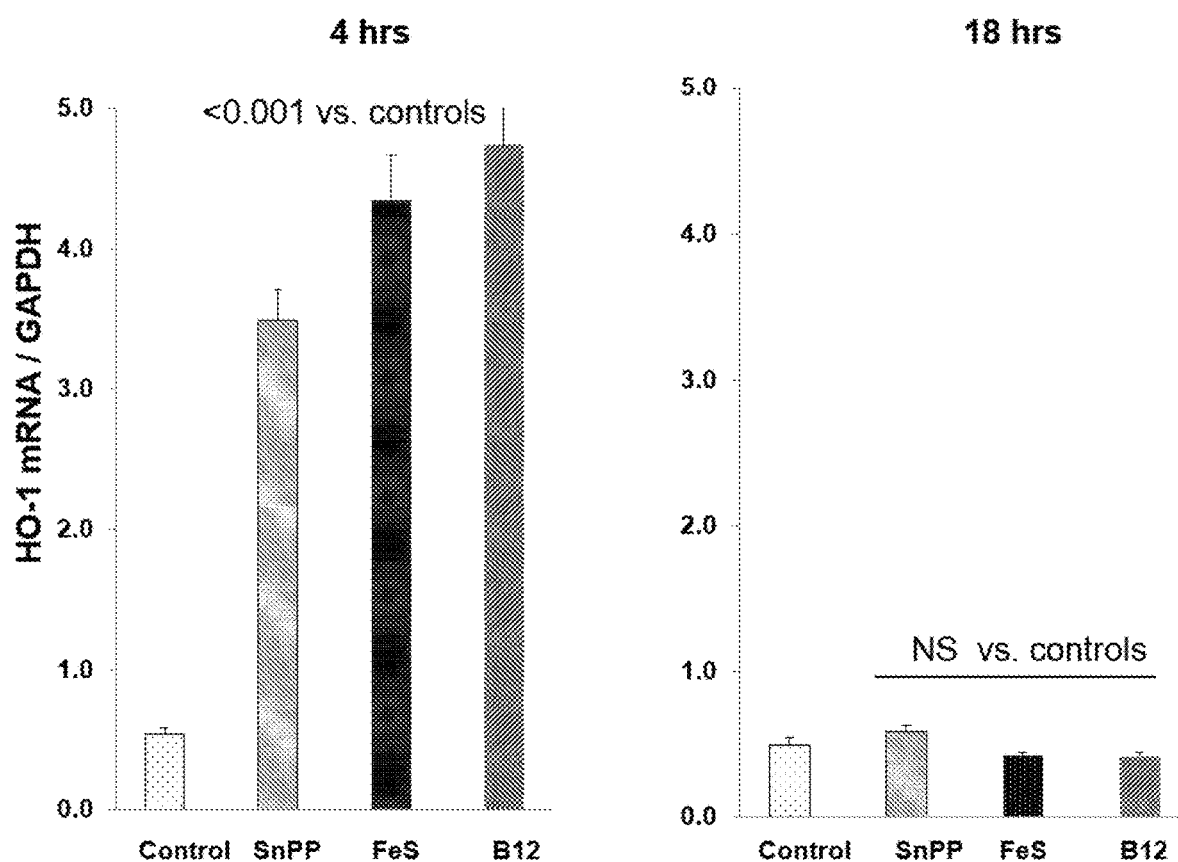
FIG. 26 shows marked and significant increases in HO-1 mRNA, as assessed 4 hr post injection. By 18 hrs, HO-1 mRNA levels returned to normal values.
Figure 27:
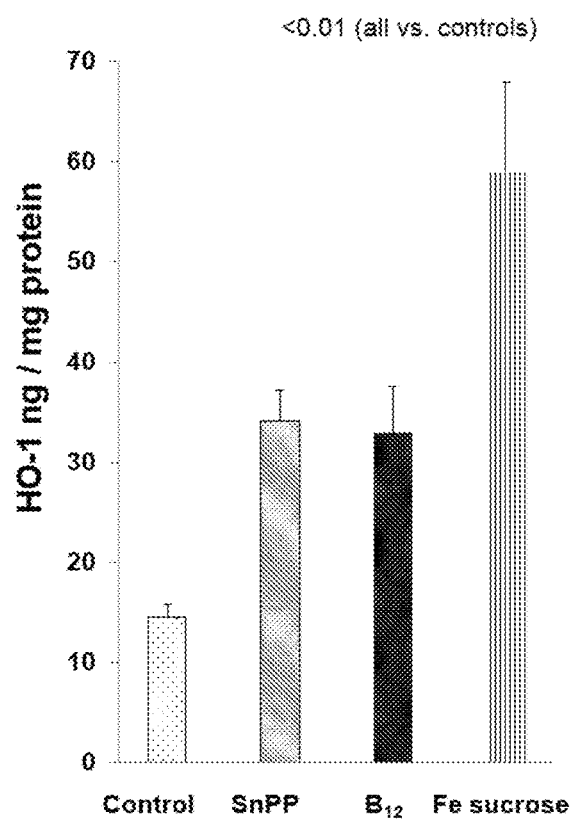
FIG. 27 shows the 4 hr mRNA increases are correlated with a significant increase in HO-1 protein levels. These levels remained elevated at the 18 hr time point, particularly in the case of FeS administration.
Figure 27:
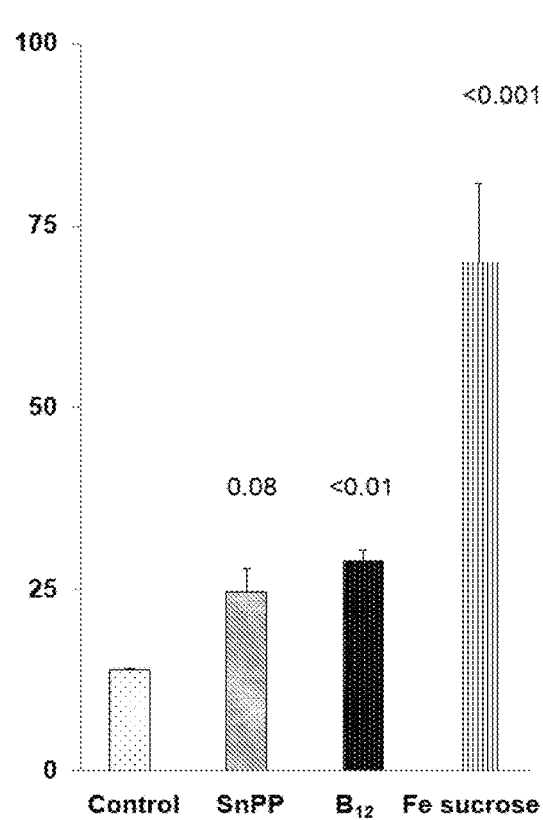

Renal cortical HO-1 mRNA and protein levels. As shown in FIG. 26, each of the agents induced marked and significant increases in HO-1 mRNA, as assessed 4 hr post injection. By 18 hrs, HO-1mRNA levels returned to normal values. As shown in FIG. 27, a correlate of the 4 hr mRNA increases was a significant increase in HO-1 protein levels. These levels remained elevated at the 18 hr time point, particularly in the case of FeS administration.

Prophetic Examples

Prophetic Example 1

Whether a depot formulation confers equal or greater cytoprotection with less potential toxicity than intravenous (IV) myoglobin/SnPP treatment and/or Fe—S and/or B12 will be assessed. Different doses of myoglobin with SnPP and/or Fe—S and/or B12 will be added as a suspension to 100 mg/ml PEG (PEG 5000). There are two rationales for conducting this experiment. First, by injecting either intramuscularly (IM) or subcutaneously (SQ) the myoglobin and SnPP and/or Fe—S and/or B12 will be absorbed relatively slowly (vs. instantaneous systemic myoglobin/SnPP and/or Fe—S and/or B12 exposure following IV injection). By slowing the myoglobin and/or Fe—S and/or B12 absorption with a depot PEG injection, a slower, more sustained renal exposure to myoglobin and/or Fe—S and/or B12 will result. This will favor increased myoglobin and/or Fe—S and/or B12 uptake, and at the same time, decrease the potential for nephrotoxicity, as can occur due to rapid renal myoglobin and/or Fe—S and/or B12 loading (which results in obstructive cast formation within tubular lumina). Second, PEG is an osmotic agent and will undergo renal excretion. Because an acute increase in urinary osmolality can induce cytoprotective proteins on its own, and also confer protection by causing increased urinary flow rates, an additive or synergistic beneficial effect may be observed.

Prophetic Example 2

Hematin will inhibit HO, and like SnPP, it can also induce an increase in HO production (via enzyme feedback inhibition). Thus, hematin should recapitulate the beneficial effects of SnPP treatment. Importantly, hematin has been approved by the FDA for the treatment of the clinical disease, *porphyria*. Thus, if hematin is as effective as SnPP, hematin may be selected for further study and clinical development.

Prophetic Example 3

It is well documented that HO protects against experimental sepsis and endotoxemia. HO-1 will be up-regulated according to the compositions, kits, and methods disclosed herein and then 18 hrs later, the mice will be challenged with endotoxin. At 2 and 24 hrs later, the severity of sepsis is gauged by inflammatory cytokine (TNF, MCP-1) levels in plasma and in kidney. Also, because endotoxemia causes kidney injury, the severity of kidney dysfunction by BUN and creatinine levels will be tested. The results will be compared to naïve mice subjected to Fendotoxin injection. When successful, this will greatly expand the utility of the disclosed protective strategies to patients at high risk of sepsis (e.g. ICU patients).

Prophetic Example 4

On-going studies will demonstrate the effectiveness of iron and/or vitamin B12 in protecting various organ systems from insult.

The compositions, kits, and methods disclosed herein are distinguished from "remote preconditioning" whereby one causes ischemia in the legs (e.g., by inflating blood pressure cuffs) to precondition other organs, which has met only very limited success. In particular embodiments, the compositions, kits and methods disclosed herein can be referred to as "remote pharmacologic preconditioning" (RPR).

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the ability of a disclosed composition, kit or method to protect an organ from a scheduled insult.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the", and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention can be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

What is claimed is:

1. A method of protecting an organ of a human patient from injury based on a scheduled insult comprising administering to the organ a therapeutically effective amount of (i) iron sucrose; and (ii) vitamin B12 or a derivative thereof, the therapeutically effective amount being administered before the insult to the organ occurs, wherein the administering protects the organ from injury without causing injury to the organ.

2. The method of claim 1, wherein the scheduled insult is surgery, chemotherapy, or radiocontrast toxicity.

3. The method of claim 2, wherein the surgery is an organ transplant surgery.

4. The method of claim 1, wherein the administration occurs at least 4 hours before the scheduled insult to the organ occurs.

5. The method of claim 1, wherein the administration occurs at least 12 hours before the scheduled insult to the organ occurs.

6. The method of claim 1, wherein the administration occurs at least 18 hours before the scheduled insult to the organ occurs.

7. The method of claim 1, wherein the organ is a transplanted organ.

8. The method of claim 1, wherein the organ is a heart, kidney, liver, or lung.

9. The method of claim 1, wherein the organ is a kidney and protection is evidenced by prevention or reduction in BUN or serum creatinine increases as compared to a reference level.

10. A method of protecting an organ of a human patient from injury based on a scheduled insult comprising administering to the organ a therapeutically effective amount of (i) iron sucrose; and (ii) vitamin B12 or a derivative thereof, the therapeutically effective amount being administered at least 2 hours before the scheduled insult to the organ occurs, wherein the administering protects the organ from injury without causing injury to the organ.

11. The method of claim 10, wherein the scheduled insult is surgery, chemotherapy, or radiocontrast toxicity.

12. The method of claim 11, wherein the surgery is an organ transplant surgery.

13. The method of claim 10, wherein the organ is a transplanted organ.

14. The method of claim 10, wherein the organ is a heart, kidney, liver, or lung.

15. The method of claim 10, wherein the organ is a kidney and protection is evidenced by prevention or reduction in BUN or serum creatinine increases as compared to a reference level.

16. The method of claim 1, wherein the derivative of vitamin B12 is an organometallic compound with a trivalent cobalt bound inside a corrin ring.

17. The method of claim 1, wherein the derivative of vitamin B12 is selected from methylcobalamin, 5-deoxyadenosyl cobalamin, cobalamin, or hydroxyl cobalamin.

18. The method of claim 1, wherein vitamin B12 is administered.

19. The method of claim 10, wherein the derivative of vitamin B12 is an organometallic compound with a trivalent cobalt bound inside a corrin ring.

20. The method of claim 10, wherein the derivative of vitamin B12 is selected from cyanocobalamin, methylcobalamin, 5-deoxyadenosyl cobalamin, cobalamin, or hydroxyl cobalamin.

21. The method of claim 10, wherein vitamin B12 is administered.

* * * * *

SEQUENCE LISTING

```
<160> NUMBER OF SEQ ID NOS: 29

<210> SEQ ID NO 1
<211> LENGTH: 288
<212> TYPE: PRT
<213> ORGANISM: Homo Sapiens

<400> SEQUENCE: 1

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30
```

```
Phe Met Arg Asn Phe Gln Lys Gly Gln Val Thr Arg Asp Gly Phe Lys
            35                  40                  45

Leu Val Met Ala Ser Leu Tyr His Ile Tyr Val Ala Leu Glu Glu
 50                  55                  60

Ile Glu Arg Asn Lys Glu Ser Pro Val Phe Ala Pro Val Tyr Phe Pro
 65                  70                  75                  80

Glu Glu Leu His Arg Lys Ala Ala Leu Glu Gln Asp Leu Ala Phe Trp
                 85                  90                  95

Tyr Gly Pro Arg Trp Gln Glu Val Ile Pro Tyr Thr Pro Ala Met Gln
             100                 105                 110

Arg Tyr Val Lys Arg Leu His Glu Val Gly Arg Thr Glu Pro Glu Leu
             115                 120                 125

Leu Val Ala His Ala Tyr Thr Arg Tyr Leu Gly Asp Leu Ser Gly Gly
 130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
             180                 185                 190

Pro Ala Val Arg Gln Arg Val Ile Glu Glu Ala Lys Thr Ala Phe Leu
             195                 200                 205

Leu Asn Ile Gln Leu Phe Glu Glu Leu Gln Glu Leu Leu Thr His Asp
 210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Arg Ser Gln Ala Pro Leu Leu Arg Trp Val Leu
             260                 265                 270

Thr Leu Ser Phe Leu Val Ala Thr Val Ala Val Gly Leu Tyr Ala Met
 275                 280                 285

<210> SEQ ID NO 2
<211> LENGTH: 370
<212> TYPE: PRT
<213> ORGANISM: Homo Sapiens

<400> SEQUENCE: 2

Met Glu Ser Arg Ser Val Ala Gln Ala Gly Val Gln Trp Ile Ser Leu
 1               5                  10                  15

Ala His Cys Ser Leu His Leu Leu Gly Ser Arg Asp Ser Pro Ala Ser
                 20                  25                  30

Ala Ser Cys Val Ala Gly Ile Thr Gly Pro Glu Glu Arg Glu Gln Gln
             35                  40                  45

Glu Pro His Pro Ala Ala Met Ser Ala Glu Val Glu Thr Ser Glu Gly
         50                  55                  60

Val Asp Glu Ser Glu Lys Lys Asn Ser Gly Ala Leu Glu Lys Glu Asn
 65                  70                  75                  80

Gln Met Arg Met Ala Asp Leu Ser Glu Leu Leu Lys Glu Gly Thr Lys
                 85                  90                  95

Glu Ala His Asp Arg Ala Glu Asn Thr Gln Phe Val Lys Asp Phe Leu
            100                 105                 110

Lys Gly Asn Ile Lys Lys Glu Leu Phe Lys Leu Ala Thr Thr Ala Leu
             115                 120                 125
```

-continued

Tyr Phe Thr Tyr Ser Ala Leu Glu Glu Glu Met Glu Arg Asn Lys Asp
        130                 135                 140

His Pro Ala Phe Ala Pro Leu Tyr Phe Pro Met Glu Leu His Arg Lys
145                 150                 155                 160

Glu Ala Leu Thr Lys Asp Met Glu Tyr Phe Phe Gly Glu Asn Trp Glu
                165                 170                 175

Glu Gln Val Gln Cys Pro Lys Ala Ala Gln Lys Tyr Val Glu Arg Ile
            180                 185                 190

His Tyr Ile Gly Gln Asn Glu Pro Glu Leu Leu Val Ala His Ala Tyr
        195                 200                 205

Thr Arg Tyr Met Gly Asp Leu Ser Gly Gly Gln Val Leu Lys Lys Val
    210                 215                 220

Ala Gln Arg Ala Leu Lys Leu Pro Ser Thr Gly Glu Gly Thr Gln Phe
225                 230                 235                 240

Tyr Leu Phe Glu Asn Val Asp Asn Ala Gln Gln Phe Lys Gln Leu Tyr
                245                 250                 255

Arg Ala Arg Met Asn Ala Leu Asp Leu Asn Met Lys Thr Lys Glu Arg
            260                 265                 270

Ile Val Glu Glu Ala Asn Lys Ala Phe Glu Tyr Asn Met Gln Ile Phe
        275                 280                 285

Asn Glu Leu Asp Gln Ala Gly Ser Thr Leu Ala Arg Glu Thr Leu Glu
    290                 295                 300

Asp Gly Phe Pro Val His Asp Gly Lys Gly Asp Met Arg Lys Cys Pro
305                 310                 315                 320

Phe Tyr Ala Ala Glu Gln Asp Lys Gly Ala Leu Glu Gly Ser Ser Cys
                325                 330                 335

Pro Phe Arg Thr Ala Met Ala Val Leu Arg Lys Pro Ser Leu Gln Phe
            340                 345                 350

Ile Leu Ala Ala Gly Val Ala Leu Ala Ala Gly Leu Leu Ala Trp Tyr
        355                 360                 365

Tyr Met
370

<210> SEQ ID NO 3
<211> LENGTH: 316
<212> TYPE: PRT
<213> ORGANISM: Homo Sapiens

<400> SEQUENCE: 3

Met Ser Ala Glu Val Glu Thr Ser Glu Gly Val Asp Glu Ser Glu Lys
1               5                   10                  15

Lys Asn Ser Gly Ala Leu Glu Lys Glu Asn Gln Met Arg Met Ala Asp
            20                  25                  30

Leu Ser Glu Leu Leu Lys Glu Gly Thr Lys Glu Ala His Asp Arg Ala
        35                  40                  45

Glu Asn Thr Gln Phe Val Lys Asp Phe Leu Lys Gly Asn Ile Lys Lys
    50                  55                  60

Glu Leu Phe Lys Leu Ala Thr Thr Ala Leu Tyr Phe Thr Tyr Ser Ala
65                  70                  75                  80

Leu Glu Glu Glu Met Glu Arg Asn Lys Asp His Pro Ala Phe Ala Pro
                85                  90                  95

Leu Tyr Phe Pro Met Glu Leu His Arg Lys Glu Ala Leu Thr Lys Asp
            100                 105                 110

Met Glu Tyr Phe Phe Gly Glu Asn Trp Glu Glu Gln Val Gln Cys Pro

```
            115                 120                 125
Lys Ala Ala Gln Lys Tyr Val Glu Arg Ile His Tyr Ile Gly Gln Asn
130                 135                 140

Glu Pro Glu Leu Leu Val Ala His Ala Tyr Thr Arg Tyr Met Gly Asp
145                 150                 155                 160

Leu Ser Gly Gly Gln Val Leu Lys Lys Val Ala Gln Arg Ala Leu Lys
                165                 170                 175

Leu Pro Ser Thr Gly Glu Gly Thr Gln Phe Tyr Leu Phe Glu Asn Val
            180                 185                 190

Asp Asn Ala Gln Gln Phe Lys Gln Leu Tyr Arg Ala Arg Met Asn Ala
            195                 200                 205

Leu Asp Leu Asn Met Lys Thr Lys Glu Arg Ile Val Glu Glu Ala Asn
210                 215                 220

Lys Ala Phe Glu Tyr Asn Met Gln Ile Phe Asn Glu Leu Asp Gln Ala
225                 230                 235                 240

Gly Ser Thr Leu Ala Arg Glu Thr Leu Glu Asp Gly Phe Pro Val His
                245                 250                 255

Asp Gly Lys Gly Asp Met Arg Lys Cys Pro Phe Tyr Ala Ala Glu Gln
            260                 265                 270

Asp Lys Gly Ala Leu Glu Gly Ser Cys Pro Phe Arg Thr Ala Met
            275                 280                 285

Ala Val Leu Arg Lys Pro Ser Leu Gln Phe Ile Leu Ala Ala Gly Val
290                 295                 300

Ala Leu Ala Ala Gly Leu Leu Ala Trp Tyr Tyr Met
305                 310                 315

<210> SEQ ID NO 4
<211> LENGTH: 287
<212> TYPE: PRT
<213> ORGANISM: Homo Sapiens

<400> SEQUENCE: 4

Met Ala Asp Leu Ser Glu Leu Leu Lys Glu Gly Thr Lys Glu Ala His
1               5                   10                  15

Asp Arg Ala Glu Asn Thr Gln Phe Val Lys Asp Phe Leu Lys Gly Asn
                20                  25                  30

Ile Lys Lys Glu Leu Phe Lys Leu Ala Thr Thr Ala Leu Tyr Phe Thr
            35                  40                  45

Tyr Ser Ala Leu Glu Glu Met Glu Arg Asn Lys Asp His Pro Ala
50                  55                  60

Phe Ala Pro Leu Tyr Phe Pro Met Glu Leu His Arg Lys Glu Ala Leu
65                  70                  75                  80

Thr Lys Asp Met Glu Tyr Phe Phe Gly Glu Asn Trp Glu Glu Gln Val
                85                  90                  95

Gln Cys Pro Lys Ala Ala Gln Lys Tyr Val Glu Arg Ile His Tyr Ile
            100                 105                 110

Gly Gln Asn Glu Pro Glu Leu Leu Val Ala His Ala Tyr Thr Arg Tyr
        115                 120                 125

Met Gly Asp Leu Ser Gly Gly Gln Val Leu Lys Lys Val Ala Gln Arg
130                 135                 140

Ala Leu Lys Leu Pro Ser Thr Gly Glu Gly Thr Gln Phe Tyr Leu Phe
145                 150                 155                 160

Glu Asn Val Asp Asn Ala Gln Gln Phe Lys Gln Leu Tyr Arg Ala Arg
                165                 170                 175
```

```
Met Asn Ala Leu Asp Leu Asn Met Lys Thr Lys Glu Arg Ile Val Glu
            180                 185                 190

Glu Ala Asn Lys Ala Phe Glu Tyr Asn Met Gln Ile Phe Asn Glu Leu
        195                 200                 205

Asp Gln Ala Gly Ser Thr Leu Ala Arg Glu Thr Leu Glu Asp Gly Phe
    210                 215                 220

Pro Val His Asp Gly Lys Gly Asp Met Arg Lys Cys Pro Phe Tyr Ala
225                 230                 235                 240

Ala Glu Gln Asp Lys Gly Ala Leu Glu Gly Ser Ser Cys Pro Phe Arg
                245                 250                 255

Thr Ala Met Ala Val Leu Arg Lys Pro Ser Leu Gln Phe Ile Leu Ala
            260                 265                 270

Ala Gly Val Ala Leu Ala Ala Gly Leu Leu Ala Trp Tyr Tyr Met
        275                 280                 285

<210> SEQ ID NO 5
<211> LENGTH: 290
<212> TYPE: PRT
<213> ORGANISM: Rattus norvegicus

<400> SEQUENCE: 5

Met Ser Ser Glu Val Glu Thr Ala Glu Ala Val Asp Glu Ser Glu Lys
1               5                   10                  15

Asn Ser Met Ala Ser Glu Lys Glu Asn His Ser Lys Ile Ala Asp Phe
            20                  25                  30

Ser Asp Leu Leu Lys Glu Gly Thr Lys Glu Ala Asp Asp Arg Ala Glu
        35                  40                  45

Asn Thr Gln Phe Val Lys Asp Phe Leu Lys Gly Asn Ile Lys Lys Glu
    50                  55                  60

Leu Phe Lys Leu Ala Thr Thr Ala Leu Ser Tyr Ser Ala Pro Glu Glu
65                  70                  75                  80

Glu Met Asp Ser Leu Thr Lys Asp Met Glu Tyr Phe Phe Gly Glu Asn
            85                  90                  95

Trp Glu Glu Lys Val Lys Cys Ser Glu Ala Ala Gln Thr Tyr Val Asp
        100                 105                 110

Gln Ile His Tyr Val Gly Gln Asn Glu Pro Glu His Leu Val Ala His
    115                 120                 125

Thr Tyr Ser Thr Tyr Met Gly Gly Asn Leu Ser Gly Asp Gln Val Leu
    130                 135                 140

Lys Lys Glu Thr Gln Pro Val Pro Phe Thr Arg Glu Gly Thr Gln Phe
145                 150                 155                 160

Tyr Leu Phe Glu His Val Asp Asn Ala Lys Gln Phe Lys Leu Phe Tyr
                165                 170                 175

Cys Ala Arg Leu Asn Ala Leu Asp Leu Asn Leu Lys Thr Lys Glu Arg
            180                 185                 190

Ile Val Glu Glu Ala Thr Lys Ala Phe Glu Tyr Asn Met Gln Ile Phe
        195                 200                 205

Ser Glu Leu Asp Gln Ala Gly Ser Ile Pro Val Arg Glu Thr Leu Lys
    210                 215                 220

Asn Gly Leu Ser Ile Leu Asp Gly Lys Gly Val Cys Lys Cys Pro
225                 230                 235                 240

Phe Asn Ala Ala Gln Pro Asp Lys Gly Thr Leu Gly Gly Ser Asn Cys
                245                 250                 255

Pro Phe Gln Met Ser Met Ala Leu Leu Arg Lys Pro Asn Leu Gln Leu
            260                 265                 270
```

```
Ile Leu Val Ala Ser Met Ala Leu Val Ala Gly Leu Leu Ala Trp Tyr
        275                 280                 285

Tyr Met
    290

<210> SEQ ID NO 6
<211> LENGTH: 406
<212> TYPE: PRT
<213> ORGANISM: Homo Sapiens

<400> SEQUENCE: 6

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
            20                  25                  30

Cys Pro Lys Pro Pro Glu Ile Ala His Gly Tyr Val Glu His Ser Val
        35                  40                  45

Arg Tyr Gln Cys Lys Asn Tyr Tyr Lys Leu Arg Thr Glu Gly Asp Gly
    50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
    130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
    210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
    290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
```

```
                340               345               350
Gly Asp Ala Gly Ser Ala Phe Ala Val His Asp Leu Glu Glu Asp Thr
            355                 360                 365

Trp Tyr Ala Thr Gly Ile Leu Ser Phe Asp Lys Ser Cys Ala Val Ala
    370                 375                 380

Glu Tyr Gly Val Tyr Val Lys Val Thr Ser Ile Gln Asp Trp Val Gln
385                 390                 395                 400

Lys Thr Ile Ala Glu Asn
                405

<210> SEQ ID NO 7
<211> LENGTH: 462
<212> TYPE: PRT
<213> ORGANISM: Homo Sapiens

<400> SEQUENCE: 7

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
                20                  25                  30

Gly Asn Val Ala Glu Gly Glu Thr Lys Pro Asp Pro Asp Val Thr Glu
            35                  40                  45

Arg Cys Ser Asp Gly Trp Ser Phe Asp Ala Thr Thr Leu Asp Asp Asn
    50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
        115                 120                 125

Pro Lys Leu Leu Gln Asp Glu Phe Pro Gly Ile Pro Ser Pro Leu Asp
    130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
            180                 185                 190

Arg Trp Leu Gly Arg Tyr Tyr Cys Phe Gln Gly Asn Gln Phe Leu Arg
        195                 200                 205

Phe Asp Pro Val Arg Gly Glu Val Pro Pro Arg Tyr Pro Arg Asp Val
    210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
                245                 250                 255

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
        275                 280                 285

Arg Asp Gly Trp His Ser Trp Pro Ile Ala His Gln Trp Pro Gln Gly
    290                 295                 300
```

```
Pro Ser Ala Val Asp Ala Phe Ser Trp Glu Lys Leu Tyr Leu
305                 310                 315                 320

Val Gln Gly Thr Gln Val Tyr Val Phe Leu Thr Lys Gly Gly Tyr Thr
                325                 330                 335

Leu Val Ser Gly Tyr Pro Lys Arg Leu Glu Lys Glu Val Gly Thr Pro
                340                 345                 350

His Gly Ile Ile Leu Asp Ser Val Asp Ala Ala Phe Ile Cys Pro Gly
                355                 360                 365

Ser Ser Arg Leu His Ile Met Ala Gly Arg Arg Leu Trp Trp Leu Asp
            370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
                405                 410                 415

Ser Cys Ser Ala Asn Gly Pro Gly Leu Tyr Leu Ile His Gly Pro Asn
                420                 425                 430

Leu Tyr Cys Tyr Ser Asp Val Glu Lys Leu Asn Ala Ala Lys Ala Leu
                435                 440                 445

Pro Gln Pro Gln Asn Val Thr Ser Leu Leu Gly Cys Thr His
450                 455                 460

<210> SEQ ID NO 8
<211> LENGTH: 84
<212> TYPE: PRT
<213> ORGANISM: Homo Sapiens

<400> SEQUENCE: 8

Met Ala Leu Ser Ser Gln Ile Trp Ala Ala Cys Leu Leu Leu Leu
1               5                   10                  15

Leu Leu Ala Ser Leu Thr Ser Gly Ser Val Phe Pro Gln Gln Thr Gly
                20                  25                  30

Gln Leu Ala Glu Leu Gln Pro Gln Asp Arg Ala Gly Ala Arg Ala Ser
            35                  40                  45

Trp Met Pro Met Phe Gln Arg Arg Arg Arg Arg Asp Thr His Phe Pro
50                  55                  60

Ile Cys Ile Phe Cys Cys Gly Cys Cys His Arg Ser Lys Cys Gly Met
65                  70                  75                  80

Cys Cys Lys Thr

<210> SEQ ID NO 9
<211> LENGTH: 25
<212> TYPE: PRT
<213> ORGANISM: Homo Sapiens

<400> SEQUENCE: 9

Asp Thr His Phe Pro Ile Cys Ile Phe Cys Cys Gly Cys Cys His Arg
1               5                   10                  15

Ser Lys Cys Gly Met Cys Cys Lys Thr
                20                  25

<210> SEQ ID NO 10
<211> LENGTH: 418
<212> TYPE: PRT
<213> ORGANISM: Homo Sapiens

<400> SEQUENCE: 10

Met Pro Ser Ser Val Ser Trp Gly Ile Leu Leu Leu Ala Gly Leu Cys
1               5                   10                  15
```

```
Cys Leu Val Pro Val Ser Leu Ala Glu Asp Pro Gln Gly Asp Ala Ala
             20                  25                  30

Gln Lys Thr Asp Thr Ser His His Asp Gln Asp His Pro Thr Phe Asn
         35                  40                  45

Lys Ile Thr Pro Asn Leu Ala Glu Phe Ala Phe Ser Leu Tyr Arg Gln
 50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
             100                 105                 110

Glu Ala Gln Ile His Glu Gly Phe Gln Glu Leu Leu Arg Thr Leu Asn
             115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                 165                 170                 175

Ala Lys Lys Gln Ile Asn Asp Tyr Val Glu Lys Gly Thr Gln Gly Lys
             180                 185                 190

Ile Val Asp Leu Val Lys Glu Leu Asp Arg Asp Thr Val Phe Ala Leu
             195                 200                 205

Val Asn Tyr Ile Phe Phe Lys Gly Lys Trp Glu Arg Pro Phe Glu Val
             210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                 245                 250                 255

Lys Lys Leu Ser Ser Trp Val Leu Leu Met Lys Tyr Leu Gly Asn Ala
             260                 265                 270

Thr Ala Ile Phe Phe Leu Pro Asp Glu Gly Lys Leu Gln His Leu Glu
             275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                 325                 330                 335

Ser Asn Gly Ala Asp Leu Ser Gly Val Thr Glu Glu Ala Pro Leu Lys
             340                 345                 350

Leu Ser Lys Ala Val His Lys Ala Val Leu Thr Ile Asp Glu Lys Gly
             355                 360                 365

Thr Glu Ala Ala Gly Ala Met Phe Leu Glu Ala Ile Pro Met Ser Ile
             370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                 405                 410                 415

Gln Lys
```

-continued

```
<210> SEQ ID NO 11
<211> LENGTH: 178
<212> TYPE: PRT
<213> ORGANISM: Homo Sapiens

<400> SEQUENCE: 11

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 12
<211> LENGTH: 654
<212> TYPE: PRT
<213> ORGANISM: Homo Sapiens

<400> SEQUENCE: 12

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
            20                  25                  30

Ile Asp Leu Gly Thr Thr Tyr Ser Cys Val Gly Val Phe Lys Asn Gly
        35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160
```

```
Leu Gly Lys Lys Val Thr His Ala Val Val Thr Val Pro Ala Tyr Phe
            165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
            195                 200                 205

Tyr Gly Leu Asp Lys Arg Glu Gly Glu Lys Asn Ile Leu Val Phe Asp
            210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
            245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
            290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
            325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
            370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
            405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
            435                 440                 445

Gln Ile Phe Ser Thr Ala Ser Asp Asn Gln Pro Thr Val Thr Ile Lys
            450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
            485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
            530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
            565                 570                 575
```

-continued

```
Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 13
<211> LENGTH: 840
<212> TYPE: PRT
<213> ORGANISM: Homo Sapiens

<400> SEQUENCE: 13

Met Ser Val Val Gly Ile Asp Leu Gly Phe Gln Ser Cys Tyr Val Ala
1               5                   10                  15

Val Ala Arg Ala Gly Gly Ile Glu Thr Ile Ala Asn Glu Tyr Ser Asp
            20                  25                  30

Arg Cys Thr Pro Ala Cys Ile Ser Phe Gly Pro Lys Asn Arg Ser Ile
        35                  40                  45

Gly Ala Ala Ala Lys Ser Gln Val Ile Ser Asn Ala Lys Asn Thr Val
    50                  55                  60

Gln Gly Phe Lys Arg Phe His Gly Arg Ala Phe Ser Asp Pro Phe Val
65                  70                  75                  80

Glu Ala Glu Lys Ser Asn Leu Ala Tyr Asp Ile Val Gln Leu Pro Thr
                85                  90                  95

Gly Leu Thr Gly Ile Lys Val Thr Tyr Met Glu Glu Glu Arg Asn Phe
            100                 105                 110

Thr Thr Glu Gln Val Thr Ala Met Leu Leu Ser Lys Leu Lys Glu Thr
        115                 120                 125

Ala Glu Ser Val Leu Lys Lys Pro Val Val Asp Cys Val Val Ser Val
    130                 135                 140

Pro Cys Phe Tyr Thr Asp Ala Glu Arg Arg Ser Val Met Asp Ala Thr
145                 150                 155                 160

Gln Ile Ala Gly Leu Asn Cys Leu Arg Leu Met Asn Glu Thr Thr Ala
                165                 170                 175

Val Ala Leu Ala Tyr Gly Ile Tyr Lys Gln Asp Leu Pro Ala Leu Glu
            180                 185                 190

Glu Lys Pro Arg Asn Val Val Phe Val Asp Met Gly His Ser Ala Tyr
        195                 200                 205

Gln Val Ser Val Cys Ala Phe Asn Arg Gly Lys Leu Lys Val Leu Ala
    210                 215                 220

Thr Ala Phe Asp Thr Thr Leu Gly Gly Arg Lys Phe Asp Glu Val Leu
225                 230                 235                 240

Val Asn His Phe Cys Glu Glu Phe Gly Lys Lys Tyr Lys Leu Asp Ile
                245                 250                 255

Lys Ser Lys Ile Arg Ala Leu Leu Arg Leu Ser Gln Glu Cys Glu Lys
            260                 265                 270

Leu Lys Lys Leu Met Ser Ala Asn Ala Ser Asp Leu Pro Leu Ser Ile
        275                 280                 285

Glu Cys Phe Met Asn Asp Val Asp Val Ser Gly Thr Met Asn Arg Gly
    290                 295                 300
```

```
Lys Phe Leu Glu Met Cys Asn Asp Leu Leu Ala Arg Val Glu Pro Pro
305                 310                 315                 320

Leu Arg Ser Val Leu Glu Gln Thr Lys Leu Lys Lys Glu Asp Ile Tyr
            325                 330                 335

Ala Val Glu Ile Val Gly Gly Ala Thr Arg Ile Pro Ala Val Lys Glu
            340                 345                 350

Lys Ile Ser Lys Phe Phe Gly Lys Glu Leu Ser Thr Thr Leu Asn Ala
            355                 360                 365

Asp Glu Ala Val Thr Arg Gly Cys Ala Leu Gln Cys Ala Ile Leu Ser
            370                 375                 380

Pro Ala Phe Lys Val Arg Glu Phe Ser Ile Thr Asp Val Val Pro Tyr
385                 390                 395                 400

Pro Ile Ser Leu Arg Trp Asn Ser Pro Ala Glu Glu Gly Ser Ser Asp
            405                 410                 415

Cys Glu Val Phe Ser Lys Asn His Ala Ala Pro Phe Ser Lys Val Leu
            420                 425                 430

Thr Phe Tyr Arg Lys Glu Pro Phe Thr Leu Glu Ala Tyr Tyr Ser Ser
            435                 440                 445

Pro Gln Asp Leu Pro Tyr Pro Asp Pro Ala Ile Ala Gln Phe Ser Val
            450                 455                 460

Gln Lys Val Thr Pro Gln Ser Asp Gly Ser Ser Ser Lys Val Lys Val
465                 470                 475                 480

Lys Val Arg Val Asn Val His Gly Ile Phe Ser Val Ser Ser Ala Ser
            485                 490                 495

Leu Val Glu Val His Lys Ser Glu Glu Asn Glu Glu Pro Met Glu Thr
            500                 505                 510

Asp Gln Asn Ala Lys Glu Glu Lys Met Gln Val Asp Gln Glu Glu
            515                 520                 525

Pro His Val Glu Glu Gln Gln Gln Thr Pro Ala Glu Asn Lys Ala
            530                 535                 540

Glu Ser Glu Glu Met Glu Thr Ser Gln Ala Gly Ser Lys Asp Lys Lys
545                 550                 555                 560

Met Asp Gln Pro Pro Gln Ala Lys Lys Ala Lys Val Lys Thr Ser Thr
            565                 570                 575

Val Asp Leu Pro Ile Glu Asn Gln Leu Leu Trp Gln Ile Asp Arg Glu
            580                 585                 590

Met Leu Asn Leu Tyr Ile Glu Asn Glu Gly Lys Met Ile Met Gln Asp
            595                 600                 605

Lys Leu Glu Lys Glu Arg Asn Asp Ala Lys Asn Ala Val Glu Glu Tyr
            610                 615                 620

Val Tyr Glu Met Arg Asp Lys Leu Ser Gly Glu Tyr Glu Lys Phe Val
625                 630                 635                 640

Ser Glu Asp Asp Arg Asn Ser Phe Thr Leu Lys Leu Glu Asp Thr Glu
            645                 650                 655

Asn Trp Leu Tyr Glu Asp Gly Glu Asp Gln Pro Lys Gln Val Tyr Val
            660                 665                 670

Asp Lys Leu Ala Glu Leu Lys Asn Leu Gly Gln Pro Ile Lys Ile Arg
            675                 680                 685

Phe Gln Glu Ser Glu Glu Arg Pro Lys Leu Phe Glu Glu Leu Gly Lys
            690                 695                 700

Gln Ile Gln Gln Tyr Met Lys Ile Ile Ser Ser Phe Lys Asn Lys Glu
705                 710                 715                 720
```

-continued

```
Asp Gln Tyr Asp His Leu Asp Ala Ala Asp Met Thr Lys Val Glu Lys
                725                 730                 735

Ser Thr Asn Glu Ala Met Glu Trp Met Asn Asn Lys Leu Asn Leu Gln
            740                 745                 750

Asn Lys Gln Ser Leu Thr Met Asp Pro Val Val Lys Ser Lys Glu Ile
        755                 760                 765

Glu Ala Lys Ile Lys Glu Leu Thr Ser Thr Cys Ser Pro Ile Ile Ser
    770                 775                 780

Lys Pro Lys Pro Lys Val Glu Pro Pro Lys Glu Gln Lys Asn Ala
785                 790                 795                 800

Glu Gln Asn Gly Pro Val Asp Gly Gln Gly Asp Asn Pro Gly Pro Gln
            805                 810                 815

Ala Ala Glu Gln Gly Thr Asp Thr Ala Val Pro Ser Asp Ser Asp Lys
        820                 825                 830

Lys Leu Pro Glu Met Asp Ile Asp
    835                 840

<210> SEQ ID NO 14
<211> LENGTH: 803
<212> TYPE: PRT
<213> ORGANISM: Homo Sapiens

<400> SEQUENCE: 14

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255
```

```
Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670
```

Ile Ser Thr Asn Tyr Tyr Ala Ser Gln Lys Lys Thr Phe Glu Ile Asn
            675                 680                 685

Pro Arg His Pro Leu Ile Arg Asp Met Leu Arg Ile Lys Glu Asp
    690                 695                 700

Glu Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
                755                 760                 765

Asp Thr Thr Glu Asp Thr Glu Gln Asp Glu Asp Glu Glu Met Asp Val
        770                 775                 780

Gly Thr Asp Glu Glu Glu Thr Ala Lys Glu Ser Thr Ala Glu Lys
785                 790                 795                 800

Asp Glu Leu

<210> SEQ ID NO 15
<211> LENGTH: 573
<212> TYPE: PRT
<213> ORGANISM: Homo Sapiens

<400> SEQUENCE: 15

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

```
Asp Ala Tyr Val Leu Leu Ser Glu Lys Lys Ile Ser Ser Ile Gln Ser
            245                 250                 255

Ile Val Pro Ala Leu Glu Ile Ala Asn Ala His Arg Lys Pro Leu Val
        260                 265                 270

Ile Ile Ala Glu Asp Val Asp Gly Glu Ala Leu Ser Thr Leu Val Leu
    275                 280                 285

Asn Arg Leu Lys Val Gly Leu Gln Val Ala Val Lys Ala Pro Gly
290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Val
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570

<210> SEQ ID NO 16
<211> LENGTH: 340
<212> TYPE: PRT
<213> ORGANISM: Homo Sapiens

<400> SEQUENCE: 16

Met Gly Lys Asp Tyr Tyr Gln Thr Leu Gly Leu Ala Arg Gly Ala Ser
1               5                   10                  15

Asp Glu Glu Ile Lys Arg Ala Tyr Arg Arg Gln Ala Leu Arg Tyr His
            20                  25                  30

Pro Asp Lys Asn Lys Glu Pro Gly Ala Glu Glu Lys Phe Lys Glu Ile
        35                  40                  45
```

```
Ala Glu Ala Tyr Asp Val Leu Ser Asp Pro Arg Lys Arg Glu Ile Phe
        50                  55                  60

Asp Arg Tyr Gly Glu Glu Gly Leu Lys Gly Ser Gly Pro Ser Gly Gly
 65                  70                  75                  80

Ser Gly Gly Ala Asn Gly Thr Ser Phe Ser Tyr Thr Phe His Gly
                85                  90                  95

Asp Pro His Ala Met Phe Ala Glu Phe Phe Gly Gly Arg Asn Pro Phe
                100                 105                 110

Asp Thr Phe Phe Gly Gln Arg Asn Gly Glu Glu Gly Met Asp Ile Asp
                115                 120                 125

Asp Pro Phe Ser Gly Phe Pro Met Gly Met Gly Gly Phe Thr Asn Val
                130                 135                 140

Asn Phe Gly Arg Ser Arg Ser Ala Gln Glu Pro Ala Arg Lys Lys Gln
145                 150                 155                 160

Asp Pro Pro Val Thr His Asp Leu Arg Val Ser Leu Glu Glu Ile Tyr
                165                 170                 175

Ser Gly Cys Thr Lys Lys Met Lys Ile Ser His Lys Arg Leu Asn Pro
                180                 185                 190

Asp Gly Lys Ser Ile Arg Asn Glu Asp Lys Ile Leu Thr Ile Glu Val
                195                 200                 205

Lys Lys Gly Trp Lys Glu Gly Thr Lys Ile Thr Phe Pro Lys Glu Gly
                210                 215                 220

Asp Gln Thr Ser Asn Asn Ile Pro Ala Asp Ile Val Phe Val Leu Lys
225                 230                 235                 240

Asp Lys Pro His Asn Ile Phe Lys Arg Asp Gly Ser Asp Val Ile Tyr
                245                 250                 255

Pro Ala Arg Ile Ser Leu Arg Glu Ala Leu Cys Gly Cys Thr Val Asn
                260                 265                 270

Val Pro Thr Leu Asp Gly Arg Thr Ile Pro Val Val Phe Lys Asp Val
                275                 280                 285

Ile Arg Pro Gly Met Arg Arg Lys Val Pro Gly Glu Gly Leu Pro Leu
                290                 295                 300

Pro Lys Thr Pro Glu Lys Arg Gly Asp Leu Ile Ile Glu Phe Glu Val
305                 310                 315                 320

Ile Phe Pro Glu Arg Ile Pro Gln Thr Ser Arg Thr Val Leu Glu Gln
                325                 330                 335

Val Leu Pro Ile
                340

<210> SEQ ID NO 17
<211> LENGTH: 645
<212> TYPE: PRT
<213> ORGANISM: Homo Sapiens

<400> SEQUENCE: 17

Met Ser Lys Ala Val Gly Ile Asp Leu Gly Thr Thr Tyr Ser Cys Val
 1                   5                  10                  15

Ala His Phe Val Asn Asp Arg Val Glu Ile Ile Ala Asn Asp Gln Gly
                20                  25                  30

Asn Arg Thr Thr Pro Ser Phe Val Ala Phe Thr Asp Thr Glu Arg Leu
                35                  40                  45

Ile Gly Asp Ala Ala Lys Asn Gln Ala Ala Met Asn Pro Ala Asn Thr
        50                  55                  60

Val Phe Asp Ala Lys Arg Leu Ile Gly Arg Lys Phe Asp Asp Pro Glu
```

```
                65                  70                  75                  80
        Val Gln Asn Asp Ile Lys His Phe Pro Phe Lys Val Val Glu Lys Gly
                        85                  90                  95
        Gly Lys Pro His Ile Gln Val Glu Phe Lys Gly Glu Thr Lys Val Phe
                        100                 105                 110
        Thr Pro Glu Glu Ile Ser Ser Met Val Leu Thr Lys Met Lys Glu Thr
                        115                 120                 125
        Ala Glu Ser Tyr Met Gly Gly Lys Val Thr Asp Ala Val Ile Thr Val
                        130                 135                 140
        Pro Ala Tyr Phe Asn Asp Ser Gln Arg Gln Ala Thr Lys Asp Ala Gly
        145                 150                 155                 160
        Leu Ile Ala Gly Leu Asn Val Leu Arg Ile Ile Asn Glu Pro Thr Ala
                        165                 170                 175
        Ala Ala Ile Ala Tyr Gly Leu Asp Lys Lys Glu Gln Gly Lys Gly Glu
                        180                 185                 190
        Gln Asn Ile Leu Ile Phe Asp Leu Gly Gly Gly Thr Phe Asp Val Ser
                        195                 200                 205
        Leu Leu Ser Ile Asp Glu Gly Ile Phe Glu Val Lys Ala Thr Ala Gly
        210                 215                 220
        Asp Thr His Leu Gly Gly Glu Asp Phe Asp Asn Arg Leu Val Asn His
        225                 230                 235                 240
        Phe Ala Asn Glu Phe Lys Arg Lys Tyr Lys Lys Asp Leu Thr Thr Asn
                        245                 250                 255
        Gln Arg Ala Leu Arg Arg Leu Arg Thr Ala Cys Glu Arg Ala Lys Arg
                        260                 265                 270
        Thr Leu Ser Ser Ser Ala Gln Thr Ser Val Glu Ile Asp Ser Leu Tyr
                        275                 280                 285
        Glu Gly Ile Asp Phe Tyr Thr Ser Ile Thr Arg Ala Arg Phe Glu Glu
                        290                 295                 300
        Leu Cys Gln Asp Leu Phe Arg Ser Thr Leu Asp Pro Val Glu Lys Val
        305                 310                 315                 320
        Met Arg Asp Gly Lys Leu Asp Lys Ser Gln Val Ala Glu Ile Val Leu
                        325                 330                 335
        Val Gly Gly Ser Thr Arg Ile Pro Lys Ile Gln Lys Leu Val Ser Asp
                        340                 345                 350
        Phe Phe Asn Gly Lys Glu Pro Asn Lys Ser Ile Asn Pro Asp Glu Ala
                        355                 360                 365
        Val Ala Tyr Gly Ala Ala Val Gln Ala Ala Ile Leu Thr Gly Asp Thr
                        370                 375                 380
        Ser Ser Lys Thr Gln Asp Leu Leu Leu Leu Asp Val Ala Pro Leu Ser
        385                 390                 395                 400
        Leu Gly Ile Glu Thr Ala Gly Gly Val Met Thr Lys Leu Ile Pro Arg
                        405                 410                 415
        Asn Thr Thr Ile Pro Thr Lys Lys Ser Glu Ile Phe Ser Thr Tyr Ser
                        420                 425                 430
        Asp Asn Gln Pro Gly Val Leu Ile Gln Val Tyr Glu Gly Glu Arg Ala
                        435                 440                 445
        Lys Thr Lys Asp Asn Asn Leu Leu Gly Lys Phe Glu Leu Ser Gly Ile
                        450                 455                 460
        Pro Pro Ala Pro Arg Gly Val Pro Gln Ile Glu Val Thr Phe Asp Ile
        465                 470                 475                 480
        Asp Ala Asn Gly Ile Leu Asn Val Ser Ala Val Glu Lys Gly Thr Gly
                        485                 490                 495
```

-continued

```
Lys Ser Gln Lys Ile Thr Ile Thr Asn Asp Lys Gly Arg Leu Ser Lys
                500                 505                 510

Glu Glu Ile Asp Arg Met Val Ala Glu Ala Lys Tyr Lys Glu Glu
            515                 520                 525

Asp Glu Lys Glu Ala Ala Arg Ile Ala Ala Lys Asn Gly Leu Glu Ser
        530                 535                 540

Tyr Ala Tyr Ser Leu Lys Gln Thr Ala Ser Glu Lys Gln Phe Glu Glu
545                 550                 555                 560

Lys Val Asp Ala Ser Lys Arg Glu Ser Leu Asn Lys Ala Ile Glu Glu
                565                 570                 575

Thr Ile Ser Trp Leu Asp Asn Asn Gln Ser Ala Thr Thr Asp Glu Tyr
            580                 585                 590

Glu Asp Lys Arg Lys Glu Leu Glu Gly Ile Ala Asn Asp Ala Leu Lys
        595                 600                 605

Asp Leu Tyr Ala Ala Gly Gly Val Pro Gly Gly Ala Ala Pro Gly Gly
    610                 615                 620

Phe Pro Gly Ala Gly Gly Ala Ala Pro Gly Ala Asp Gln Gly Pro Ser
625                 630                 635                 640

Val Glu Glu Val Asp
                645

<210> SEQ ID NO 18
<211> LENGTH: 854
<212> TYPE: PRT
<213> ORGANISM: Homo Sapiens

<400> SEQUENCE: 18

Met Pro Pro Cys Ser Gly Gly Asp Gly Ser Thr Pro Gly Pro Ser
1               5                   10                  15

Leu Arg Asp Arg Asp Cys Pro Ala Gln Ser Ala Glu Tyr Pro Arg Asp
                20                  25                  30

Arg Leu Asp Pro Arg Pro Gly Ser Pro Ser Glu Ala Ser Ser Pro Pro
            35                  40                  45

Phe Leu Arg Ser Arg Ala Pro Val Asn Trp Tyr Gln Glu Lys Ala Gln
        50                  55                  60

Val Phe Leu Trp His Leu Met Val Ser Gly Ser Thr Thr Leu Leu Cys
65                  70                  75                  80

Leu Trp Lys Gln Pro Phe His Val Ser Ala Phe Pro Val Thr Ala Ser
                85                  90                  95

Leu Ala Phe Arg Gln Ser Gln Gly Ala Gly Gln His Leu Tyr Lys Asp
            100                 105                 110

Leu Gln Pro Phe Ile Leu Leu Arg Leu Leu Met Pro Glu Glu Thr Gln
        115                 120                 125

Thr Gln Asp Gln Pro Met Glu Glu Glu Glu Val Glu Thr Phe Ala Phe
    130                 135                 140

Gln Ala Glu Ile Ala Gln Leu Met Ser Leu Ile Ile Asn Thr Phe Tyr
145                 150                 155                 160

Ser Asn Lys Glu Ile Phe Leu Arg Glu Leu Ile Ser Asn Ser Ser Asp
                165                 170                 175

Ala Leu Asp Lys Ile Arg Tyr Glu Ser Leu Thr Asp Pro Ser Lys Leu
            180                 185                 190

Asp Ser Gly Lys Glu Leu His Ile Asn Leu Ile Pro Asn Lys Gln Asp
        195                 200                 205

Arg Thr Leu Thr Ile Val Asp Thr Gly Ile Gly Met Thr Lys Ala Asp
```

```
              210                 215                 220
Leu Ile Asn Asn Leu Gly Thr Ile Ala Lys Ser Gly Thr Lys Ala Phe
225                 230                 235                 240

Met Glu Ala Leu Gln Ala Gly Ala Asp Ile Ser Met Ile Gly Gln Phe
                245                 250                 255

Gly Val Gly Phe Tyr Ser Ala Tyr Leu Val Ala Glu Lys Val Thr Val
                260                 265                 270

Ile Thr Lys His Asn Asp Asp Glu Gln Tyr Ala Trp Glu Ser Ser Ala
                275                 280                 285

Gly Gly Ser Phe Thr Val Arg Thr Asp Thr Gly Glu Pro Met Gly Arg
                290                 295                 300

Gly Thr Lys Val Ile Leu His Leu Lys Glu Asp Gln Thr Glu Tyr Leu
305                 310                 315                 320

Glu Glu Arg Arg Ile Lys Glu Ile Val Lys Lys His Ser Gln Phe Ile
                325                 330                 335

Gly Tyr Pro Ile Thr Leu Phe Val Glu Lys Glu Arg Asp Lys Glu Val
                340                 345                 350

Ser Asp Asp Glu Ala Glu Glu Lys Glu Asp Lys Glu Glu Glu Lys Glu
                355                 360                 365

Lys Glu Glu Lys Glu Ser Glu Asp Lys Pro Glu Ile Glu Asp Val Gly
370                 375                 380

Ser Asp Glu Glu Glu Lys Lys Asp Gly Asp Lys Lys Lys Lys
385                 390                 395                 400

Lys Ile Lys Glu Lys Tyr Ile Asp Gln Glu Glu Leu Asn Lys Thr Lys
                405                 410                 415

Pro Ile Trp Thr Arg Asn Pro Asp Asp Ile Thr Asn Glu Glu Tyr Gly
                420                 425                 430

Glu Phe Tyr Lys Ser Leu Thr Asn Asp Trp Glu Asp His Leu Ala Val
                435                 440                 445

Lys His Phe Ser Val Glu Gly Gln Leu Glu Phe Arg Ala Leu Leu Phe
450                 455                 460

Val Pro Arg Arg Ala Pro Phe Asp Leu Phe Glu Asn Arg Lys Lys Lys
465                 470                 475                 480

Asn Asn Ile Lys Leu Tyr Val Arg Arg Val Phe Ile Met Asp Asn Cys
                485                 490                 495

Glu Glu Leu Ile Pro Glu Tyr Leu Asn Phe Ile Arg Gly Val Val Asp
                500                 505                 510

Ser Glu Asp Leu Pro Leu Asn Ile Ser Arg Glu Met Leu Gln Gln Ser
                515                 520                 525

Lys Ile Leu Lys Val Ile Arg Lys Asn Leu Val Lys Lys Cys Leu Glu
                530                 535                 540

Leu Phe Thr Glu Leu Ala Glu Asp Lys Glu Asn Tyr Lys Lys Phe Tyr
545                 550                 555                 560

Glu Gln Phe Ser Lys Asn Ile Lys Leu Gly Ile His Glu Asp Ser Gln
                565                 570                 575

Asn Arg Lys Lys Leu Ser Glu Leu Leu Arg Tyr Tyr Thr Ser Ala Ser
                580                 585                 590

Gly Asp Glu Met Val Ser Leu Lys Asp Tyr Cys Thr Arg Met Lys Glu
                595                 600                 605

Asn Gln Lys His Ile Tyr Tyr Ile Thr Gly Glu Thr Lys Asp Gln Val
                610                 615                 620

Ala Asn Ser Ala Phe Val Glu Arg Leu Arg Lys His Gly Leu Glu Val
625                 630                 635                 640
```

-continued

```
Ile Tyr Met Ile Glu Pro Ile Asp Glu Tyr Cys Val Gln Gln Leu Lys
                645                 650                 655
Glu Phe Glu Gly Lys Thr Leu Val Ser Val Thr Lys Glu Gly Leu Glu
            660                 665                 670
Leu Pro Glu Asp Glu Glu Lys Lys Gln Glu Glu Lys Lys Thr
        675                 680                 685
Lys Phe Glu Asn Leu Cys Lys Ile Met Lys Asp Ile Leu Glu Lys Lys
    690                 695                 700
Val Glu Lys Val Val Ser Asn Arg Leu Val Thr Ser Pro Cys Cys
705                 710                 715                 720
Ile Val Thr Ser Thr Tyr Gly Trp Thr Ala Asn Met Glu Arg Ile Met
                725                 730                 735
Lys Ala Gln Ala Leu Arg Asp Asn Ser Thr Met Gly Tyr Met Ala Ala
            740                 745                 750
Lys Lys His Leu Glu Ile Asn Pro Asp His Ser Ile Ile Glu Thr Leu
        755                 760                 765
Arg Gln Lys Ala Glu Ala Asp Lys Asn Asp Lys Ser Val Lys Asp Leu
    770                 775                 780
Val Ile Leu Leu Tyr Glu Thr Ala Leu Leu Ser Ser Gly Phe Ser Leu
785                 790                 795                 800
Glu Asp Pro Gln Thr His Ala Asn Arg Ile Tyr Arg Met Ile Lys Leu
                805                 810                 815
Gly Leu Gly Ile Asp Glu Asp Pro Thr Ala Asp Asp Thr Ser Ala
            820                 825                 830
Ala Val Thr Glu Glu Met Pro Pro Leu Glu Gly Asp Asp Thr Ser
        835                 840                 845
Arg Met Glu Glu Val Asp
    850

<210> SEQ ID NO 19
<211> LENGTH: 732
<212> TYPE: PRT
<213> ORGANISM: Homo Sapiens

<400> SEQUENCE: 19

Met Pro Glu Glu Thr Gln Thr Gln Asp Gln Pro Met Glu Glu Glu Glu
1               5                   10                  15
Val Glu Thr Phe Ala Phe Gln Ala Glu Ile Ala Gln Leu Met Ser Leu
                20                  25                  30
Ile Ile Asn Thr Phe Tyr Ser Asn Lys Glu Ile Phe Leu Arg Glu Leu
            35                  40                  45
Ile Ser Asn Ser Ser Asp Ala Leu Asp Lys Ile Arg Tyr Glu Ser Leu
        50                  55                  60
Thr Asp Pro Ser Lys Leu Asp Ser Gly Lys Glu Leu His Ile Asn Leu
65                  70                  75                  80
Ile Pro Asn Lys Gln Asp Arg Thr Leu Thr Ile Val Asp Thr Gly Ile
                85                  90                  95
Gly Met Thr Lys Ala Asp Leu Ile Asn Asn Leu Gly Thr Ile Ala Lys
            100                 105                 110
Ser Gly Thr Lys Ala Phe Met Glu Ala Leu Gln Ala Gly Ala Asp Ile
        115                 120                 125
Ser Met Ile Gly Gln Phe Gly Val Gly Phe Tyr Ser Ala Tyr Leu Val
    130                 135                 140
Ala Glu Lys Val Thr Val Ile Thr Lys His Asn Asp Asp Glu Gln Tyr
```

```
            145                 150                 155                 160
Ala Trp Glu Ser Ser Ala Gly Gly Ser Phe Thr Val Arg Thr Asp Thr
                    165                 170                 175
Gly Glu Pro Met Gly Arg Gly Thr Lys Val Ile Leu His Leu Lys Glu
                180                 185                 190
Asp Gln Thr Glu Tyr Leu Glu Arg Arg Ile Lys Glu Ile Val Lys
            195                 200                 205
Lys His Ser Gln Phe Ile Gly Tyr Pro Ile Thr Leu Phe Val Glu Lys
210                 215                 220
Glu Arg Asp Lys Glu Val Ser Asp Asp Glu Ala Glu Glu Lys Glu Asp
225                 230                 235                 240
Lys Glu Glu Glu Lys Glu Lys Glu Glu Lys Glu Ser Glu Asp Lys Pro
                    245                 250                 255
Glu Ile Glu Asp Val Gly Ser Asp Glu Glu Glu Glu Lys Lys Asp Gly
                260                 265                 270
Asp Lys Lys Lys Lys Lys Lys Ile Lys Glu Lys Tyr Ile Asp Gln Glu
            275                 280                 285
Glu Leu Asn Lys Thr Lys Pro Ile Trp Thr Arg Asn Pro Asp Asp Ile
        290                 295                 300
Thr Asn Glu Glu Tyr Gly Glu Phe Tyr Lys Ser Leu Thr Asn Asp Trp
305                 310                 315                 320
Glu Asp His Leu Ala Val Lys His Phe Ser Val Glu Gly Gln Leu Glu
                    325                 330                 335
Phe Arg Ala Leu Leu Phe Val Pro Arg Arg Ala Pro Phe Asp Leu Phe
                340                 345                 350
Glu Asn Arg Lys Lys Lys Asn Asn Ile Lys Leu Tyr Val Arg Arg Val
            355                 360                 365
Phe Ile Met Asp Asn Cys Glu Glu Leu Ile Pro Glu Tyr Leu Asn Phe
        370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                    405                 410                 415
Val Lys Lys Cys Leu Glu Leu Phe Thr Glu Leu Ala Glu Asp Lys Glu
                420                 425                 430
Asn Tyr Lys Lys Phe Tyr Glu Gln Phe Ser Lys Asn Ile Lys Leu Gly
            435                 440                 445
Ile His Glu Asp Ser Gln Asn Arg Lys Lys Leu Ser Glu Leu Leu Arg
        450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                    485                 490                 495
Glu Thr Lys Asp Gln Val Ala Asn Ser Ala Phe Val Glu Arg Leu Arg
                500                 505                 510
Lys His Gly Leu Glu Val Ile Tyr Met Ile Glu Pro Ile Asp Glu Tyr
            515                 520                 525
Cys Val Gln Gln Leu Lys Glu Phe Glu Gly Lys Thr Leu Val Ser Val
        530                 535                 540
Thr Lys Glu Gly Leu Glu Leu Pro Glu Asp Glu Glu Lys Lys Lys
545                 550                 555                 560
Gln Glu Glu Lys Lys Thr Lys Phe Glu Asn Leu Cys Lys Ile Met Lys
                    565                 570                 575
```

```
Asp Ile Leu Glu Lys Lys Val Glu Lys Val Val Ser Asn Arg Leu
            580                 585                 590

Val Thr Ser Pro Cys Cys Ile Val Thr Ser Thr Tyr Gly Trp Thr Ala
            595                 600                 605

Asn Met Glu Arg Ile Met Lys Ala Gln Ala Leu Arg Asp Asn Ser Thr
        610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
            675                 680                 685

Tyr Arg Met Ile Lys Leu Gly Leu Gly Ile Asp Glu Asp Pro Thr
            690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730
```

```
<210> SEQ ID NO 20
<211> LENGTH: 198
<212> TYPE: PRT
<213> ORGANISM: Homo Sapiens

<400> SEQUENCE: 20

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195
```

```
<210> SEQ ID NO 21
<211> LENGTH: 154
<212> TYPE: PRT
<213> ORGANISM: Homo Sapiens

<400> SEQUENCE: 21

Met Gly Leu Ser Asp Gly Glu Trp Gln Leu Val Leu Asn Val Trp Gly
1               5                   10                  15

Lys Val Glu Ala Asp Ile Pro Gly His Gly Gln Glu Val Leu Ile Arg
            20                  25                  30

Leu Phe Lys Gly His Pro Glu Thr Leu Glu Lys Phe Asp Lys Phe Lys
        35                  40                  45

His Leu Lys Ser Glu Asp Glu Met Lys Ala Ser Glu Asp Leu Lys Lys
    50                  55                  60

His Gly Ala Thr Val Leu Thr Ala Leu Gly Gly Ile Leu Lys Lys Lys
65                  70                  75                  80

Gly His His Glu Ala Glu Ile Lys Pro Leu Ala Gln Ser His Ala Thr
                85                  90                  95

Lys His Lys Ile Pro Val Lys Tyr Leu Glu Phe Ile Ser Glu Cys Ile
            100                 105                 110

Ile Gln Val Leu Gln Ser Lys His Pro Gly Asp Phe Gly Ala Asp Ala
        115                 120                 125

Gln Gly Ala Met Asn Lys Ala Leu Glu Leu Phe Arg Lys Asp Met Ala
    130                 135                 140

Ser Asn Tyr Lys Glu Leu Gly Phe Gln Gly
145                 150

<210> SEQ ID NO 22
<211> LENGTH: 352
<212> TYPE: PRT
<213> ORGANISM: Rattus norvegicus

<400> SEQUENCE: 22

Met Lys Ser Leu Val Leu Leu Leu Cys Phe Ala Gln Leu Trp Ser Cys
1               5                   10                  15

Gln Ser Ala Pro Gln Gly Ala Gly Leu Gly Phe Arg Glu Leu Ala Cys
            20                  25                  30

Asp Asp Pro Glu Thr Glu His Val Ala Leu Ile Ala Val His Tyr Leu
        35                  40                  45

Asn Lys His Leu Leu Gln Gly Phe Arg Gln Ile Leu Asn Gln Ile Asp
    50                  55                  60

Lys Val Lys Val Trp Ser Arg Arg Pro Phe Gly Gln Val Tyr Glu Leu
65                  70                  75                  80

Glu Ile Asp Thr Leu Glu Thr Thr Cys His Ala Leu Asp Pro Thr Pro
                85                  90                  95

Leu Ala Asn Cys Ser Val Arg Gln Gln Ala Glu His Ala Val Glu Gly
            100                 105                 110

Asp Cys Asp Phe His Ile Leu Lys Gln Asp Gly Gln Phe Arg Val Leu
        115                 120                 125

His Ala Gln Cys His Ser Thr Pro Asp Ser Ala Glu Asp Val Arg Lys
    130                 135                 140

Phe Cys Pro Arg Cys Pro Ile Leu Ile Arg Phe Asn Asp Thr Asn Val
145                 150                 155                 160

Val His Thr Val Lys Thr Ala Leu Ala Ala Phe Asn Ala Gln Asn Asn
                165                 170                 175

Gly Thr Tyr Phe Lys Leu Val Glu Ile Ser Arg Ala Gln Asn Val Pro
```

```
                180             185             190
Phe Pro Val Ser Thr Leu Val Glu Phe Val Ile Ala Ala Thr Asp Cys
            195                 200                 205

Thr Gly Gln Glu Val Thr Asp Pro Ala Lys Cys Asn Leu Leu Ala Glu
        210                 215                 220

Lys Gln Tyr Gly Phe Cys Lys Ala Thr Leu Ile His Arg Leu Gly Gly
225                 230                 235                 240

Glu Glu Val Ser Val Ala Cys Lys Leu Phe Gln Thr Gln Pro Gln Pro
                245                 250                 255

Ala Asn Ala Asn Pro Ala Gly Pro Ala Pro Thr Val Gly Gln Ala Ala
            260                 265                 270

Pro Val Ala Pro Pro Ala Gly Pro Pro Glu Ser Val Val Gly Pro
        275                 280                 285

Val Ala Val Pro Leu Gly Leu Pro Asp His Arg Thr His His Asp Leu
        290                 295                 300

Arg His Ala Phe Ser Pro Val Ala Ser Val Glu Ser Ala Ser Gly Glu
305                 310                 315                 320

Val Leu His Ser Pro Lys Val Gly Gln Pro Gly Asp Ala Gly Ala Ala
                325                 330                 335

Gly Pro Val Ala Pro Leu Cys Pro Gly Arg Val Arg Tyr Phe Lys Ile
            340                 345                 350

<210> SEQ ID NO 23
<211> LENGTH: 360
<212> TYPE: PRT
<213> ORGANISM: Homo Sapiens

<400> SEQUENCE: 23

Met Asn Tyr Thr Glu Ser Ser Pro Leu Arg Glu Ser Thr Ala Ile Gly
1               5                   10                  15

Phe Thr Pro Glu Leu Glu Ser Ile Ile Pro Val Pro Ser Asn Lys Thr
            20                  25                  30

Thr Cys Glu Asn Trp Arg Glu Ile His His Leu Val Phe His Val Ala
        35                  40                  45

Asn Ile Cys Phe Ala Val Gly Leu Val Ile Pro Thr Thr Leu His Leu
    50                  55                  60

His Met Ile Phe Leu Arg Gly Met Leu Thr Leu Gly Cys Thr Leu Tyr
65                  70                  75                  80

Ile Val Trp Ala Thr Leu Tyr Arg Cys Ala Leu Asp Ile Met Ile Trp
                85                  90                  95

Asn Ser Val Phe Leu Gly Val Asn Ile Leu His Leu Ser Tyr Leu Leu
            100                 105                 110

Tyr Lys Lys Arg Pro Val Lys Ile Glu Lys Glu Leu Ser Gly Met Tyr
        115                 120                 125

Arg Arg Leu Phe Glu Pro Leu Arg Val Pro Pro Asp Leu Phe Arg Arg
    130                 135                 140

Leu Thr Gly Gln Phe Cys Met Ile Gln Thr Leu Lys Lys Gly Gln Thr
145                 150                 155                 160

Tyr Ala Ala Glu Asp Lys Thr Ser Val Asp Asp Arg Leu Ser Ile Leu
                165                 170                 175

Leu Lys Gly Lys Met Lys Val Ser Tyr Arg Gly His Phe Leu His Asn
            180                 185                 190

Ile Tyr Pro Cys Ala Phe Ile Asp Ser Pro Glu Phe Arg Ser Thr Gln
        195                 200                 205
```

```
Met His Lys Gly Glu Lys Phe Gln Val Thr Ile Ile Ala Asp Asp Asn
            210                 215                 220

Cys Arg Phe Leu Cys Trp Ser Arg Glu Arg Leu Thr Tyr Phe Leu Glu
225                 230                 235                 240

Ser Glu Pro Phe Leu Tyr Glu Ile Phe Arg Tyr Leu Ile Gly Lys Asp
                245                 250                 255

Ile Thr Asn Lys Leu Tyr Ser Leu Asn Asp Pro Thr Leu Asn Asp Lys
            260                 265                 270

Lys Ala Lys Lys Leu Glu His Gln Leu Ser Leu Cys Thr Gln Ile Ser
            275                 280                 285

Met Leu Glu Met Arg Asn Ser Ile Ala Ser Ser Ser Asp Ser Asp Asp
290                 295                 300

Gly Leu His Gln Phe Leu Arg Gly Thr Ser Ser Met Ser Ser Leu His
305                 310                 315                 320

Val Ser Ser Pro His Gln Arg Ala Ser Ala Lys Met Lys Pro Ile Glu
                325                 330                 335

Glu Gly Ala Glu Asp Asp Asp Val Phe Glu Pro Ala Ser Pro Asn
                340                 345                 350

Thr Leu Lys Val His Gln Leu Pro
            355                 360

<210> SEQ ID NO 24
<211> LENGTH: 724
<212> TYPE: PRT
<213> ORGANISM: Homo Sapiens

<400> SEQUENCE: 24

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
                20                  25                  30

Tyr Ser Asn Lys Glu Ile Phe Leu Arg Glu Leu Ile Ser Asn Ala Ser
            35                  40                  45

Asp Ala Leu Asp Lys Ile Arg Tyr Glu Ser Leu Thr Asp Pro Ser Lys
50                  55                  60

Leu Asp Ser Gly Lys Glu Leu Lys Ile Asp Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220
```

```
Ile Ser Asp Asp Glu Ala Glu Glu Lys Gly Lys Glu Glu
225                 230                 235                 240

Asp Lys Asp Asp Glu Lys Pro Lys Ile Glu Asp Val Gly Ser Asp
                245                 250                 255

Glu Glu Asp Asp Ser Gly Lys Asp Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
            290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Asn Asn
            340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
        435                 440                 445

Arg Arg Leu Ser Glu Leu Leu Arg Tyr His Thr Ser Gln Ser Gly Asp
            450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
        515                 520                 525

Asp Gly Lys Ser Leu Val Ser Val Thr Lys Glu Gly Leu Glu Leu Pro
            530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
        595                 600                 605

Gln Ala Leu Arg Asp Asn Ser Thr Met Gly Tyr Met Met Ala Lys Lys
            610                 615                 620

His Leu Glu Ile Asn Pro Asp His Pro Ile Val Glu Thr Leu Arg Gln
625                 630                 635                 640
```

```
Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Ala Ala Glu Pro Asn Ala Ala Val
    690                 695                 700

Pro Asp Glu Ile Pro Pro Leu Glu Gly Asp Glu Ala Ser Arg Met
705                 710                 715                 720

Glu Glu Val Asp

<210> SEQ ID NO 25
<211> LENGTH: 1196
<212> TYPE: PRT
<213> ORGANISM: Mus musculus

<400> SEQUENCE: 25

Met Asn Thr Asp Ser Gly Gly Cys Ala Arg Lys Ala Ala Met Ser
1               5                   10                  15

Val Thr Leu Thr Ser Val Lys Arg Val Gln Ser Ser Pro Asn Leu Leu
            20                  25                  30

Ala Ala Gly Arg Glu Ser Gln Ser Pro Asp Ser Ala Trp Arg Ser Tyr
        35                  40                  45

Asn Asp Arg Asn Pro Glu Thr Leu Asn Gly Asp Ala Thr Tyr Ser Ser
    50                  55                  60

Leu Ala Ala Lys Gly Phe Arg Ser Val Arg Pro Asn Leu Gln Asp Lys
65                  70                  75                  80

Arg Ser Pro Thr Gln Ser Gln Ile Thr Ile Asn Gly Asn Ser Gly Gly
                85                  90                  95

Ala Val Ser Pro Val Ser Tyr Tyr Gln Arg Pro Phe Ser Pro Ser Ala
            100                 105                 110

Tyr Ser Leu Pro Ala Ser Leu Asn Ser Ser Ile Ile Met Gln His Gly
        115                 120                 125

Arg Ser Leu Asp Ser Ala Glu Thr Tyr Ser Gln His Ala Gln Ser Leu
    130                 135                 140

Asp Gly Thr Met Gly Ser Ser Ile Pro Leu Tyr Arg Ser Ser Glu Glu
145                 150                 155                 160

Glu Lys Arg Val Thr Val Ile Lys Ala Pro His Tyr Pro Gly Ile Gly
                165                 170                 175

Pro Val Asp Glu Ser Gly Ile Pro Thr Ala Ile Arg Thr Thr Val Asp
            180                 185                 190

Arg Pro Lys Asp Trp Tyr Lys Thr Met Phe Lys Gln Ile His Met Val
        195                 200                 205

His Lys Pro Asp Glu Asp Thr Asp Met Tyr Asn Thr Pro Tyr Thr Tyr
    210                 215                 220

Asn Ala Gly Leu Tyr Asn Ser Pro Tyr Ser Ala Gln Ser His Pro Ala
225                 230                 235                 240

Ala Lys Thr Gln Thr Tyr Arg Pro Leu Ser Lys Ser His Ser Asp Asn
                245                 250                 255

Gly Thr Asp Ala Phe Lys Glu Val Pro Ser Pro Val Pro Pro Pro His
            260                 265                 270

Val Pro Pro Arg Pro Arg Asp Gln Ser Ser Thr Leu Lys His Asp Trp
        275                 280                 285
```

```
Asp Pro Pro Asp Arg Lys Val Asp Thr Arg Lys Phe Arg Ser Glu Pro
    290                 295                 300

Arg Ser Ile Phe Glu Tyr Glu Pro Gly Lys Ser Ser Ile Leu Gln His
305                 310                 315                 320

Glu Arg Pro Val Ser Ile Tyr Gln Ser Ser Ile Asp Arg Ser Leu Glu
                325                 330                 335

Arg Pro Ser Ser Ser Ala Ser Met Ala Gly Asp Phe Arg Lys Arg Arg
                340                 345                 350

Lys Ser Glu Pro Ala Val Gly Pro Leu Arg Gly Leu Gly Asp Gln Ser
        355                 360                 365

Ser Ser Arg Thr Ser Pro Gly Arg Ala Asp Leu Pro Gly Ser Ser Ser
    370                 375                 380

Thr Phe Thr Lys Ser Phe Ile Ser Ser Pro Ser Ser Pro Ser Arg
385                 390                 395                 400

Ala Gln Gly Gly Asp Ser Lys Met Cys Pro Pro Leu Cys Ser Tyr
                405                 410                 415

Ser Gly Leu Asn Gly Thr Pro Ser Gly Glu Leu Glu Cys Cys Asn Ala
        420                 425                 430

Tyr Arg Gln His Leu Asp Val Pro Gly Asp Ser Gln Arg Ala Ile Thr
            435                 440                 445

Phe Lys Asn Gly Trp Gln Met Ala Arg Gln Asn Ala Glu Ile Trp Ser
450                 455                 460

Ser Thr Glu Glu Thr Val Ser Pro Lys Ile Lys Ser Arg Ser Cys Asp
465                 470                 475                 480

Asp Leu Leu Asn Asp Cys Asp Ser Phe Pro Asp Pro Lys Thr Lys
                485                 490                 495

Ser Glu Ser Met Gly Ser Leu Leu Cys Glu Glu Asp Ser Lys Glu Ser
            500                 505                 510

Cys Pro Met Thr Trp Ala Ser Pro Tyr Ile Gln Glu Val Cys Gly Asn
        515                 520                 525

Ser Arg Ser Arg Leu Lys His Arg Ser Ala His Asn Ala Pro Gly Phe
    530                 535                 540

Leu Lys Met Tyr Lys Lys Met His Arg Ile Asn Arg Lys Asp Leu Met
545                 550                 555                 560

Asn Ser Glu Val Ile Cys Ser Val Lys Ser Arg Ile Leu Gln Tyr Glu
                565                 570                 575

Lys Glu Gln Gln His Arg Gly Leu Leu His Gly Trp Ser Gln Ser Ser
            580                 585                 590

Thr Glu Glu Val Pro Arg Asp Val Val Pro Thr Arg Ile Ser Glu Phe
        595                 600                 605

Glu Lys Leu Ile Gln Lys Ser Lys Ser Met Pro Asn Leu Gly Asp Glu
    610                 615                 620

Met Leu Ser Pro Ile Thr Leu Glu Pro Pro Gln Asn Gly Leu Cys Pro
625                 630                 635                 640

Lys Arg Arg Phe Ser Ile Glu Ser Leu Leu Glu Glu Thr Gln Val
                645                 650                 655

Arg His Pro Ser Gln Gly Gln Arg Ser Cys Lys Ser Asn Thr Leu Val
            660                 665                 670

Pro Ile His Ile Glu Val Thr Ser Asp Glu Gln Pro Arg Thr His Met
        675                 680                 685

Glu Phe Ser Asp Ser Asp Gln Asp Gly Val Val Ser Asp His Ser Asp
    690                 695                 700

Tyr Val His Val Glu Gly Ser Ser Phe Cys Ser Glu Ser Asp Phe Asp
```

```
                705                 710                 715                 720
            His Phe Ser Phe Thr Ser Ser Glu Ser Phe Tyr Gly Ser Ser His His
                        725                 730                 735

His His His His His His His Arg His Leu Ile Ser Ser Cys Lys
                        740                 745                 750

Gly Arg Cys Pro Ala Ser Tyr Thr Arg Phe Thr Thr Met Leu Lys His
                        755                 760                 765

Glu Arg Ala Lys His Glu Asn Met Asp Arg Pro Arg Arg Gln Glu Met
                        770                 775                 780

Asp Pro Gly Leu Ser Lys Leu Ala Phe Leu Val Ser Pro Val Pro Phe
            785                 790                 795                 800

Arg Arg Lys Lys Ile Leu Thr Pro Gln Lys Gln Thr Glu Lys Ala Lys
                        805                 810                 815

Cys Lys Ala Ser Val Val Glu Ala Leu Asp Ser Ala Leu Lys Asp Ile
                        820                 825                 830

Cys Asp Gln Ile Lys Ala Glu Lys Arg Arg Gly Ser Leu Pro Asp Asn
                        835                 840                 845

Ser Ile Leu His Arg Leu Ile Ser Glu Leu Leu Pro Gln Ile Pro Glu
                        850                 855                 860

Arg Asn Ser Ser Leu His Ala Leu Lys Arg Ser Pro Met His Gln Pro
            865                 870                 875                 880

Phe His Pro Leu Pro Pro Asp Gly Ala Ser His Cys Pro Leu Tyr Gln
                        885                 890                 895

Asn Asp Cys Gly Arg Met Pro His Ser Ala Ser Phe Pro Asp Val Asp
                        900                 905                 910

Thr Thr Ser Asn Tyr His Ala Gln Asp Tyr Gly Ser Ala Leu Ser Leu
                        915                 920                 925

Gln Asp His Glu Ser Pro Arg Ser Tyr Ser Ser Thr Leu Thr Asp Leu
                        930                 935                 940

Gly Arg Ser Ala Ser Arg Glu Arg Arg Gly Thr Pro Glu Lys Glu Val
            945                 950                 955                 960

Lys Leu Pro Ala Lys Ala Val Tyr Asp Phe Lys Ala Gln Thr Ser Lys
                        965                 970                 975

Glu Leu Ser Phe Lys Lys Gly Asp Thr Val Tyr Ile Leu Arg Lys Ile
                        980                 985                 990

Asp Gln Asn Trp Tyr Glu Gly Glu His His Gly Arg Val Gly Ile Phe
                        995                 1000                1005

Pro Ile Ser Tyr Val Glu Lys Leu Thr Pro Pro Glu Lys Ala Gln
                        1010                1015                1020

Pro Ala Arg Pro Pro Pro Val Gln Pro Gly Glu Ile Gly Glu
                        1025                1030                1035

Ala Ile Ala Lys Tyr Asn Phe Asn Ala Asp Thr Asn Val Glu Leu
                        1040                1045                1050

Ser Leu Arg Lys Gly Asp Arg Ile Ile Leu Leu Lys Arg Val Asp
                        1055                1060                1065

Gln Asn Trp Tyr Glu Gly Lys Ile Pro Gly Thr Asn Arg Gln Gly
                        1070                1075                1080

Ile Phe Pro Val Ser Tyr Val Glu Val Val Lys Arg Asn Ala Lys
                        1085                1090                1095

Gly Ala Glu Asp Tyr Pro Asp Pro Pro Leu Pro His Ser Tyr Ser
                        1100                1105                1110

Ser Asp Arg Ile Tyr Thr Leu Ser Ser Asn Lys Pro Gln Arg Pro
                        1115                1120                1125
```

Gly Phe Ser His Glu Asn Ile Gln Gly Gly Glu Pro Phe Gln
            1130                1135                1140

Ala Leu Tyr Asn Tyr Thr Pro Arg Asn Glu Asp Glu Leu Glu Leu
        1145                1150                1155

Arg Glu Ser Asp Val Val Asp Val Met Glu Lys Cys Asp Asp Gly
    1160                1165                1170

Trp Phe Val Gly Thr Ser Arg Arg Thr Lys Phe Phe Gly Thr Phe
    1175                1180                1185

Pro Gly Asn Tyr Val Lys Arg Leu
    1190                1195

<210> SEQ ID NO 26
<211> LENGTH: 1196
<212> TYPE: PRT
<213> ORGANISM: Rattus norvegicus

<400> SEQUENCE: 26

Met Asn Thr Asp Ser Gly Gly Cys Ala Arg Lys Arg Ala Ala Met Ser
1               5                   10                  15

Val Thr Leu Thr Ser Val Lys Arg Val Gln Ser Ser Pro Asn Leu Leu
            20                  25                  30

Ala Ala Gly Arg Glu Ser His Ser Pro Asp Ser Ala Trp Arg Ser Tyr
        35                  40                  45

Asn Gly Arg Asn Pro Glu Thr Leu Asn Gly Asp Ala Thr Tyr Ser Ser
    50                  55                  60

Leu Ala Ala Lys Gly Phe Arg Ser Val Arg Pro Asn Leu Gln Asp Lys
65                  70                  75                  80

Lys Ser Pro Thr Gln Ser His Ile Thr Ile Asn Gly Asn Ser Gly Gly
                85                  90                  95

Ala Val Ser Pro Val Ser Tyr Tyr Gln Arg Pro Phe Ser Pro Ser Ala
            100                 105                 110

Tyr Ser Leu Pro Ala Ser Leu Asn Ser Ser Ile Ile Met Pro His Gly
        115                 120                 125

Arg Ser Leu Asp Ser Ala Glu Thr Tyr Ser Gln His Ala Gln Ser Leu
    130                 135                 140

Asp Gly Thr Met Gly Ser Ser Ile Pro Leu Tyr Arg Ser Ser Glu Glu
145                 150                 155                 160

Glu Lys Arg Val Thr Val Ile Lys Ala Pro His Tyr Pro Gly Ile Gly
                165                 170                 175

Pro Val Asp Glu Ser Gly Ile Pro Thr Ala Ile Arg Thr Thr Val Asp
            180                 185                 190

Arg Pro Lys Asp Trp Tyr Lys Thr Met Phe Lys Gln Ile His Met Val
        195                 200                 205

His Lys Pro Asp Glu Asp Thr Asp Met Tyr Asn Thr Pro Tyr Thr Tyr
    210                 215                 220

Asn Ala Gly Leu Tyr Asn Ser Pro Tyr Ser Ala Gln Ser His Pro Ala
225                 230                 235                 240

Ala Lys Thr Gln Thr Tyr Arg Pro Leu Ser Lys Ser His Ser Asp Asn
                245                 250                 255

Gly Thr Asp Ala Phe Lys Glu Ala Pro Ser Val Pro Pro Pro His
            260                 265                 270

Val Pro Pro Arg Pro Arg Asp Gln Ser Ser Thr Glu Lys His Asp Trp
        275                 280                 285

Asp Pro Pro Asp Arg Lys Val Asp Thr Arg Lys Phe Arg Ser Glu Pro

```
            290                 295                 300
Arg Ser Ile Phe Glu Tyr Glu Pro Gly Lys Ser Ser Ile Leu Gln His
305                 310                 315                 320

Glu Arg Pro Val Ser Val Tyr Gln Ser Ser Ile Asp Arg Ser Leu Glu
                325                 330                 335

Arg Pro Ser Ser Ser Ala Ser Met Ala Gly Asp Phe Arg Lys Arg Arg
                340                 345                 350

Lys Ser Glu Pro Ala Val Gly Pro Pro Arg Gly Leu Gly Asp His Ser
            355                 360                 365

Ser Ser Arg Thr Ser Pro Gly Arg Ala Asp Leu Pro Gly Ser Ser Ser
        370                 375                 380

Thr Phe Thr Thr Ser Phe Ile Ser Ser Pro Ser Ser Pro Ser Arg
385                 390                 395                 400

Ala Gln Gly Gly Asp Asp Ser Lys Met Cys Pro Pro Leu Cys Ser Tyr
                405                 410                 415

Ser Gly Leu Asn Gly Ser Pro Ser Ser Glu Leu Glu Cys Cys Gly Ala
                420                 425                 430

Tyr Arg Arg His Leu Asp Val Pro Gln Asp Ser Gln Arg Ala Ile Thr
            435                 440                 445

Phe Lys Asn Gly Trp Gln Met Ala Arg Gln Asn Ala Glu Ile Trp Ser
        450                 455                 460

Ser Thr Glu Glu Ala Val Ser Pro Lys Ile Lys Ser Arg Ser Cys Asp
465                 470                 475                 480

Asp Leu Leu Asn Asp Asp Cys Gly Ser Phe Pro Asp Pro Lys Thr Lys
                485                 490                 495

Ser Glu Ser Met Gly Ser Leu Leu Cys Asp Glu Gly Ser Lys Glu Ser
                500                 505                 510

Asp Pro Met Thr Trp Thr Ser Pro Tyr Ile Pro Glu Val Cys Gly Asn
            515                 520                 525

Ser Arg Ser Arg Leu Lys His Arg Ser Ala His Asn Ala Pro Gly Phe
        530                 535                 540

Leu Lys Met Tyr Lys Lys Met His Arg Ile Asn Arg Lys Asp Leu Met
545                 550                 555                 560

Asn Ser Glu Val Ile Cys Ser Val Lys Ser Arg Ile Leu Gln Tyr Glu
                565                 570                 575

Lys Glu Gln Gln His Arg Gly Leu Leu His Gly Trp Ser Gln Ser Ser
            580                 585                 590

Thr Glu Glu Val Pro Arg Asp Val Pro Thr Arg Ile Ser Glu Phe
        595                 600                 605

Glu Lys Leu Ile Gln Lys Ser Lys Ser Met Pro Asn Leu Gly Asp Glu
    610                 615                 620

Met Leu Ser Pro Val Thr Leu Glu Pro Pro Gln Asn Gly Leu Cys Pro
625                 630                 635                 640

Lys Arg Arg Phe Ser Ile Glu Ser Leu Leu Glu Glu Thr Gln Val
                645                 650                 655

Arg His Pro Ser Gln Gly Gln Arg Ser Cys Lys Ser Asn Thr Leu Val
            660                 665                 670

Pro Ile His Ile Glu Val Thr Ser Asp Glu Gln Pro Arg Thr His Met
        675                 680                 685

Glu Phe Ser Asp Ser Asp Gln Asp Gly Val Val Ser Asp His Ser Asp
    690                 695                 700

Asn Val His Val Glu Arg Ser Ser Phe Cys Ser Glu Ser Asp Phe Asp
705                 710                 715                 720
```

```
His Phe Ser Phe Thr Ser Ser Glu Ser Phe Tyr Gly Ser Ser His His
                725                 730                 735
His His His His His His His Gly His Phe Ile Ser Ser Cys Lys
        740                 745                 750
Gly Arg Cys Pro Ala Ser Tyr Thr Arg Phe Thr Thr Met Leu Lys His
        755                 760                 765
Glu Arg Ala Lys His Glu Asn Ile Asp Arg Pro Arg Gln Asp Met
770                 775                 780
Asp Pro Gly Leu Ser Lys Leu Ala Phe Leu Val Ser Pro Val Pro Phe
785                 790                 795                 800
Arg Arg Lys Lys Val Leu Thr Pro Gln Lys Gln Thr Glu Gln Ala Lys
                805                 810                 815
Cys Lys Ala Ser Val Val Glu Ala Leu Asp Ser Ala Leu Lys Asp Ile
                820                 825                 830
Cys Asp Gln Ile Lys Ala Glu Lys Arg Arg Gly Ser Leu Pro Asp Asn
                835                 840                 845
Ser Ile Leu His Arg Leu Ile Ser Glu Leu Leu Pro Gln Ile Pro Lys
                850                 855                 860
Arg Asn Ser Ser Leu Asn Ala Leu Lys Arg Ser Pro Met His Gln Pro
865                 870                 875                 880
Phe His Pro Leu Pro Gln Asp Gly Ala Ile His Cys Pro Leu Tyr Gln
                885                 890                 895
Asn Asp Cys Gly Arg Met Pro His Ser Ala Ser Phe Pro Asp Val Asp
                900                 905                 910
Thr Thr Ser Ser Tyr His Ala Gln Asp Tyr Gly Ser Val Leu Ser Leu
                915                 920                 925
Gln Asp His Glu Ser Pro Arg Ser Tyr Ser Ser Thr Leu Thr Asp Leu
                930                 935                 940
Gly Arg Ser Val Ser Arg Glu Arg Gly Thr Pro Glu Lys Glu Val
945                 950                 955                 960
Lys Leu Pro Ala Lys Ala Val Tyr Asp Phe Lys Ala Gln Thr Ser Lys
                965                 970                 975
Glu Leu Ser Phe Lys Lys Gly Asp Thr Val Tyr Ile Leu Arg Lys Ile
                980                 985                 990
Asp Gln Asn Trp Tyr Glu Gly Glu His His Gly Arg Val Gly Ile Phe
                995                 1000                1005
Pro Ile Ser Tyr Val Glu Lys Leu Thr Pro Pro Glu Lys Ala Gln
        1010                1015                1020
Pro Ala Arg Pro Pro Pro Val Gln Pro Gly Glu Ile Gly Glu
        1025                1030                1035
Ala Ile Ala Lys Tyr Asn Phe Asn Ala Asp Thr Asn Val Glu Leu
        1040                1045                1050
Ser Leu Arg Lys Gly Asp Arg Ile Ile Leu Leu Lys Arg Val Asp
        1055                1060                1065
Gln Asn Trp Tyr Glu Gly Lys Ile Pro Gly Thr Asn Arg Gln Gly
        1070                1075                1080
Ile Phe Pro Val Ser Tyr Val Glu Val Val Lys Arg Asn Thr Lys
        1085                1090                1095
Gly Ser Glu Asp Tyr Pro Asp Pro Pro Leu Pro His Ser Tyr Ser
        1100                1105                1110
Ser Asp Arg Ile Tyr Ser Leu Ser Ser Asn Lys Pro Gln Arg Pro
        1115                1120                1125
```

Val Phe Ser His Glu Asn Ile Gln Gly Gly Gly Glu Pro Phe Gln
1130                1135                    1140

Ala Leu Tyr Asn Tyr Thr Pro Arg Asn Glu Asp Glu Leu Glu Leu
1145                1150                    1155

Arg Glu Ser Asp Val Val Asp Val Met Glu Lys Cys Asp Asp Gly
1160                1165                    1170

Trp Phe Val Gly Thr Ser Arg Arg Thr Lys Phe Phe Gly Thr Phe
1175                1180                    1185

Pro Gly Asn Tyr Val Lys Arg Leu
1190                1195

<210> SEQ ID NO 27
<211> LENGTH: 600
<212> TYPE: PRT
<213> ORGANISM: Homo Sapiens

<400> SEQUENCE: 27

Met Ser Arg Val Ala Lys Tyr Arg Arg Gln Val Ser Glu Asp Pro Asp
1               5                   10                  15

Ile Asp Ser Leu Leu Glu Thr Leu Ser Pro Glu Glu Met Glu Glu Leu
                20                  25                  30

Glu Lys Glu Leu Asp Val Val Asp Pro Asp Gly Ser Val Pro Val Gly
            35                  40                  45

Leu Arg Gln Arg Asn Gln Thr Glu Lys Gln Ser Thr Gly Val Tyr Asn
50                  55                  60

Arg Glu Ala Met Leu Asn Phe Cys Glu Lys Thr Lys Lys Leu Met Glu
65                  70                  75                  80

Gln Arg Glu Met Ser Met Asp Glu Ser Lys Gln Val Glu Thr Lys Thr
                85                  90                  95

Asp Ala Lys Asn Gly Glu Glu Arg Gly Arg Asp Ala Ser Lys Lys Ala
            100                 105                 110

Leu Gly Pro Arg Arg Asp Ser Asp Leu Gly Lys Glu Pro Lys Arg Gly
        115                 120                 125

Gly Leu Lys Lys Ser Phe Ser Arg Asp Arg Asp Glu Ala Gly Gly Lys
    130                 135                 140

Ser Gly Glu Lys Pro Lys Glu Glu Lys Ile Ile Arg Gly Ile Asp Lys
145                 150                 155                 160

Gly Arg Val Arg Ala Ala Val Asp Lys Lys Glu Ala Gly Lys Asp Gly
                165                 170                 175

Arg Gly Glu Glu Arg Ala Val Ala Thr Lys Lys Glu Glu Lys Lys
            180                 185                 190

Gly Ser Asp Arg Asn Thr Gly Leu Ser Arg Asp Lys Asp Lys Lys Arg
        195                 200                 205

Glu Glu Met Lys Glu Val Ala Lys Lys Glu Asp Glu Lys Val Lys
    210                 215                 220

Gly Glu Arg Arg Asn Thr Asp Thr Arg Lys Glu Gly Glu Lys Met Lys
225                 230                 235                 240

Arg Ala Gly Gly Asn Thr Asp Met Lys Lys Glu Asp Glu Lys Val Lys
                245                 250                 255

Arg Gly Thr Gly Asn Thr Asp Thr Lys Lys Asp Asp Gly Lys Val Lys
            260                 265                 270

Lys Asn Glu Pro Leu His Glu Lys Glu Ala Lys Asp Asp Ser Lys Thr
        275                 280                 285

Lys Thr Pro Glu Lys Gln Thr Pro Ser Gly Pro Thr Lys Pro Ser Glu
    290                 295                 300

Gly Pro Ala Lys Val Glu Glu Ala Ala Pro Ser Ile Phe Asp Glu
305                 310                 315                 320

Pro Leu Glu Arg Val Lys Asn Asn Asp Pro Glu Met Thr Glu Val Asn
                325                 330                 335

Val Asn Asn Ser Asp Cys Ile Thr Asn Glu Ile Leu Val Arg Phe Thr
                340                 345                 350

Glu Ala Leu Glu Phe Asn Thr Val Val Lys Leu Phe Ala Leu Ala Asn
                355                 360                 365

Thr Arg Ala Asp Asp His Val Ala Phe Ala Ile Ala Ile Met Leu Lys
370                 375                 380

Ala Asn Lys Thr Ile Thr Ser Leu Asn Leu Asp Ser Asn His Ile Thr
385                 390                 395                 400

Gly Lys Gly Ile Leu Ala Ile Phe Arg Ala Leu Leu Gln Asn Asn Thr
                405                 410                 415

Leu Thr Glu Leu Arg Phe His Asn Gln Arg His Ile Cys Gly Gly Lys
                420                 425                 430

Thr Glu Met Glu Ile Ala Lys Leu Leu Lys Glu Asn Thr Thr Leu Leu
                435                 440                 445

Lys Leu Gly Tyr His Phe Glu Leu Ala Gly Pro Arg Met Thr Val Thr
450                 455                 460

Asn Leu Leu Ser Arg Asn Met Asp Lys Gln Arg Gln Lys Arg Leu Gln
465                 470                 475                 480

Glu Gln Arg Gln Ala Gln Ala Lys Gly Glu Lys Lys Asp Leu Leu
                485                 490                 495

Glu Val Pro Lys Ala Gly Ala Val Ala Lys Gly Ser Pro Lys Pro Ser
                500                 505                 510

Pro Gln Pro Ser Pro Lys Pro Ser Pro Lys Asn Ser Pro Lys Lys Gly
                515                 520                 525

Gly Ala Pro Ala Ala Pro Pro Pro Pro Pro Pro Leu Ala Pro Pro
530                 535                 540

Leu Ile Met Glu Asn Leu Lys Asn Ser Leu Ser Pro Ala Thr Gln Arg
545                 550                 555                 560

Lys Met Gly Asp Lys Val Leu Pro Ala Gln Lys Asn Ser Arg Asp
                565                 570                 575

Gln Leu Leu Ala Ala Ile Arg Ser Ser Asn Leu Lys Gln Leu Lys Lys
                580                 585                 590

Val Glu Val Pro Lys Leu Leu Gln
                595                 600

<210> SEQ ID NO 28
<211> LENGTH: 172
<212> TYPE: PRT
<213> ORGANISM: Homo Sapiens

<400> SEQUENCE: 28

Met Ser Ser Lys Lys Ala Lys Thr Lys Thr Thr Lys Lys Arg Pro Gln
1               5                   10                  15

Arg Ala Thr Ser Asn Val Phe Ala Met Phe Asp Gln Ser Gln Ile Gln
                20                  25                  30

Glu Phe Lys Glu Ala Phe Asn Met Ile Asp Gln Asn Arg Asp Gly Phe
                35                  40                  45

Ile Asp Lys Glu Asp Leu His Asp Met Leu Ala Ser Leu Gly Lys Asn
                50                  55                  60

Pro Thr Asp Ala Tyr Leu Asp Ala Met Met Asn Glu Ala Pro Gly Pro

```
                65                  70                  75                  80
Ile Asn Phe Thr Met Phe Leu Thr Met Phe Gly Glu Lys Leu Asn Gly
                    85                  90                  95

Thr Asp Pro Glu Asp Val Ile Arg Asn Ala Phe Ala Cys Phe Asp Glu
                    100                 105                 110

Glu Ala Thr Gly Thr Ile Gln Glu Asp Tyr Leu Arg Glu Leu Leu Thr
                    115                 120                 125

Thr Met Gly Asp Arg Phe Thr Asp Glu Glu Val Asp Glu Leu Tyr Arg
        130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp
                    165                 170

<210> SEQ ID NO 29
<211> LENGTH: 675
<212> TYPE: PRT
<213> ORGANISM: Homo Sapiens

<400> SEQUENCE: 29

Met Asn Asp Ile Ser Gln Lys Ala Glu Ile Leu Leu Ser Ser Ser Lys
1               5                   10                  15

Pro Val Pro Lys Thr Tyr Val Pro Lys Leu Gly Lys Gly Asp Val Lys
                20                  25                  30

Asp Lys Phe Glu Ala Met Gln Arg Ala Arg Glu Glu Arg Asn Gln Arg
                35                  40                  45

Arg Ser Arg Asp Glu Lys Gln Arg Arg Lys Glu Gln Tyr Ile Arg Glu
50                  55                  60

Arg Glu Trp Asn Arg Arg Lys Gln Glu Ile Lys Glu Met Leu Ala Ser
65                  70                  75                  80

Asp Asp Glu Glu Asp Val Ser Ser Lys Val Glu Lys Ala Tyr Val Pro
                85                  90                  95

Lys Leu Thr Gly Thr Val Lys Gly Arg Phe Ala Glu Met Glu Lys Gln
                100                 105                 110

Arg Gln Glu Glu Gln Arg Lys Arg Thr Glu Glu Glu Arg Lys Arg Arg
                115                 120                 125

Ile Glu Gln Asp Met Leu Glu Lys Arg Lys Ile Gln Arg Glu Leu Ala
        130                 135                 140

Lys Arg Ala Glu Gln Ile Glu Asp Ile Asn Asn Thr Gly Thr Glu Ser
145                 150                 155                 160

Ala Ser Glu Glu Gly Asp Asp Ser Leu Leu Ile Thr Val Val Pro Val
                165                 170                 175

Lys Ser Tyr Lys Thr Ser Gly Lys Met Lys Lys Asn Phe Glu Asp Leu
                180                 185                 190

Glu Lys Glu Arg Glu Glu Lys Glu Arg Ile Lys Tyr Glu Glu Asp Lys
                195                 200                 205

Arg Ile Arg Tyr Glu Glu Gln Arg Pro Ser Leu Lys Glu Ala Lys Cys
        210                 215                 220

Leu Ser Leu Val Met Asp Asp Glu Ile Glu Ser Glu Ala Lys Lys Glu
225                 230                 235                 240

Ser Leu Ser Pro Gly Lys Leu Lys Leu Thr Phe Glu Glu Leu Glu Arg
                245                 250                 255

Gln Arg Gln Glu Asn Arg Lys Lys Gln Ala Glu Glu Glu Ala Arg Lys
                260                 265                 270
```

```
Arg Leu Glu Glu Glu Lys Arg Ala Phe Glu Ala Arg Gln Met
        275                 280                 285
Val Asn Glu Asp Glu Glu Asn Gln Asp Thr Ala Lys Ile Phe Lys Gly
290                 295                 300
Tyr Arg Pro Gly Lys Leu Lys Leu Ser Phe Glu Glu Met Glu Arg Gln
305                 310                 315                 320
Arg Arg Glu Asp Glu Lys Arg Lys Ala Glu Glu Ala Arg Arg Arg
                325                 330                 335
Ile Glu Glu Glu Lys Lys Ala Phe Ala Glu Ala Arg Arg Asn Met Val
                340                 345                 350
Val Asp Asp Asp Ser Pro Glu Met Tyr Lys Thr Ile Ser Gln Glu Phe
                355                 360                 365
Leu Thr Pro Gly Lys Leu Glu Ile Asn Phe Glu Glu Leu Leu Lys Gln
        370                 375                 380
Lys Met Glu Glu Glu Lys Arg Arg Thr Glu Glu Arg Lys His Lys
385                 390                 395                 400
Leu Glu Met Glu Lys Gln Glu Phe Glu Gln Leu Arg Gln Glu Met Gly
                405                 410                 415
Glu Glu Glu Glu Glu Asn Glu Thr Phe Gly Leu Ser Arg Glu Tyr Glu
                420                 425                 430
Glu Leu Ile Lys Leu Lys Arg Ser Gly Ser Ile Gln Ala Lys Asn Leu
        435                 440                 445
Lys Ser Lys Phe Glu Lys Ile Gly Gln Leu Ser Glu Lys Glu Ile Gln
450                 455                 460
Lys Lys Ile Glu Glu Arg Ala Arg Arg Ala Ile Asp Leu Glu
465                 470                 475                 480
Ile Lys Glu Arg Glu Ala Glu Asn Phe His Glu Glu Asp Val Asp
                485                 490                 495
Val Arg Pro Ala Arg Lys Ser Glu Ala Pro Phe Thr His Lys Val Asn
                500                 505                 510
Met Lys Ala Arg Phe Glu Gln Met Ala Lys Ala Arg Glu Glu Glu
        515                 520                 525
Gln Arg Arg Ile Glu Glu Gln Lys Leu Leu Arg Met Gln Phe Glu Gln
530                 535                 540
Arg Glu Ile Asp Ala Ala Leu Gln Lys Lys Arg Glu Glu Glu Glu
545                 550                 555                 560
Glu Glu Gly Ser Ile Met Asn Gly Ser Thr Ala Glu Asp Glu Gln
                565                 570                 575
Thr Arg Ser Gly Ala Pro Trp Phe Lys Lys Pro Leu Lys Asn Thr Ser
        580                 585                 590
Val Val Asp Ser Glu Pro Val Arg Phe Thr Val Lys Val Thr Gly Glu
                595                 600                 605
Pro Lys Pro Glu Ile Thr Trp Trp Phe Glu Gly Glu Ile Leu Gln Asp
        610                 615                 620
Gly Glu Asp Tyr Gln Tyr Ile Glu Arg Gly Glu Thr Tyr Cys Leu Tyr
625                 630                 635                 640
Leu Pro Glu Thr Phe Pro Glu Asp Gly Gly Glu Tyr Met Cys Lys Ala
                645                 650                 655
Val Asn Asn Lys Gly Ser Ala Ala Ser Thr Cys Ile Leu Thr Ile Glu
                660                 665                 670
Ser Lys Asn
        675
```